United States Patent
Ecker et al.

(10) Patent No.: US 9,968,788 B2
(45) Date of Patent: May 15, 2018

(54) TIMING COORDINATION OF IMPLANTABLE MEDICAL SENSOR MODULES

(75) Inventors: Robert Michael Ecker, Lino Lakes, MN (US); Kaustubh R. Patil, Blaine, MN (US); John Robert Hamilton, Centennial, CO (US); James D. Reinke, Maple Grove, MN (US); Timothy Davis, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 1976 days.

(21) Appl. No.: 12/361,977

(22) Filed: Jan. 29, 2009

(65) Prior Publication Data

US 2010/0106220 A1    Apr. 29, 2010

Related U.S. Application Data

(60) Provisional application No. 61/109,434, filed on Oct. 29, 2008.

(51) Int. Cl.
*A61B 5/00* (2006.01)
*A61N 1/365* (2006.01)
(Continued)

(52) U.S. Cl.
CPC ...... *A61N 1/36585* (2013.01); *A61B 5/02028* (2013.01); *A61B 5/1459* (2013.01); *A61B 5/14542* (2013.01); *A61B 5/7203* (2013.01)

(58) Field of Classification Search
CPC .............. A61B 5/1455; A61B 5/14552; A61B 5/14532
(Continued)

(56) References Cited

U.S. PATENT DOCUMENTS

| 4,374,382 A | 2/1983 | Markowitz |
| 4,750,495 A | 6/1988 | Moore et al. |

(Continued)

FOREIGN PATENT DOCUMENTS

| EP | 1764034 A2 | 3/2007 |
| WO | 0023146 A1 | 4/2000 |
| WO | 2008106597 A1 | 9/2008 |

OTHER PUBLICATIONS

American Heritage Dictionary Entry: switch.*
(Continued)

*Primary Examiner* — Daniel Cerioni

(57) ABSTRACT

In general, the disclosure is directed toward an implantable medical device that includes a plurality of sensor modules that are implanted within a patient. The sensor modules may cooperate with each other to coordinate the timing for performance of one or more sensor actions across the modules when making a measurement. Example measurements include tissue perfusion measurements, oxygen sensing measurements, sonomicrometry measurements, and pressure measurements. The coordination of the sensor modules may be controlled by a signal that is transmitted from a host controller to the sensor modules via a bus. In some examples, the bus may have two wires that transmit both timing information and data information to the sensor modules. The signal may be a signal that is substantially periodic, such as a pulsed signal. In additional examples, the signal may supply operating power and timing information to the sensor modules.

18 Claims, 28 Drawing Sheets

(51) Int. Cl.
*A61B 5/02* (2006.01)
*A61B 5/145* (2006.01)
*A61B 5/1459* (2006.01)

(58) Field of Classification Search
USPC .......................................... 600/310–344, 309
See application file for complete search history.

(56) References Cited

U.S. PATENT DOCUMENTS

| | | | | |
|---|---|---|---|---|
| 4,859,057 | A | * | 8/1989 | Taylor et al. ................. 600/473 |
| 5,386,827 | A | | 2/1995 | Chance et al. |
| 5,533,123 | A | * | 7/1996 | Force et al. ................... 713/189 |
| 5,961,450 | A | * | 10/1999 | Merchant et al. ............ 600/322 |
| 5,999,848 | A | | 12/1999 | Cord et al. |
| 6,163,723 | A | * | 12/2000 | Roberts et al. ................. 607/18 |
| 6,402,369 | B1 | * | 6/2002 | Ludington et al. ............. 374/13 |
| 6,516,808 | B2 | * | 2/2003 | Schulman ..................... 128/899 |
| 6,863,652 | B2 | | 3/2005 | Huang et al. |
| 6,944,488 | B2 | | 9/2005 | Roberts |
| 7,013,178 | B2 | * | 3/2006 | Reinke et al. ................... 607/60 |
| 7,139,613 | B2 | | 11/2006 | Reinke et al. |
| 7,840,246 | B1 | * | 11/2010 | Poore ............................ 600/339 |
| 2003/0055406 | A1 | * | 3/2003 | Lebel et al. ................ 604/891.1 |
| 2004/0059396 | A1 | * | 3/2004 | Reinke et al. .................. 607/60 |
| 2004/0181133 | A1 | * | 9/2004 | Al-Ali ........................... 600/323 |
| 2004/0220460 | A1 | * | 11/2004 | Roberts ......................... 600/333 |
| 2006/0064149 | A1 | * | 3/2006 | Belacazar et al. ............ 607/122 |
| 2007/0239215 | A1 | | 10/2007 | Bhunia et al. |
| 2008/0208020 | A1 | * | 8/2008 | Cinbis et al. ................. 600/323 |
| 2008/0208021 | A1 | * | 8/2008 | Cinbis et al. ................. 600/324 |
| 2008/0208269 | A1 | | 8/2008 | Cinbis et al. |

OTHER PUBLICATIONS

Office Action from U.S. Appl. No. 12/361,990 dated Nov. 13, 2012 (22 pages).
Invitation to Pay Additional Fees and Partial Search for PCT/US2009/062410, dated Feb. 26, 2010, (5 pp).
U.S. Appl. No. 12/361,990, filed Jan. 29, 2009 entitled "Closed Loop Parameter Adjustment for Sensor Modules of an Implantable Medical Device", by Ecker et al.
International Preliminary Report on Patentability from international application No. PCT/2009/062410, dated May 12, 2011, 12 pp.
Written Opinion and Search Report for PCT/US2009/062410, dated Jun. 30, 2010, (20 pp.).

* cited by examiner

TIMING COORDINATION OF IMPLANTABLE MEDICAL SENSOR MODULES

This application claims the benefit of U.S. Provisional Application No. 61/109,434, filed Oct. 29, 2008, which is hereby incorporated by reference in its entirety.

TECHNICAL FIELD

The disclosure relates to implantable medical systems, and, more particularly, to an implantable system having one or more medical sensor modules.

BACKGROUND

A variety of implantable medical devices (IMDs) for delivering a therapy or monitoring a physiologic condition of a patient have been clinically implanted or proposed for clinical implantation in patients. Some implantable medical devices may employ one or more elongated electrical leads and/or sensors. Such implantable medical devices may deliver therapy or monitor the heart, muscle, nerve, brain, stomach or other organs. In some cases, implantable medical devices deliver electrical stimulation therapy and/or monitor physiological signals via one or more electrodes or sensor elements, which may be included as part of one or more elongated implantable medical leads. Implantable medical leads may be configured to allow electrodes or sensors to be positioned at desired locations for delivery of stimulation or sensing. For example, electrodes or sensors may be located at a distal portion of the lead. A proximal portion of the lead may be coupled to an implantable medical device housing, which may contain electronic circuitry such as stimulation generation and/or sensing circuitry.

An implantable medical device may include a master device that communicates with a plurality of slave devices, such as sensor modules, in order to monitor various conditions including, for example, cardiac electrical activity, blood pressure, blood perfusion, and blood oxygen content. Both the master device and the slave devices may be implanted within the body. A bus may be used to provide communication between the master device and the slave devices. However, a large number of electrically conductive wires on the bus may cause interference and disturbance to the body of the patient. In addition, an implantable medical device may include an internal power source, usually in the form of a battery, which has a limited amount of available power. Because replacement of the implantable medical device requires surgery to the patient, conservation of power is an important consideration. Implantable medical devices often deliver life-supporting therapy in the form of electrical stimulation to the patient, which requires a reliable communication protocol between the master device and the implantable sensors.

SUMMARY

In general, the invention is directed toward an implantable medical device that includes a host controller and a plurality of sensor modules that are implanted within a patient. The host controller may control the sensor modules to perform one or more sensor actions in order to facilitate a measurement. The sensor modules may cooperate with each other to coordinate timing for performance of one or more sensor actions across the modules when making a measurement. When making a measurement, multiple sensor actions may need to occur in a particular order in order to obtain valid results for the measurement. In many cases, individual sensor actions may be performed by distinct sensor modules that share a common bus. By coordinating the timing for performance of sensor actions across the sensor modules, the sensor modules are able to control the timing for performance of the sensor actions such that all of the sensor actions occur in the desired order even if the individual sensor actions are performed by separate sensor modules. Example measurements include tissue perfusion measurements, blood oxygen sensing measurements, sonomicrometry measurements, and pressure measurements. The coordination of the sensor modules may be controlled by a control signal that is transmitted from a host controller to the sensor modules via a bus. In some examples, the control signal may transmit both timing information and data information to the sensor modules over a two-wire bus. In additional examples, the control signal may supply operating power, timing information, and data information to the sensor modules over a two-wire bus. The control signal may be a signal that is substantially periodic, such as a pulsed control signal.

In some examples, a host controller may configure the sensor modules to perform two or more different sensor actions in order to facilitate a measurement. For example, the host controller may configure a first subset of sensor modules to perform a first sensor action and a second subset of the sensor modules to perform a second sensor action. Both the first sensor action and the second sensor action may need to occur in a particular order in order to obtain valid results for the measurement. The host controller may transmit a control signal to the sensor modules to coordinate the timing for performance of the sensor actions across the sensor modules such that the sensor actions occur in the proper order.

In additional examples, the host controller may coordinate the timing of performance of multiple sensor actions within a single sensor module according to a pipelined execution scheme such that a time period for performance of a second sensor action for a previous measurement overlaps, at least partially, with a time period for performance of the first sensor action for a subsequent measurement. For each measurement, the first sensor action may need to occur prior to the second sensor action.

In further examples, the host controller and sensor modules may be capable of initiating a subsequent measurement prior to receiving results from the previous measurement. The sensor modules may be configured to store multiple measurements in a buffer and transmit the results to the host controller as a single packet over the bus.

In additional examples, the sensor modules may define one or more operational parameters that control various aspects of the sensor actions performed by the sensor modules. In some cases, one or more operational parameters may be stored in memory and/or registers associated with each sensor module. The host controller may automatically adjust one or more of the operational parameters based on measurement results received from previous measurements in order to provide closed loop parameter adjustment of the operational parameters stored within the sensor modules. The host controller may receive measurement results and adjust the operational parameters via the common bus. In some examples, the closed loop parameter adjustment algorithm may automatically adjust one or more operational parameters within the sensor modules such that the results for subsequent measurements are within a target range for further signal processing, such as for analog-to-digital conversion. In additional examples, the implantable medical device may periodically perform the closed loop parameter adjustment algorithm. By periodically performing the closed loop parameter adjustment algorithm, the implantable medical device may be able to automatically compensate for changes in measurement results due to patient motion, patient physiological condition, and/or device drift caused by electronic changes within the device.

In one example, the disclosure is directed to an implantable system that includes a host controller configured to transmit a signal over a bus. The implantable system further includes a plurality of sensor modules configured to receive the signal from the bus, and coordinate timing for performance of sensor actions across the sensor modules based on the received signal in order to make the measurement.

In another example, the disclosure is directed to a method that includes transmitting a signal over a bus. The method further includes receiving the signal from the bus with a plurality of sensor modules. The method further includes coordinating timing for performance of sensor actions across the sensor modules based on the received signal in order to make the measurement.

In another example, the disclosure is directed to an apparatus that includes means for transmitting a signal over a bus. The apparatus further includes means for receiving the signal from the bus with a plurality of sensor modules. The apparatus further includes means for coordinating timing for performance of sensor actions across the sensor modules based on the received signal in order to make the measurement.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
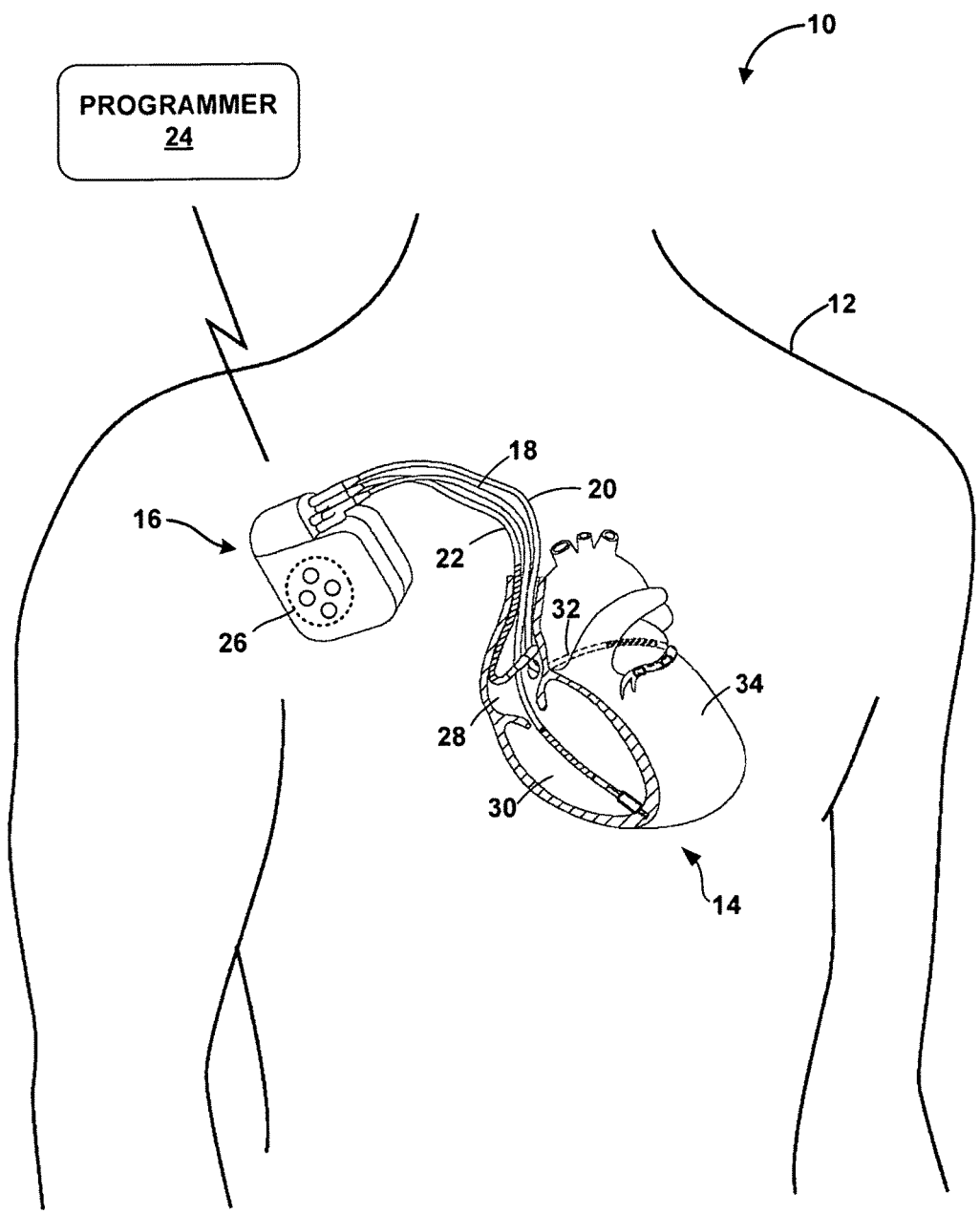
FIG. 1 is a conceptual diagram illustrating an example system that may be used to monitor one or more physiological parameters of a patient and/or provide therapy to the heart of a patient.

In general, the invention is directed toward an implantable medical device that includes a controller and a plurality of sensor modules that are implanted within a patient. The controller may control the sensor modules to perform one or more sensor actions in order to facilitate a measurement. The sensor modules may cooperate with each other to coordinate timing for performance of one or more sensor actions across the modules when making a measurement. When making a measurement, multiple sensor actions may need to occur in a particular order in order to obtain valid results for the measurement. In many cases, individual sensor actions may be performed by distinct sensor modules that share a common bus. By coordinating the timing for performance of sensor actions across the sensor modules, the sensor modules are able to control the timing for performance of the sensor actions such that all of the sensor actions occur in the desired order even if the individual sensor actions are performed by separate sensor modules. Example measurements include tissue perfusion measurements, blood oxygen sensing measurements, sonomicrometry measurements, and pressure measurements. The coordination of the sensor modules may be controlled by a control signal that is transmitted from a controller to the sensor modules via a bus. In some examples, the control signal may transmit both timing information and data information to the sensor modules over a two-wire bus. In additional examples, the control signal may supply operating power, timing information, and data information to the sensor modules over a two-wire bus. The control signal may be a signal that is substantially periodic, such as a pulsed control signal.

In some examples, a controller may configure the sensor modules to perform two or more different sensor actions in order to facilitate a measurement. For example, the controller may configure a first subset of sensor modules to perform a first sensor action and a second subset of the sensor modules to perform a second sensor action. Both the first sensor action and the second sensor action may need to occur in a particular order in order to obtain valid results for the measurement. The controller may transmit a control signal to the sensor modules to coordinate the timing for performance of the sensor actions across the sensor modules such that the sensor actions occur in the proper order.

In additional examples, the controller may coordinate the timing of performance of multiple sensor actions within a single sensor module according to a pipelined execution scheme such that a time period for performance of a second sensor action for a previous measurement overlaps, at least partially, with a time period for performance of the first sensor action for a subsequent measurement. For each measurement, the first sensor action may need to occur prior to the second sensor action.

In further examples, the controller and sensor modules may be capable of initiating a subsequent measurement prior to receiving results from the previous measurement. The sensor modules may be configured to store multiple measurements in a buffer and transmit the results to the controller as a single packet over the bus.

In additional examples, the sensor modules may define one or more operational parameters that control various aspects of the sensor actions performed by the sensor modules. In some cases, one or more operational parameters may be stored in memory and/or registers associated with each sensor module. The controller may automatically adjust one or more of the operational parameters based on results received from previous measurements in order to provide closed loop parameter adjustment of the operational parameters associated with the sensor modules. The controller may receive measurement results and adjust the operational parameters via the common bus. In some examples, the closed loop parameter adjustment algorithm may automatically adjust one or more operational parameters within the sensor modules such that the results for subsequent measurements are within a target range for further signal processing, such as for analog-to-digital conversion. In additional examples, the implantable medical device may periodically perform the closed loop parameter adjustment algorithm. By periodically performing the closed loop parameter adjustment algorithm, the implantable medical device may be able to automatically compensate for changes in measurement results due to patient motion, patient physiological condition, and/or device drift caused by electronic changes within the device.

FIG. 1 is a conceptual diagram illustrating an example system 10 that may be used to monitor one or more physiological parameters of patient 12 or provide therapy to heart 14 of patient 12. Patient 12 ordinarily, but not necessarily, will be a human. System 10 includes an implantable medical device (IMD) 16, leads 18, 20 and 22, and programmer 24. IMD 16 may be, for example, an implantable pacemaker, cardioverter, and/or defibrillator that provides electrical signals to heart 32 via electrodes coupled to one or more of leads 18, 20, and 22. IMD 16 may also be an implantable monitor that does not provide therapy (e.g., stimulation therapy) to patient 12. In other examples, IMD 16 may be incorporated into other therapy delivery devices, such as a neurostimulator. Neither IMD 16 nor optical perfusion sensor 26 or any of the figures shown herein are drawn to any particular scale.

IMD 16 includes an optical perfusion sensor 26 that has a plurality of sensor modules situated on the can, i.e., housing, of implantable medical device 16. Optical perfusion sensor 26 may measure blood perfusion at a tissue site of patient 12 proximate to IMD 16, or may measure a blood oxygen saturation level of the blood surrounding IMD 16. As shown in FIG. 1, optical perfusion sensor 26 contains a plurality of windows that may correspond to the plurality of sensor modules for the optical perfusion sensor. Each of the sensor modules may be electrically coupled to a common bus via a port. In some examples, multiple sensor modules may be electrically coupled to the bus via the same port (i.e. a common port). In other examples, multiple sensor modules may be electrically coupled to the bus via different ports (i.e. a port dedicated for each sensor module). The bus may be a 2-wire or 3-wire bus that facilitates communication between the sensor modules and the other circuitry within IMD 16. Even though a single bus may be the only means of communication between the sensor modules, the plurality of sensor modules may be configured to coordinate timing for performance of one or more sensor actions across multiple sensor modules according to the techniques in this disclosure in order to facilitate a single measurement.

In the example shown in FIG. 1, IMD 16 is implanted within a subcutaneous tissue layer of patient 12. In other examples, IMD 16 may be implanted within other tissue sites, such as a submuscular location. IMD 16 may be a temporary diagnostic tool employed to monitor one or more physiological parameters of patient 12 for a relatively short period of time (e.g., days or weeks), or may be used on a more permanent basis, such as to provide prolonged monitoring or control therapy delivery to patient 12.

Leads 18, 20, 22 extend into the heart 14 of patient 12 to sense electrical activity of heart 14 and/or deliver electrical stimulation to heart 14. In the example shown in FIG. 1, right ventricular (RV) lead 18 extends through one or more veins (not shown), the superior vena cava (not shown), and right atrium 28, and into right ventricle 30. Left ventricular (LV) coronary sinus lead 20 extends through one or more veins, the vena cava, right atrium 28, and into the coronary sinus 32 to a region adjacent to the free wall of left ventricle 34 of heart 14. Right atrial (RA) lead 22 extends through one or more veins and the vena cava, and into the right atrium 28 of heart 14.

IMD 16 may sense electrical signals attendant to the depolarization and repolarization of heart 14 via electrodes (not shown in FIG. 1) coupled to at least one of the leads 18, 20, 22. In some examples, IMD 16 provides pacing pulses to heart 14 based on the electrical signals sensed within heart 14. The configurations of electrodes used by IMD 16 for sensing and pacing may be unipolar or bipolar. IMD 16 may also provide defibrillation therapy and/or cardioversion therapy via electrodes located on at least one of the leads 18, 20, 22. IMD 16 may detect arrhythmia of heart 14, such as fibrillation of ventricles 30 and 34, and deliver defibrillation therapy to heart 14 in the form of electrical shocks. In some examples, IMD 16 may be programmed to deliver a progression of therapies, e.g., cardioversion pulses with increasing energy levels and/or defibrillation shocks, until a fibrillation of heart 14 is stopped. IMD 16 detects fibrillation employing one or more fibrillation detection techniques known in the art.

IMD 16 includes an optical perfusion sensor 26 that generates a signal indicative of an amount of tissue perfusion at a tissue site proximate to sensor 26. In some cases, optical perfusion sensor 26 may function as a "pulse oximeter" and measure a blood oxygen saturation level of blood in a tissue site proximate to optical perfusion sensor 26. The blood oxygen saturation level may be indicative of various hemodynamic characteristics, such as blood pressure of patient 12 or a relative blood flow through the tissue site. In other cases, optical perfusion sensor 26 may function as a tissue perfusion sensor that measures an amount of tissue perfusion at a tissue site proximate to implantable medical device 16. Tissue perfusion may generally refer to an amount of blood perfused within the tissue. The amount of tissue perfusion may be indicative of a patient condition, such as ventricular fibrillation. For example, low tissue perfusion may indicate low blood output from heart 14, e.g., as a result of fibrillation. Hence, in some examples, tissue perfusion may be used as a cross-correlation with other sensed data such as sensed cardiac arrhythmias to confirm that the patient is experiencing fibrillation. In this manner, tissue perfusion can be used to provide an increased confidence in a fibrillation detection prior to delivering a defibrillation shock to the patient.

Optical perfusion sensor 26 includes at least one light source that emits light at a particular wavelength, which scatters through blood-perfused tissue, and at least one detector that senses the light that is emitted from the light source, and which traverses through blood-perfused tissue and, in some cases, is reflected by a blood mass (e.g., blood in a blood vessel) of patient 12. In some examples, one of the sensor modules may be configured to be a light source and another one of the sensor modules may be configured to be a light detector. In other examples, one or more of the sensor modules may be configured to be both a light emitter and a light detector. Hence, sensor modules may be single-purpose modules that either emit or detect light, or dual-purpose modules that are capable of both emitting and detecting light. Single-purpose emitter and detector modules may be used together to sense tissue perfusion. Likewise, the emitter in a dual-purpose module may be used in conjunction with a detector in the same module or in a different module to sense tissue perfusion.

IMD 16 may be implanted within patient 12 such that optical perfusion sensor 26 is adjacent to blood-perfused tissue. For example, optical perfusion sensor 26 may be positioned proximate and external to tissue that is near a blood mass (e.g., vasculature, such as one or more blood vessels) of patient 12. In other examples, optical perfusion sensor 26 may be positioned within a vein or other vasculature of patient 12. IMD 16 may be oriented such that optical perfusion sensor 26, or at least the light source and detector, face away from the epidermis of patient 12 in order to help minimize interference from background light, e.g., from outside of the patient's body. Background or ambient light may include light from a source other than the one or more light sources of optical perfusion sensor 26. Detection of the background light by the detector of optical perfusion sensor 26 may result in an inaccurate and imprecise reading of the level of blood oxygen saturation of the adjacent tissue. In some examples, however, optical perfusion sensor 26 may measure the ambient light to estimate the noise created by the background light. Optical perfusion sensor 26 may then use post-processing of the measured data to subtract out components of the resulting signal that are from the background or ambient light.

The optical properties of blood-perfused tissue may change depending upon the relative amounts of oxygenated and deoxygenated hemoglobin, due, at least in part, to the different optical absorption spectra of oxygenated and deoxygenated hemoglobin. That is, the oxygen saturation level of the patient's blood may affect the amount of light that is absorbed by a blood mass within the tissue observed by optical perfusion sensor 26 and the amount of light that is reflected by the blood mass. Oxygenated and deoxygenated hemoglobin within the blood may absorb different wavelengths of light. An electrical signal generated by optical perfusion sensor 26 that indicates the intensity of one or more wavelengths of light detected by the detector of sensor 26 may change based on the relative amounts of oxygenated and deoxygenated hemoglobin in the blood mass within the blood-perfused tissue proximate to sensor 26. Accordingly, the intensity of light that is emitted by the light source of sensor 26 and reflected by blood may indicate relative blood oxygen saturation levels. At least some of the light reflected by the blood may be detected by the detector of optical perfusion sensor 26.

Changes in blood oxygenation of the tissue adjacent to optical perfusion sensor 26 may indicate various hemodynamic characteristics of patient 12. An example of a hemodynamic characteristic that may be derived from a signal generated by optical perfusion sensor 26 includes arterial blood pressure of patient 12. In some cases, the signal generated by optical perfusion sensor 26 may indicate the blood oxygen saturation level of the tissue.

The presence of cardiac arrhythmias may be derived from a signal generated by optical perfusion sensor 26. Electrical signals generated by the detector of optical perfusion sensor 26 may experience a significant change in value following a hemodynamically unstable ventricular fibrillation. For example, an increase in a red optical signal sensed by the detector, which may indicate the amount of red light from the red LED that was reflected by blood in the tissue proximate to optical perfusion sensor 26, and a decrease in an IR signal sensed by the detector, which may indicate the amount of IR light from the IR LED that was reflected by blood in the tissue in blood-perfused tissue, may indicate the occurrence of a cardiac arrhythmia.

As another example, the signal generated by optical perfusion sensor 26 may indicate the relative change in hemoglobin of the blood-perfused tissue that is saturated with oxygen as well as the change in hemoglobin concentration in the tissue. An optical oxygenation ($O_2$) variation index (also referred to as an $O_2$ index) may be calculated based on the intensity of light detected by the one or more detectors of optical perfusion sensor 26. A monotonically decreasing trend in the $O_2$ variation index at the onset of a cardiac arrhythmia may confirm the event to be hemodynamically unstable, and thereby indicate ventricular fibrillation.

Programmer 24 is capable of communicating with IMD 16 via wireless telemetry. Programmer 24 may be a handheld computing device or a computer workstation. Programmer 24 may include a user interface that receives input from a user. The user interface may include, for example, a keypad and a display, which may, for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some examples, a display of programmer 24 may include a touch screen display, and a user may interact with programmer 24 via the display.

A user, such as a physician, technician, or other clinician, may interact with programmer 24 to communicate with IMD 16. For example, the user may interact with programmer 24 to retrieve physiological or diagnostic information from IMD 16. A user may also interact with programmer 24 to program IMD 16 (e.g., to select values for operational parameters). For example, the user may use programmer 24 to retrieve information from IMD 16 regarding the rhythm of heart 14, trends therein over time, or arrhythmic episodes. As another example, the user may use programmer 24 to retrieve information from IMD 16 regarding other sensed physiological signals or conditions of heart 12, such as tissue perfusion, blood oxygen content, intracardiac or intravascular pressure, activity, posture, perfusion, respiration, or thoracic impedance. As another example, the user may use programmer 24 to retrieve information from IMD 16 regarding the performance or integrity of IMD 16 or other components of system 10, such as leads 18, 20 and 22.

The user may use programmer 24 to program a therapy progression, select electrodes used to deliver pacing pulses, cardioversion shocks, defibrillation shocks, select waveforms for the defibrillation shocks, or select or configure a fibrillation detection algorithm for IMD 16. The user may also use programmer 24 to program aspects of other therapies provided by IMD 16, such as cardioversion, defibrillation or pacing therapies. In some examples, the user may activate certain features of IMD 16 by entering a single command via programmer 24, such as depression of a single key or combination of keys of a keypad or a single point-and-select action with a pointing device.

According to this disclosure, a user may use programmer 24 to configure parameters for one or more of the plurality of sensing modules. For example, a user may use programmer 24 to configure a first sensor module to be a light source and a second sensor module to be a light detector. A user may also use programmer 24 to configure various measurement calibration parameters, such as how long the light detector should measure the light during a single measurement, how much current should be used by the light sources, or what kind of resolution the results of the optical perfusion measurements should have. In one example, programmer 24 may be used to program and/or adjust the integration time (Tint) parameter, the light emitting diode current (LEDi) parameter, and the integration capacitor (Cint) parameter. Programmer 24 may also graphically display the results of various measurements described in this disclosure, such as an $O_2$ index, perfusion events, and perfusion trends. Example perfusion events displayed by programmer 24 may include "high rate episode" events such as ventricular fibrillation (VF) or ventricular tachycardia (VT) events.

Programmer 24 may communicate with IMD 16 via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near IMD 16 implant site in order to improve the quality or security of communication with programmer 24.

Figure 2:
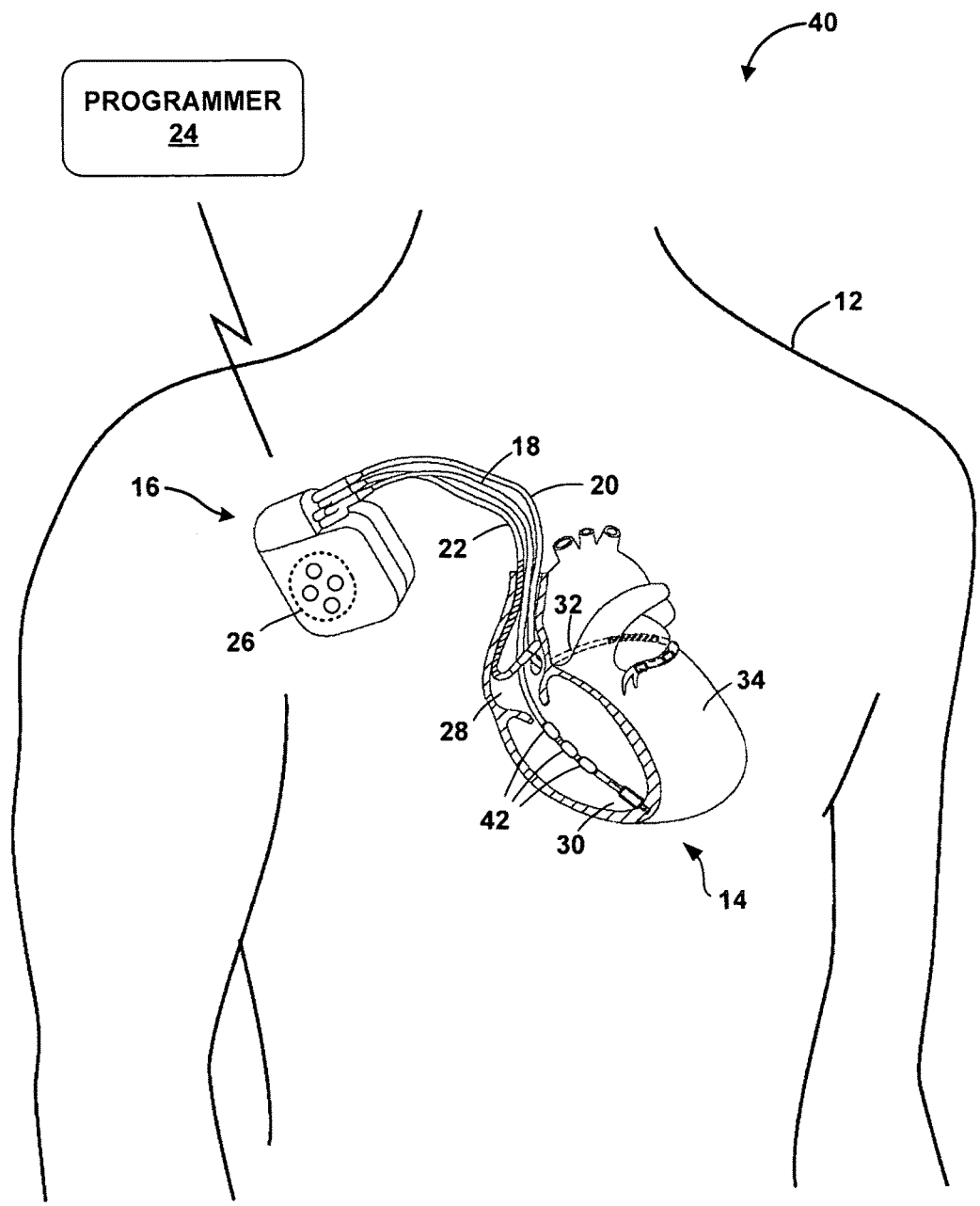
FIG. 2 is another conceptual diagram illustrating an example system that may be used to monitor one or more physiological parameters of a patient and/or provide therapy to the heart of a patient.

FIG. 2 is another conceptual diagram illustrating an example system 40 that may be used to monitor one or more physiological parameters of a patient or provide therapy to the heart of a patient. Many of the components in system 40 are substantially similar to the components in system 10 of FIG. 1 and have been numbered with identical reference numerals. In addition to the features already described above in FIG. 1, system 40 also includes a right ventricular (RV) lead 18 that has a plurality of sensor modules 42 for performing measurements inside heart 14 of patient 12. In some examples, sensor modules 42 may be optical perfusion sensor modules configured to emit and detect light in a manner similar to optical perfusion sensor 26. In other examples, sensor modules 42 may be configured to measure pressure or other physiological parameters within heart 14 of patient 12. In any case, lead 18 may be equipped with a 2-wire or 3-wire bus that facilitates communications between a host controller situated in the can of IMD 16 and sensor modules 42 located toward the distal end of lead 18 in the right ventricle. In particular, the 2-wire or 3-wire bus may be formed by two or three elongated conductors that extend along the length of the body of lead 18 to sensor modules 42. Although sensor modules 42 have been depicted on lead 18 for purposes of illustration, it should be noted that one or more sensor modules may be disposed on any of the leads within system 40 in any combination without departing from the scope of the disclosure.

Figure 3:
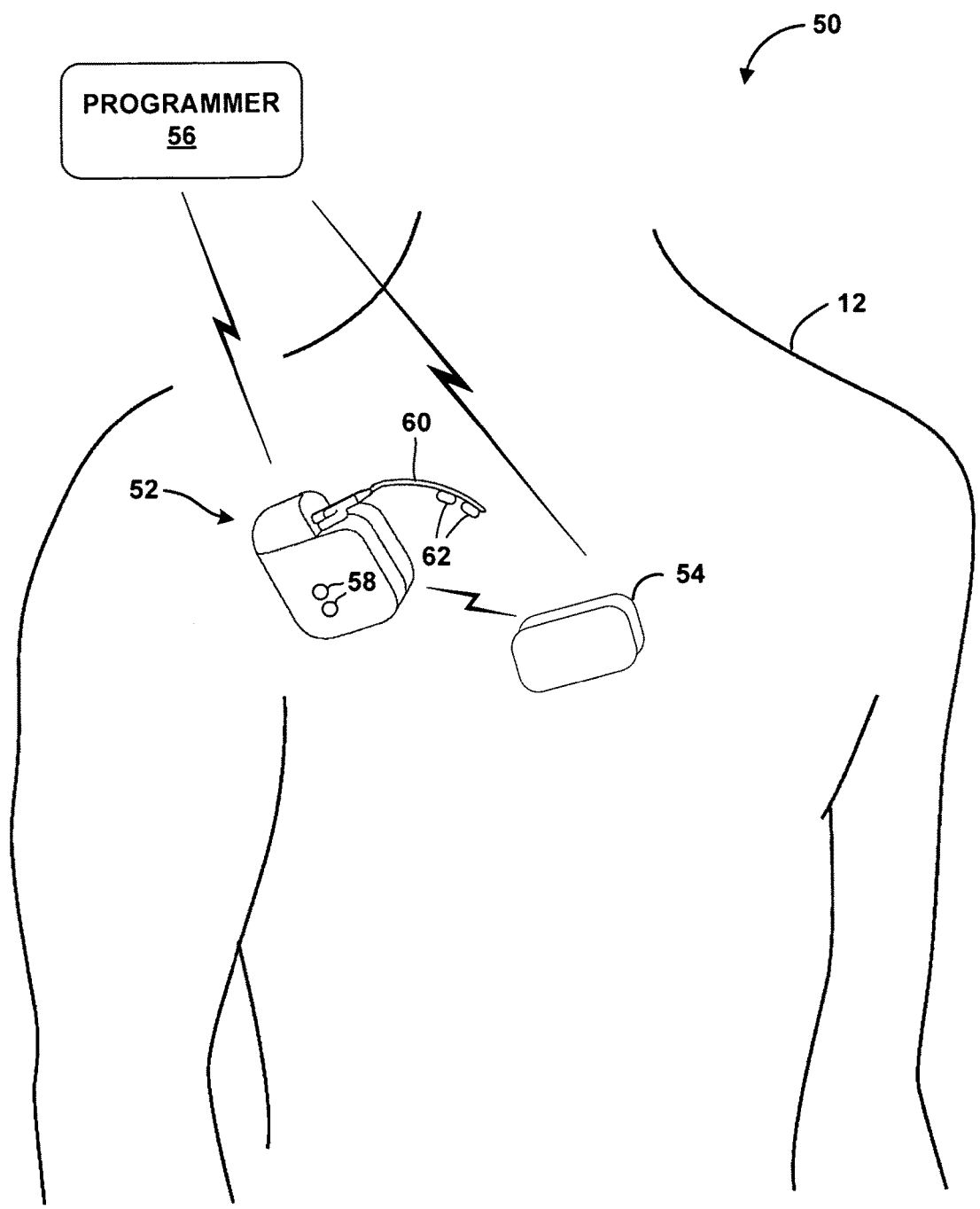
FIG. 3 is another conceptual diagram illustrating an example system that may be used to monitor one or more physiological parameters of a patient and/or provide therapy to the heart of a patient.

FIG. 3 is another conceptual diagram illustrating an example system that may be used to monitor one or more physiological parameters of a patient or provide therapy to the heart of a patient. System 50 includes implantable medical device 52, implantable medical device 54, and programmer 56. Programmer 56 is substantially similar programmer 24 illustrated in FIGS. 1 and 2 except that programmer 56 is also capable of wireless communication with IMD 54 in addition to IMD 52. IMD 54 may be an implantable cardiac defibrillator (ICD) capable of generating pacing pulses, cardioversion shocks, and/or a defibrillation shocks. For example, IMD 54 may be capable of delivering defibrillation shocks when a ventricular fibrillation condition is detected. IMD 54 is capable of communicating wirelessly with IMD 52. For ease of illustration, IMD 54 is shown as a block. In practice however, IMD 54 may be constructed in a manner similar to the devices of FIGS. 1 and 2, with the exception that perfusion sensor components may be provided separately in association with IMD 52.

IMD 52 is configured to monitor one or more physiological parameters of a patient. IMD 52 includes electrodes 58, lead 60, and sensor modules 62. Electrodes 58 may measure electrical activity of the heart (now shown) of patient 12 and produce a signal, such as an EGM signal indicative of the electrical activity. Lead 60 extends outward from IMD 52 for deployment within a target tissue site. Lead 60 is a dedicated lead for sensor modules 62 and includes a two-wire or three-wire bus formed by internal conductors that facilitate communication with sensor modules 62. Sensor modules 62 may be optical sensor modules configured to emit light and/or detect light. IMD 52 may be configured to make an EGM measurement via electrodes 58 to determine if the heart of patient 12 is experiencing a ventricular fibrillation condition. If the EGM measurements indicate that a ventricular fibrillation condition is likely, then IMD 52 may activate sensor modules 62 to perform tissue perfusion measurements. Based on the tissue perfusion measurements, IMD 52 may provide confirmation to ICD 54 of a detected fibrillation, in which case ICD 54 may more reliably deliver a shock to the heart of patient 12. ICD 54 may itself monitor cardiac signals to identify fibrillation and receive signals from ICD 52 to confirm the fibrillation based on a tissue perfusion change that is coincident with the fibrillation. If the tissue perfusion measurements obtained by IMD 52 corroborate that patient 12 is experiencing a ventricular fibrillation condition detected by IMD 54, then IMD 54 may deliver a defibrillation shock. Otherwise, if the tissue perfusion measurements do not correlate with ventricular defibrillation, IMD 54 may not deliver a shock to the heart of patient 12. IMD 52 may transmit tissue perfusion measurements to IMD 54 to confirm fibrillation, or simply send a confirmation signal to IMD 54 when IMD 52 obtains a tissue perfusion measurement that is consistent with fibrillation.

Figure 4:
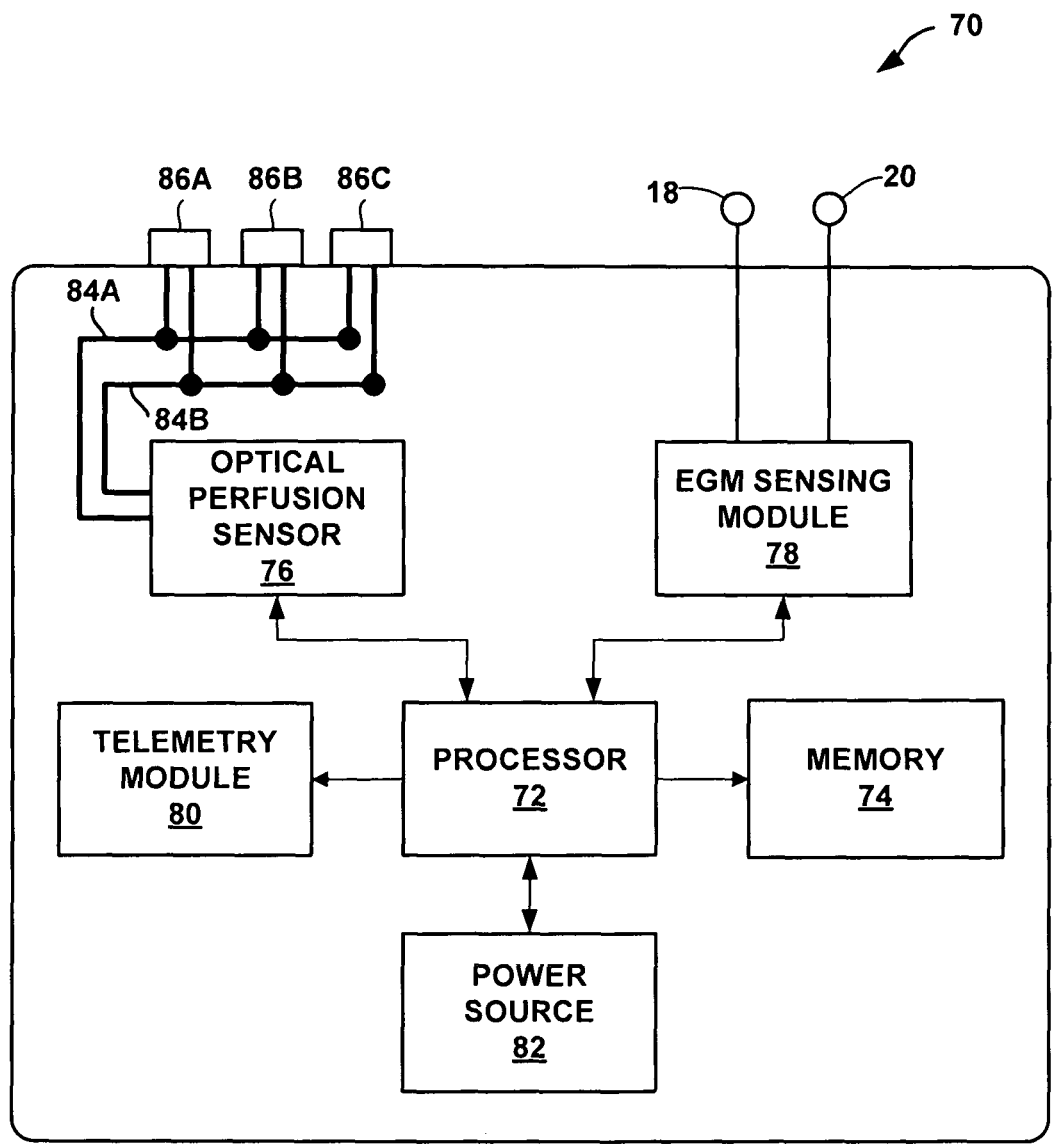
FIG. 4 is a block diagram illustrating an example implantable medical device that includes an optical perfusion sensor.

FIG. 4 is a block diagram illustrating an example implantable medical device 70 that includes an optical perfusion sensor. IMD 70 may generally correspond to IMD 26 shown in FIGS. 1 and 2, although IMD 70 may also be suitable for use within system 50 of FIG. 3. In the example shown in FIG. 4, IMD 70 includes processor 72, memory 74, optical perfusion sensor 76, EGM sensing module 78, telemetry module 80, power source 82, bus 84, and sensor modules 86A-86C. Processor 72 controls optical perfusion sensor 76 and EGM sensing module 78 to perform various sensing measurements. Processor 72 may also store sensed data from either of these sensors into memory 74 and retrieve the data for later use. For example, processor 72 may transmit the data via telemetry module 80 to a programmer or other device external to implantable medical device 70.

Memory 74 stores data that is measured by any of the sensing modules in IMD 70 as well as any calculation data or other configuration data for IMD 70. Memory 74 may also include computer-readable instructions that, when executed by processor 72, cause IMD 70 and processor 72 to perform various functions attributed to IMD 70 and processor 72 herein. Memory 74 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 72 may include one or more microprocessors, controllers, digital signal processors (DSPs), application specific integrated circuits (ASICs), field-programmable gate arrays (FPGAs), or equivalent discrete or integrated logic circuitry, or combinations thereof. In some examples, processor 72 may include multiple components, such as any combination of one or more microprocessors, one or more controllers, one or more DSPs, one or more ASICs, or one or more FPGAs, as well as other discrete or integrated logic circuitry. The functions attributed to processor 72 herein may be embodied as software, firmware, hardware or any combination thereof. Processor 72 controls optical perfusion sensor 76 to measure tissue perfusion and/or blood oxygen content at tissue sites surrounding IMD 70. Processor 72 also controls electrogram (EGM) sensing module 78 to sense EGM signals of heart 14 of patient 12 and stores EGM signals from EGM sensing module 78 in memory 74.

Optical perfusion sensor 76 is electrically coupled to sensor modules 86A-86C via two-wire bus 84, comprising wires 84A and 84B. Two-wire bus 84 may provide power, data, and timing information to sensor modules 86A-86C. In some examples, two-wire bus 84 may also contain a third wire that provides an additional source of power for sensing elements that require high currents, such as light emitting diodes. Optical perfusion sensor 76 may comprise a host controller that acts a master device for controlling sensor modules 86A-86C and for controlling communications over bus 84. Optical perfusion sensor 76 is electrically coupled to processor 72. In some cases, portions of optical perfusion sensor 76 and processor 72 may be implemented on the same programmable processor.

Sensor modules 86A-86C may each include device electronics and a transparent window to allow light to enter and/or leave the sensor modules. In some cases, sensor modules 86A-86C may be mounted on a common circuit board and positioned to extend through or align with windowed apertures in the housing of device 70. As shown in FIG. 4, sensor modules 86A-86C are oriented in a straight-line configuration on the housing of IMD 70. However, sensor modules 86A-86C may also take on other configurations. For example, sensor modules 86A-86C may be arranged in an equidistant fashion where each sensor module 86A-86C corresponds to a vertex of an equilateral triangle. In addition, although sensor modules 86A-86C are depicted as being attached to the outer surface of IMD 70, sensor modules may be disposed within IMD 70 such that the windows of the modules are even with the outer surface of the housing of IMD 70. In one example, the center-to-center distance between windows of different sensor modules may be spaced at a distance of approximately 7 millimeters (mm) to 12 millimeters (mm).

Optical perfusion sensor 76 is capable of configuring sensor modules 86A-86C such that at least one of the sensor modules is configured to be a light emitter module and at least one of the sensor modules is configured to be a light detector module. In some cases, the same sensor module may be configured to be both a light emitter module and a light detector module. In general, light produced by an emitting sensor module will travel through the blood-perfused tissue. Some of the light will be reflected back to the detecting sensor module. The detecting sensor module measures an amount or intensity of the reflected light received over a period of time. The measured amount of received light is indicative of a blood perfusion level or an amount of blood oxygen content in the tissue. In some examples, the sensor modules may operate in a transmissive mode. In such examples, the tissue site may reside between the detecting sensor modules, and the detecting sensor module may measure light that is transmitted through the tissue.

Optical perfusion sensor 76 is capable of transmitting a signal over bus 84A, 84B in order to coordinate the timing for performance of sensor actions across the sensor modules when performing an optical measurement. For example, optical perfusion sensor 76 may control the sensor modules such that sensor module 86A begins to emit light prior to sensor module 86B beginning to detect light. As another example, optical perfusion sensor 76 may control sensor modules 86A-86C such that sensor module 86B ceases to detect light prior to sensor module 86A ceasing to emit light. In this manner, optical perfusion sensor 76 coordinates the timing for performance of the actions across sensor modules 86A-86C to ensure that the light emitter and the light detector are activated and deactivated (i.e. "turned on" and "turned off") in the proper order. This ensures that light is always being emitted during a light detection measurement.

Sensor modules 86A-86C may be configured to coordinate the timing for performance of sensor actions across the sensor modules based on the signal received from optical perfusion sensor 76. In particular, sensor modules 86A-86C may be configured to analyze the signal received from optical perfusion sensor 76 over bus 84 to detect various signal conditions. For example, sensor module 86A may detect a first signal condition and perform a first sensor action in response to detecting the first signal condition. Similarly, sensor module 86B may detect a second signal condition and perform a second sensor action in response to detecting the second signal condition. The signal generated by optical perfusion sensor 76 may be configured such that the first signal condition necessarily occurs prior to the second signal condition. Thus, sensor module 86A will perform the first sensor action prior to sensor module 86B performing the second sensor action.

Optical perfusion sensor 76 may configure any subset of sensor modules 86A-86C to be light emitters and any other subset of sensor modules 86A-86C to be light detectors. In some cases, optical perfusion sensor 76 may configure sensor modules 86A-86C in a single emitter/single detector scheme. For example, optical perfusion sensor 76 may configure sensor module 86A to be an emitter and sensor module 86B to be a detector. In other cases, optical perfusion sensor 76 may configure sensor modules 86A-86C in a single emitter/dual detector scheme. For example, optical perfusion sensor 76 may configure sensor module 86B to be an emitter and sensor modules 86A and 86C to both be detectors. The sensor modules need not necessarily be located adjacent to each other. For example, sensor module 86A may be configured as an emitter and sensor module 86C may be configured as a detector.

EGM sensing module 78 is electrically coupled to electrodes 18, 20. Electrodes 18, 20 may be coupled to a surface of an outer housing of IMD 16 to form can electrodes or may be deployed on one or more medical leads that extend from the housing. In some examples in which electrodes 18, 20 are coupled to a surface of the outer housing of IMD 16, electrodes 18, 20 may be formed by the housing (e.g., by exposed portions of an electrically conductive housing) or may be attached to the outer surface of the housing.

EGM sensing module 78 monitors signals from at least one of electrodes 18, 20 in order to monitor electrical activity of heart 32, e.g., via EGM signals. In other examples, EGM sensing module 78 may be electrically coupled to more than two electrodes. In some examples, EGM sensing module 78 may include narrow band channels that detect cardiac events such as P waves and R waves. Also, EGM sensing module 78 may include a channel that comprises an amplifier with a relatively wide-band. Signals from sensing electrodes 18, 20 may be coupled to the wide-band amplifier and provided to a multiplexer. Thereafter, the signals may be converted to multi-bit digital signals by an analog-to-digital converter for storage in memory 74 as an EGM. In some examples, the storage of such EGMs in memory 74 may be under the control of a direct memory access circuit.

Processor 72 may employ digital signal analysis techniques to characterize the digitized signals stored in memory 74 from optical perfusion sensor 76 and EGM sensing module 78. The analysis technique may allow processor 72 to detect and classify the patient's heart rhythm, level of tissue perfusion, and/or blood oxygen content. Processor 72 may employ any of the numerous signal processing methodologies known in the art to assist in the analysis. In other examples, such processing may be done by another processor external to IMD 70, such as a processor within programmer 24 or another external computing device.

Processor 72 may generate and store marker channel codes in some examples. The marker codes may be indicative of different cardiac episodes that EGM sensing module 78 detects, and store the marker codes in memory 74 and/or transmit the marker codes to an external computing device. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

Telemetry module 80 includes any suitable hardware, firmware, software or any combination thereof for communicating with another device, such as ICD 54 (FIG. 3) or programmer 24 (FIG. 1). Under the control of processor 72, telemetry module 80 may receive downlink telemetry from and send uplink telemetry to programmer 24 or another external device with the aid of an antenna, which may be internal and/or external. Processor 72 may provide the data to be uplinked to programmer 24 and the control signals for the telemetry circuit within telemetry module 80, e.g., via an address/data bus. In some examples, telemetry module 80 may provide received data to processor 72 via a multiplexer.

The various components of IMD 70 are coupled to power source 82, which may include a rechargeable or non-rechargeable battery and suitable power supply circuitry. A non-rechargeable battery may be selected to last for several years, while a rechargeable battery may be inductively charged from an external device, e.g., on a daily or weekly basis.

The block diagram shown in FIG. 4 is merely one example of an implantable medical device for use within systems 10, 40 and 50 of FIGS. 1-3. In other examples, IMD 70 may include fewer or more components. For example, when IMD 70 is incorporated with a medical device that delivers therapy to patient 12, IMD 70 may also include a therapy delivery module, such as an electrical stimulation generator or a fluid pump. For example, IMD 70 may include a therapy delivery module that delivers pacing, defibrillation or cardioversion stimulation to heart 14 (FIG. 1) of patient 12, and/or may generate and deliver neurostimulation signals to a target tissue site within patient 12 (e.g., proximate to a spine or nerve, or to a target region of tissue that may or may not be near a nerve).

Although optical perfusion sensor 76 and EGM sensing module 78 are shown to be separate from processor 72 in FIG. 4, in other examples, processor 72 may include the functionality attributed to optical perfusion sensor 76 and/or EGM sensing module 78 herein. For example, optical perfusion sensor 76 and EGM sensing module 78 shown in FIG. 4 may include software executed by processor 72. If optical perfusion sensor 76 or EGM sensing module 78 includes firmware or hardware, optical perfusion sensor 76 or EGM sensing module, respectively, may be a separate one of the one or more processors 72 or may be a part of a multifunction processor. As previously described, processor 72 may comprise one or more processors.

In some examples, some of the components of IMD 70 shown in the example of FIG. 4 may be relocated in another device. For example, optical perfusion sensor 76 may be separate from IMD 70. That is, although optical perfusion sensor 76 is shown in FIG. 4 to be incorporated within a housing of IMD 70 that also encloses other components, such as processor 72 and EGM sensing module 78, in other examples, optical perfusion sensor 76 may be enclosed in a separate housing as part of a separate optical perfusion sensor 76. Optical perfusion sensor 76 that is enclosed in a separate housing from the IMD 16 housing may be mechanically coupled to IMD 16 or may be mechanically decoupled from IMD 16. In some examples, optical perfusion sensor 76 including sensor modules having light sources and light detectors may be implanted within patient 12 at a separate location from IMD 70. Optical perfusion sensor 76 may communicate with IMD 70 via a wired connection or via wireless communication techniques, such as RF telemetry.

In yet other examples, at least a part of optical perfusion sensor 76 may be external to patient 12. For example, in some implementations, optical perfusion sensor 76 may monitor the blood oxygen saturation level of tissue of patient 12 through an epidermis of patient (e.g., through skin on a finger, earlobe or forehead of patient 12). Optical perfusion sensor 76 may transmit the electrical signals generated by the sensor modules that are indicative of the sensed intensity of red light and IR light to another device or programmer 24. In some examples, data from at least one of optical perfusion sensor 76 or EGM sensing module 78 may be uploaded to a remote server, from which a clinician or another user may access the data to analyze the patient's condition. An example of a remote server is a server provided via the Medtronic CareLink® Network, available from Medtronic, Inc. of Minneapolis, Minn.

Figure 5:
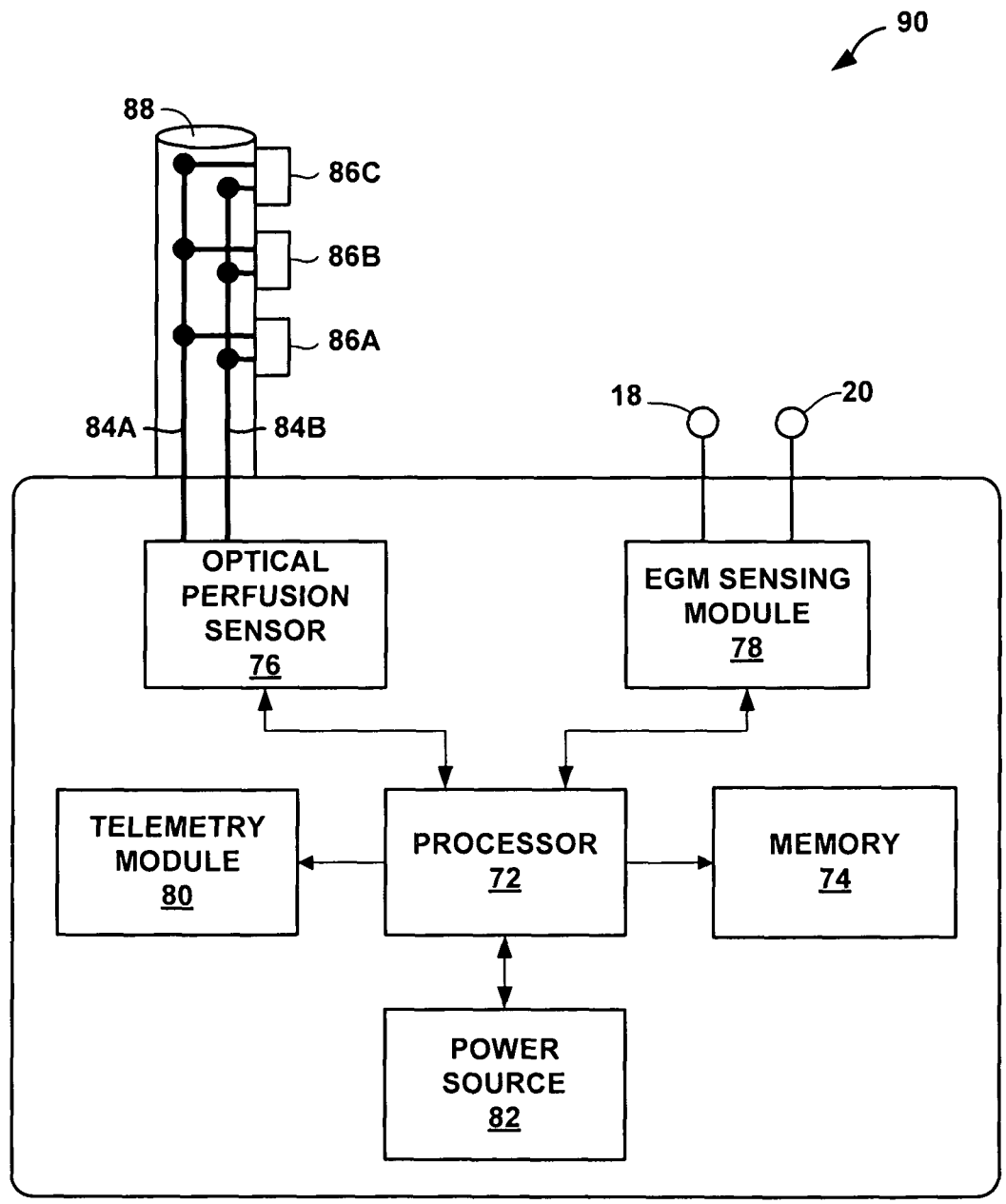
FIG. 5 is a block diagram illustrating another example implantable medical device that includes an optical perfusion sensor.

FIG. 5 is a block diagram illustrating another example implantable medical device 90 that includes an optical perfusion sensor 76. FIG. 5 illustrates a case of a plurality of sensor modules disposed outside of the housing of the IMD that are electrically coupled to the housing by a common lead or set of leads. IMD 90 includes many components that are substantially similar to those of IMD 70 shown in FIG. 4 and which have been numbered with identical reference numerals. Unlike IMD 70 shown in FIG. 4, sensor modules 86A-86C are deployed on lead 88 that extends, at least partially, outside of the housing of IMD 90. Lead 88 may contain elongated conductors 84A, 84B that together form a two-wire bus 84 to provide two-way communication between components within the housing of IMD 90 and sensor modules 86A-86C. In some examples, lead 88 may include multiple leads that extend from IMD 90 to sensor modules 86A-86C such that conductors 84A and 84B are contained within separate leads.

As illustrated in FIG. 5, sensor modules 86A-86C are oriented such that the windows emit and detect light on the same side of a tissue site. This allows the sensor modules to operate in a reflective mode where the detection sensor modules detect light that is reflected back from the tissue. In other examples, bus 84 may wrap around a tissue site such that the window of one sensor module 86A-86C faces the window of another sensor module 86A-86C with the tissue of interest residing between the windows. In such an example, the sensor modules may operate in a transmission mode where the light detector module detects light that is transmitted through the tissue site rather than just detecting light that is reflected by the tissue.

Although all of sensor modules 86A-86C are shown in FIG. 5 as located externally to IMD 90, in other examples, one or more of sensor modules 86A-86C may be located within or on the can of IMD 90. Hence, a combination of sensor modules 86A-86C may be deployed on or within the can as well as on one or more leads that extend from the can. FIG. 5 illustrates three sensors modules coupled to bus 84. However, any number of sensor modules may be used when performing optical perfusion measurements including a single sensor module. Bus 84 may be disposed within a lead containing protective shielding, and sensor modules 86A-86C may be formed on the lead and coupled to the bus.

Figure 6:
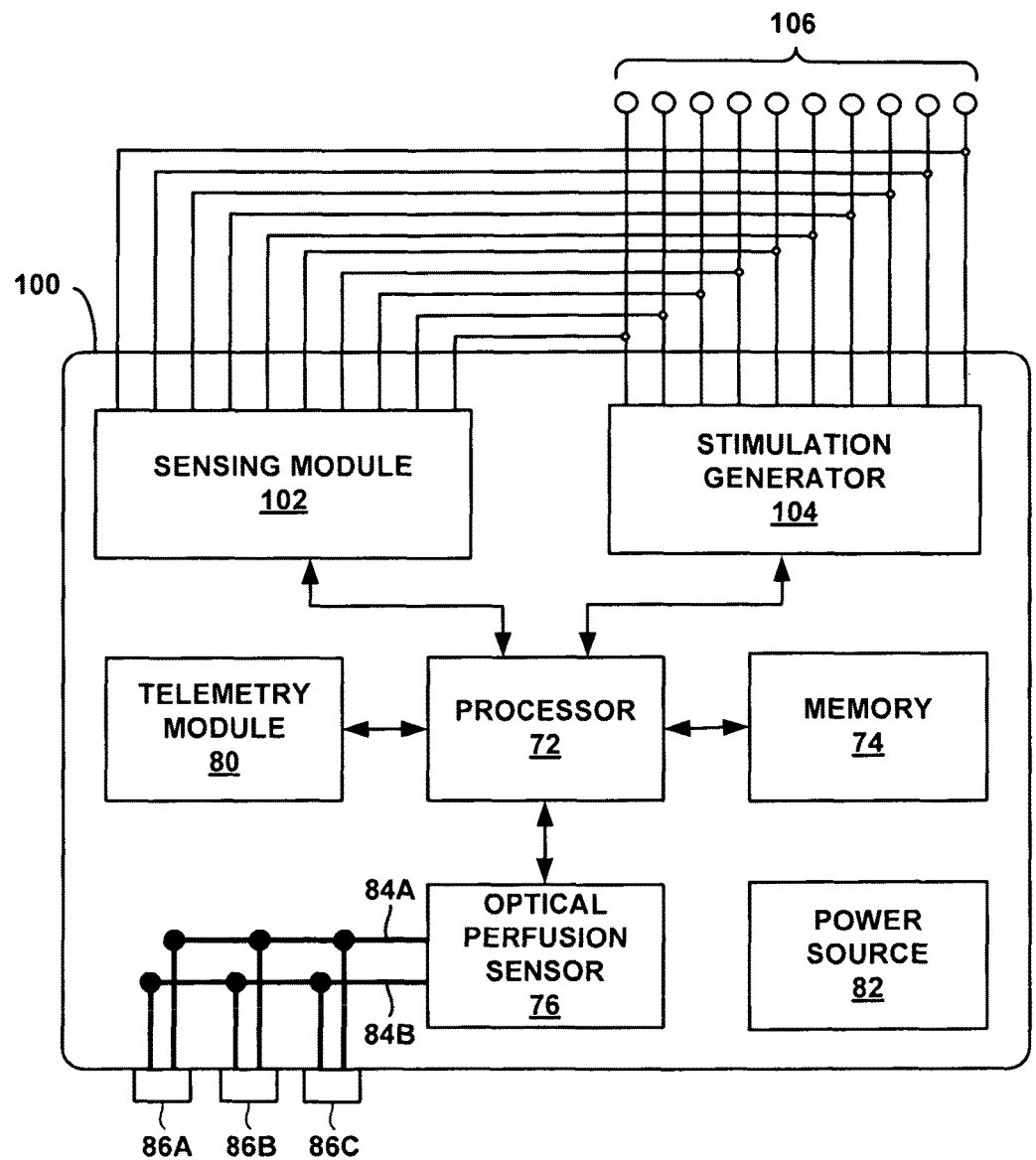
FIG. 6 is a block diagram illustrating an example implantable cardiac defibrillator that includes an optical perfusion sensor.

FIG. 6 is a block diagram illustrating an implantable cardiac defibrillator (ICD) 100. ICD 100 includes many components that are substantially similar to those of IMD 70 shown in FIG. 4 and which have been numbered with identical reference numerals. In addition, ICD 100 includes a sensing module 102 and a stimulation generator 104. Sensing module 102 and stimulation generator 104 are coupled to electrodes 106 via a plurality of leads. Electrodes 106 may be placed within the heart of a patient or located on the can of ICD 100. Sensing module 102 may use electrodes 106 to measure an EGM or ECG signal of a patient. Stimulation generator 104 may be configured to provide pacing pulses, cardiovesion shocks, or defibrillation shocks to a patient in response to one or more conditions.

In one example, sensing module 102 may sense that a patient is experiencing a ventricular fibrillation (VF) condition and notify processor 72. Processor 72 may then activate optical perfusion sensor 76 to make a tissue perfusion measurement. Optical perfusion sensor 76 may notify processor 72 of the results of the optical perfusion measurement. If the optical perfusion measurement indicates that it is likely that patient 12 is experiencing VF, then processor 72 may initiate additional therapy. In one example, processor 72 may initiate stimulation generator 104 to deliver a defibrillation shock to the heart of patient 12 when a fibrillation is detected and the optical perfusion measurement indicates a perfusion change or level that correlates with the fibrillation. On the other hand, if the optical perfusion measurements fail to corroborate that patient 12 is experiencing VF, then processor 72 may halt the delivery of potential therapy even though sensing module 102 indicated that a VF condition may be present. In this manner, optical perfusion sensor 76 provides additional information to processor 72 to use when evaluating whether to send a shock pulse to a patient.

Figure 7:
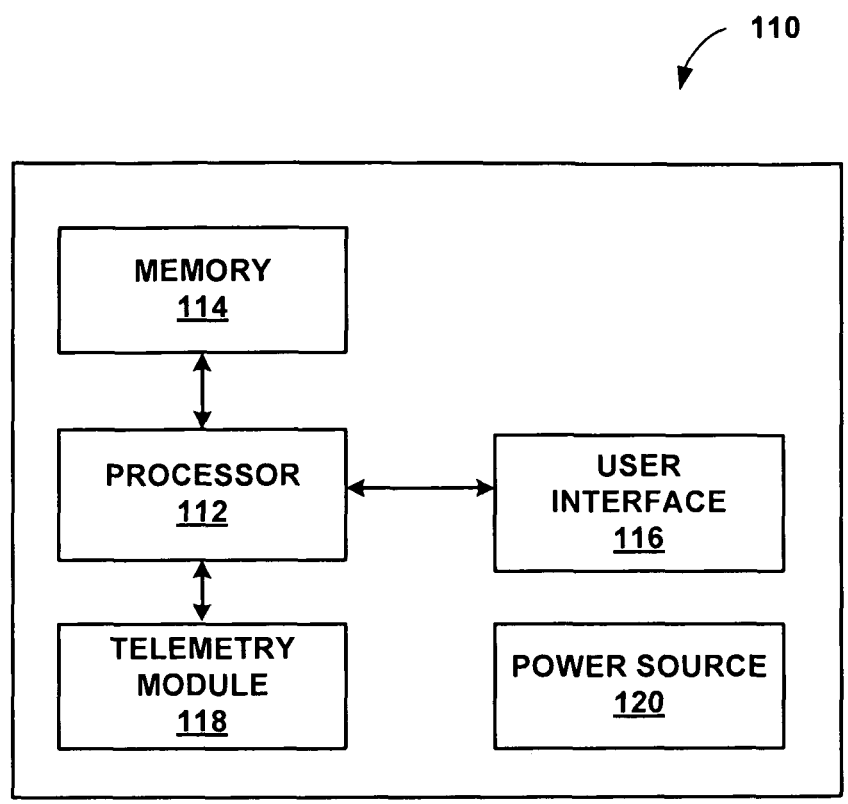
FIG. 7 is a block diagram of an example programmer for use within any of the systems of FIGS. 1-6.

FIG. 7 is a block diagram of an example programmer 110 for use within any of the systems 10, 40, or 50 of FIGS. 1-3. As shown in FIG. 7, programmer 110 includes processor 112, memory 114, user interface 116, telemetry module 118, and power source 120. Processor 112 may comprise one or more programmable processors. Programmer 110 may be a dedicated hardware device with dedicated software for programming of IMD 16 (FIGS. 1 and 2) and/or IMD 52 (FIG. 3). Alternatively, programmer 110 may be an off-the-shelf computing device running an application that enables programmer 110 to program IMD 16 and/or IMD 52.

A user may use programmer 110 to modify the optical perfusion and EGM sensing parameters of IMD 16 and/or IMD 52. For example, a user may use programmer 110 to configure a first sensor module to be a light source and a second sensor module to be a light detector. A user may also use programmer 110 to configure various calibration parameters, such as how long the light detector should measure the light during a single measurement, how much current should be used by the light sources, or what kind of resolution the results of the optical perfusion measurements should have.

In addition, the user may program the frequency at which EGM signals are sensed by EGM sensing module 78 (FIG. 4) or the minimum tissue perfusion sensing time window for sensing changes in tissue perfusion with optical perfusion sensor 26. A user may also use programmer 110 to select therapy programs (e.g., sets of stimulation parameters), generate new therapy programs, modify therapy programs through individual or global adjustments or transmit the new programs to a medical device, such as IMD 16 and/or IMD 52. The clinician may interact with programmer 110 via user interface 116, which may include a display to present graphical user interface to a user, and a keypad or another mechanism for receiving input from a user.

Processor 112 can take the form one or more microprocessors, DSPs, ASICs, FPGAs, programmable logic circuitry, or the like, and the functions attributed to processor 112 herein may be embodied as hardware, firmware, software or any combination thereof. Memory 114 may store instructions that cause processor 112 to provide the functionality ascribed to programmer 110 herein, and information used by processor 112 to provide the functionality ascribed to programmer 112 herein. Memory 114 may include any fixed or removable magnetic, optical, or electrical media, such as RAM, ROM, CD-ROM, hard or floppy magnetic disks, EEPROM, or the like. Memory 114 may also include a removable memory portion that may be used to provide memory updates or increases in memory capacities. A removable memory may also allow patient data to be easily transferred to another computing device, or to be removed before programmer 110 is used to program therapy for another patient. Memory 114 may also store information that controls therapy delivery by IMD 16 and/or IMD 52, such as stimulation parameter values.

Programmer 110 may communicate wirelessly with IMD 16 and/or IMD 52 by using radio frequency (RF) communication or proximal inductive interaction. This wireless communication is possible through the use of telemetry module 118, which may be coupled to an internal antenna or an external antenna. Telemetry module 118 may be similar to telemetry module 80 of IMDs 70, 90, or 100 (FIGS. 4-6).

Telemetry module 118 may also be configured to communicate with another computing device via wireless communication techniques, or direct communication through a wired connection. Examples of local wireless communication techniques that may be employed to facilitate communication between programmer 110 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 110 without needing to establish a secure wireless connection.

Power source 120 delivers operating power to the components of programmer 110. Power source 120 may include a battery and a power generation circuit to produce the operating power. In some examples, the battery may be rechargeable to allow extended operation. Recharging may be accomplished by electrically coupling power source 120 to a cradle or plug that is connected to an alternating current (AC) outlet. In addition or alternatively, recharging may be accomplished through proximal inductive interaction between an external charger and an inductive charging coil within programmer 110. In other examples, traditional batteries (e.g., nickel cadmium or lithium ion batteries) may be used. In addition, programmer 110 may be directly coupled to an alternating current outlet to power programmer 110. Power source 120 may include circuitry to monitor power remaining within a battery. In this manner, user interface 116 may provide a current battery level indicator or low battery level indicator when the battery needs to be replaced or recharged. In some cases, power source 120 may be capable of estimating the remaining time of operation using the current battery.

In one example, programmer 110 may receive diagnostic measurement or sensor detection data from IMD 16 via telemetry module 118. Programmer 110 may receive detection information related to heart sound sensing, tissue perfusion, EGM, and/or patient posture information as indicated by one or more of the sensor modules in IMD 16. In certain cases, programmer 110 may combine all of the received detection information into a single displayable report, which may be displayed to a user, such as clinician, via user interface 116. In one example, the displayable report may include detection information that is simultaneously displayed, such that the clinician may be able to identify and trends, correlations, or events that may of concern. The clinician may also determine to modify one or more stimulation programs after reviewing the report, in which case programmer 110 may be used to wirelessly communicate these modifications to IMD 16.

Figure 8:
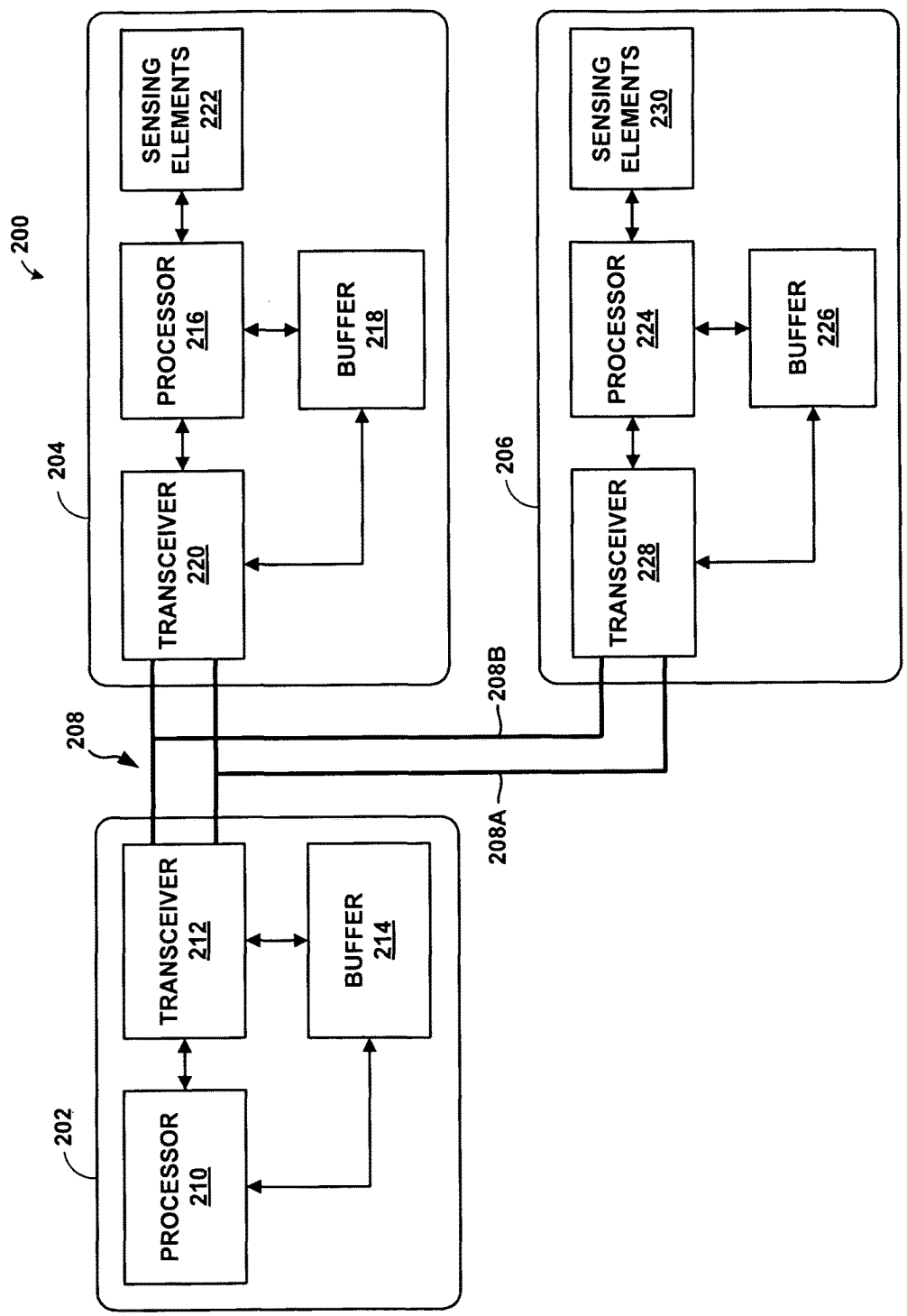
FIG. 8 is a block diagram illustrating an example sensing system that includes a plurality of implantable sensor modules.

FIG. 8 is a block diagram illustrating an example sensing system 200 that includes a plurality of implantable sensor modules. Sensing system 200 may be used to implement any of the optical perfusion sensors described in this disclosure. In addition, sensing system 200 may be used to implement any other sensing system that requires one or more implantable sensor modules. For example, sensing system 200 may be used to implement a sonomicrometry sensing system or pressure sensing system. Sensing system 200 may include a host controller 202, sensor modules 204, 206, and two-wire bus 208, comprising wires 208A and 208B. Host controller 202 and sensor modules 204, 206 are all electrically coupled to two-wire bus 208 via one or more ports. The two-wire bus 208 may extend within an IMD housing, within an elongated lead, or both to permit two-way communication between host controller 202 and sensor modules 204, 206.

In some examples, two-wire bus 208 may be contained in a lead that extends from an implantable medical device into the heart. In other examples, two-wire bus 208 may be contained in a lead that extends from an implantable medical device to a tissue site proximate to where the measurements, such as tissue perfusion measurements or blood oxygen content measurements, can be made. In further examples, two-wire bus 208 and one or more sensor modules 204, 206 may be located in the can of an implantable medical device. In such examples, one or more sensor modules may be positioned on the outer housing to obtain measurements at a tissue site surrounding the can. Although system 200 illustrates two sensor modules 204, 206, any number of sensor modules may be used to perform the same or different sensor actions.

Host controller 202 is a master device that drives signals on bus 208 in order to control the timing of sensor actions across the sensor modules when system 200 is making a measurement. Host controller 202 may include a processor 210, a transceiver 212, and a buffer 214. Host controller 202 may be incorporated into any of the implantable medical devices of FIGS. 1-3 or within optical perfusion sensor 76 shown in FIGS. 4-6.

Processor 210 is capable of controlling all aspects of host controller 202 including the timing coordination of the sensor modules 204, 206 when performing measurements. Processor 210 may control transceiver 212 to transmit commands over bus 208 to the sensor modules 204, 206, and to receive messages from sensor modules 204, 206 over bus 208. The commands may be transmitted according to a bus communications protocol described herein. Processor 210 may transmit triggering commands in order to arm one more of sensor modules 204, 206 for an upcoming measurement. Processor 210 may also transmit Read Result commands to obtain the results of one or more measurements from a sensor module. In addition, processor 210 may transmit a Write command to sensor modules 204, 206 in order to configure parameters or other features of sensor modules 204, 206. Processor 210 may also transmit power pulses to sensor module 204, 206 in order to power the sensor modules and/or provide timing information to sensor modules 204, 206.

Processor 210 is capable of performing pre-processing and post-processing of sensor data as needed for a measurement. Processor 210 may retrieve data from buffer 214 that has been received from a sensor module over bus 208 and perform a post-processing algorithm on the data, such as digital filtering, or analog-to-digital conversion. Processor 210 may also store data to be transmitted to sensor modules 204, 206 in buffer 214. Processor 210 may comprise one or more programmable processors each capable of performing all of a subset of the functions described herein.

Processor 210 may configure sensor modules 204, 206 to perform one or more sensor actions according to an operating mode. For example, processor 210 may configure sensor module 204 to perform a first sensor action, and sensor module 206 to perform a second sensor action. Both the first sensor action and the second sensor action may need to occur in a particular order to obtain valid results for the measurement. Processor 210 may then transmit a signal over bus 210 to control sensor modules 204, 206 such that the first sensor action is performed at a time prior to the second sensor action. In this manner, processor 210 controls the timing for performance of sensor actions across the sensor modules when system 200 is making a measurement.

In one example, the signal transmitted by host controller 202 over bus 208 may be a power pulse signal. A power pulse signal may be a monophasic power pulse signal or biphasic power pulse signal. A monophasic power pulse signal may refer to a signal that has substantially periodic pulses in either the positive or the negative direction, but not in both directions. A biphasic power pulse signal may refer to a signal that has substantially periodic pulses where the pulses alternate in the positive and negative direction. For example, the first pulse may be a positive pulse, the second pulse may be a negative pulse, and the third pulse may be a positive pulse. The magnitude of the positive pulses may be in the range of about 2.4 Volts to about 3.4 Volts, and preferably at a magnitude of about 2.8 Volts. Likewise the magnitude of the negative pulses may be in the range of about −3.4 Volts to about −2.4 Volts, and preferably at a magnitude of about −2.8 Volts.

In examples where system 200 performs optical perfusion measurements, processor 210 may transmit power pulses over bus 208 to control the timing for performance of light emission and light detection. For example, processor 210 may control the timing of sensor modules 204, 206 such that a light emitter sensor module begins to emit light at a time prior to when a light detector sensor module begins to detect or measure light. As another example, processor 210 may control the timing of sensor modules 204, 206 such that a light detector sensor module ceases to detect or measure light at a time prior to when a light emitter sensor module ceases to emit light. In this manner, processor 210 coordinates the timing for performance of the actions across sensor modules 204, 206 to ensure that the light emitter and the light detector are activated and deactivated (i.e. "turned on" and "turned off") in the proper order. This ensures that the light is always being emitted when detection is taking place.

Processor 210 may also control the sensor modules 204, 206 to perform multiple measurements according to a pipelined execution scheme. According to one aspect of the pipelined execution scheme, processor 210 may configure sensor module 204 to perform a first sensor action and a second sensor action, both of which may need to occur in a particular order to obtain a valid result for a measurement. In this example, the first sensor action may need to be performed prior to the second sensor action. Processor 210 may control the timing for performance of the sensor actions such that a time period for performance of the second sensor action for a previous measurement overlaps, at least partially, with a time period for performance of the first sensor action for a subsequent measurement. By overlapping or pipelining the performance of different sensor actions for each measurement, processor 210 is able to reduce the overall time required for multiple measurements.

According to another aspect of the pipelined execution scheme, processor 210 may transmit a first signal over bus 208 to coordinate timing of sensor actions for making a first measurement and transmit a second signal over bus 208 to coordinate timing of sensor actions for making a second measurement prior to receiving results from the first measurement at host controller 202. Under this scheme, processor 210 transmits the second signal to coordinate timing for the second measurement over bus 208 during a time period that overlaps, at least partially, with a time period for performing a sensor action for the first measurement. The results of the multiple measurements may be transmitted from sensor module 208 to host controller 202 as a single packet at a later time.

Transceiver 212 provides a communication interface between commands issued by processor 210 and the physical data transmission layer of bus 208. In addition, transceiver 212 sends power pulses to sensor modules 204, 206 in order to supply power to sensor modules 204, 206. Transceiver 212 may also send a synchronizing signal or clock signal to sensor modules 204, 206. Transceiver 212 may be electrically coupled to processor 210 and buffer 214. In general, transceiver 212 may receive commands from processor 210, decode the commands, and convert the decoded commands into voltages to transmit over bus 208 according to the bus communications protocol described herein. Transceiver 212 may also receive data from sensor modules 204, 206 in the form of voltages transmitted over bus 208. Transceiver 212 may decode the received data, convert the data into a digital value, and store the data in buffer 214. Transceiver 212 may include a six-phase clock in order to accurately control the voltage swings over the bus during a bit time. Transceiver 212 may also include a power supply and one or more comparators for generating the data and power pulse signals over bus 208. Transceiver 212 has the capability to pull-up bus 208 to a high voltage and to pull-down bus 208 to a low voltage. As will be described later in this disclosure, the timing of the high and low voltages during a bit time determines whether a logic "0" or logic "1" is transmitted over bus 208.

Buffer 214 is a memory that may store outgoing data prior to transmission over bus 208 as well as incoming data received over bus 208. Buffer may include any volatile storage medium, such as a random access memory (RAM).

Sensor modules 204, 206 are capable of communicating with host controller 202 via bus 208, and of performing one or more sensor actions. Sensor modules 204, 206 are configured to receive a signal from host controller 202 over bus 208, and to coordinate timing for performance of sensor actions across the sensor modules 204, 206 based on the received signal in order to make a measurement. Sensor module 204, 206 include processors 216, 224, buffers 218, 226, transceivers 220, 228, and sensing elements 222, 230. Processors 216, 224 may each comprise one or more programmable processors that are capable of performing all of a subset of the functions described herein.

In general, transceivers 220, 228 and buffers 218, 226 operate in a manner similar to transceiver 212 and buffer 214 of host controller 202. However, in some examples, transceivers 220, 228 may not have the capability to pull-up bus 208 to a high voltage, but only the capability to pull-down bus 208 to a low voltage. This reduces the amount of power dissipated by sensor modules 204, 206 when communicating over bus 208. Unlike the transceiver in host controller 202, transceivers 220, 228 may also have the capability to rectify power pulses received over bus 208 and store the energy from the rectified pulses in order to provide temporary power for sensor modules 204, 206. In some examples, sensor modules 204, 206 may have an internal power supply.

Processors 216, 224 control the performance of sensor actions within sensor modules 204, 206 respectively. Processors 216, 224 may cause sensor modules 204, 206 to perform sensor actions in response to a signal received from host controller 202. As one example, processor 216 may analyze the signal received from host controller 202, and detect a first signal condition. Processor 216 may then cause sensor module 204 to perform a first sensor action in response to detecting the first signal condition in the received signal. Processor 224 may also analyze the signal received from host controller 202, and detect a second signal condition. Processor 224 may then cause sensor module 206 to perform a second sensor action in response to detecting the second signal condition in the received signal. The first and second signal conditions may be defined such that the first signal condition occurs within the received signal prior to or simultaneously with the second signal condition.

When power pulses signals are used, the first signal condition may be the reception of a first number of power pulses, and the second signal condition may be the reception of a second number of power pulses. The second number may be greater than the first number. In some examples, the reception of a particular number of power pulses may be the reception of a particular number of power pulses during a set time period. Processor 216 may determine when the first signal condition occurs by counting the number of pulses received by transceiver 220. Likewise, processor 224 may determine when the second signal condition occurs by counting the number of pulses received by transceiver 220. When the number of pulses received is greater than or equal to a signal condition, then that signal condition has occurred, and processor 216 or 224 may initiate the performance of the corresponding sensor action. In one example, processors 216, 224 may count the number of power pulses by counting the number of power pulse edges. In particular, processor 216, 224 may count the number of rising edges, the number of falling edges, or the combined number of rising and falling edges.

The performance of a sensor action may include, for example, activating or deactivating one or more sensor elements. The performance of a sensor action may also include taking a measurement and/or storing results of a measurement within a buffer (218, 226) of the sensor module. As another example, the performance of a sensor action may also include performing analog-to-digital conversion on a sensor measurement received from a sensing element. In addition, the performance of a sensor action may include transmitting results from one or more measurements from a sensor module to the host controller. The techniques described in this disclosure are not limited to any particular type of sensor action and may include any action performed by a sensor module that assists the host controller in making a measurement.

Processors 216, 224 may also control the timing for performance of multiple sensor actions within the same sensor module based on the signal received from host controller 202. For example, processor 216 may cause sensor module 204 to perform a first sensing action when a first signal condition is detected and to perform a second sensing action when a second signal condition is detected. The first sensor action and the second sensor action may need to occur in a particular order in order to obtain valid results for the measurement.

Processors 216, 224 may also control the activation and deactivation of sensing elements 222. As one example, sensing elements 222 may include a light emitting diode (LED) and a photodiode integrator. In this example, processor 216 may control when the light emitting diode generates light and when the light emitting diode ceases to generate light. Processor 216 may also control when the photodiode integrator begins to integrate received light and when the photodiode integrator ceases to integrate the received light. As another example, sensing elements 222 may include sonomicrometry sensing elements that include an acoustic ping generator and an acoustic detector. Processor 216 may control when the acoustic ping generator generates an acoustic ping and when the detector begins or stops detecting the acoustic ping. Other example sensor elements include pressure sensors, temperature sensors, optical sensors, sound sensors, and the like.

Processors 216, 224 may cause the results of one or more measurements to be stored in buffers 218, 226 respectively. Processors 216, 224 may then cause transceivers 220, 228, respectively, to transmit the results of multiple sensor measurements to host controller 202 in a single packet. The transmission of the results may be in response to a Read Results command issued by the host controller.

Processors 216, 224 may also contain registers that store one or more operational and/or configuration parameters associated with sensor modules 204, 206 respectively. For example, the registers may store configuration parameters for the operating mode of the sensor module as well as operational parameters for particular sensing elements 222, 230. Example operational parameters include LED supply current parameters, photo-integrator gain parameters, and integration time parameters. In additional examples, the registers may store addressing information such a short address used by host controller 202 to address the sensor module. In some examples, the operational and/or configuration parameters may not be stored in registers contained in processors 216, 224, but rather, the parameters may be stored in a memory external to processors 216, 224. In one example, the operational and/or configuration parameters may be stored in the form of an electrically-erasable programmable ROM (EEPROM). The EEPROM may also store a unique long sensor address and a serial number. In any case, host processor 202 may configure sensor modules 204, 206 by transmitting Write commands and/or Triggering commands to sensor modules 204, 206, which may cause certain data values to be written as operational and/or configuration parameters to the registers or external memory.

Each of sensor modules 204, 206 may also include a power recovery unit and a clock recovery unit (not shown). The power recovery unit collects the energy from the fluctuating voltages on two-wire bus 208 in order to power the sensor module. The clock recovery unit may be periodically synchronized with the clock of host controller 202. Host controller 202 thereby controls the sampling rate and sampling time for each of the individual sensors by way of transmitting commands to the sensor modules, and triggering the sensor modules to sample. Because host controller 202 also controls when each sensor puts each bit of data on the bus, the need for high accuracy clock generation circuits within each sensor module is therefore eliminated. A protection network may also be included in each of the sensor modules 204, 206 to minimize the effect of transient voltages and currents induced on the two-wire bus 208 due to electro-surgery, implantable cardio defibrillator ("ICD") discharge, defibrillation, electro-static discharge, and electromagnetic interference, and the like.

Two-wire bus 208 provides a physical communication infrastructure between host controller 202 and sensor modules 204, 206. Communication over two-wire bus 208 takes place as a serial bit stream. That is, only one data bit may be transmitted over the bus per bit time. A first wire 208A of 2-wire bus may be a data wire while the second wire 208B of the bus may be a shield wire. In one example, when the sensor modules are configured to perform tissue perfusion measurements, the second wire of the two-wire bus may be electrically coupled to a ground voltage. In another example, when the sensor modules are configured to perform a blood oxygen level measurement, the second wire of the two-wire bus may be connected to a shield conductor. In some cases, the two-wire bus may be supplemented by a third wire that, when referenced with the ground/shield wire of the bus, provides a dedicated power supply to sensor modules 204, 206. In other cases, power, data, and timing information may be time-multiplexed on only two-wires without the need for a third wire. In any case, a single two-wire bus is capable of providing timing coordination of multiple sensor actions across one or more sensor modules for performing various sensor measurements within implantable system 200. Two-wire bus 208 may be made from two conductors that are separated by an insulator. Several examples of various two-wire bus implementations are described below.

Two-wire 208 bus may be implemented in the form of co-axial lead. In such a case, an outer conductor and an inner conductor may be electrically coupled between sensor modules 204, 206 and host controller 202. The outer conductor may be electrically connected to the ground terminal of host controller 202. The inner conductor may be electrically connected to a communication port of host controller 202 and a communication port of sensor modules 204, 206. A stylet may be insertable within the inner conductor to aid in positioning the sensor at the time of input. The outer conductor may be covered both interiorly and exteriorly by an outer conductor insulation layer. The inner conductor may be covered exteriorly by inner conductor insulation layer. A gap may be formed between inner conductor insulation layer and outer conductor insulation layer. The gap may be an air gap if the lead is dry or may gradually fill with fluid if the lead is wet. In addition, a bus insulation layer may surround and protect both the inner conductor and the outer conductor.

As one example, the insulation layers may be made from polyurethane (Pellathane 80A). The insulation layers may also be made from a biocompatible insulating material including polyurethanes, ETFE, silicone, or polyamides. Insulating materials with low dielectric coefficients are preferred to minimize capacitance between conductors. The gaps between the insulation and conductors will be air when the lead is dry or may gradually fill with water when the lead is wet. The outer and inner conductors can be made from biocompatible conductive materials including MP35N, platinum, or silver cored MP35N. Conductive materials with low resistance are preferred.

Two-wire bus 208 may also be implemented in the form of a multi-lumen lead. For example, a three lumen high voltage lead intended for an implantable cardio-defibrillator ("ICD") and pressure sensing application may be used to facilitate the two-wire bus. The lead may support integrated bipolar sensing and a high voltage RV coil. The lead may use a coaxial cable for communication with a pressure sensor, an oxygen sensor, and/or a combination of sensors. The lead may include a plurality of compression lumens defined within the lead body. The lead may also include three electrically isolated portions. The first portion may contain a cable within a conductive coil, which may serve as two-wire bus 208. The cable may be used for sensor communication and is preferably silver cored MP35N with an ETFE insulating layer. The second portion may contain a conductive coil for a tip electrode, and may be configured to allow a stylet to pass through to the tip. The third portion may contain a cable for a high-voltage (HV) coil used to deliver shock treatment. The conductors preferably have low resistance (e.g. <<5 ohms).

Two-wire bus 208 may also be implemented in the form of a co-radial lead that uses a co-radial, multi-conductor construction. Such a lead uses four individual wires wound side by side. Two adjacent wires are connected to a first signal and may form the first wire 208A of two-wire bus 208. The other two adjacent wires are connected to a second signal and may form the second wire 208B of two-wire bus 208. An outer insulation of polyurethane is used to provide further protection. The wires are wound together with two wires used for each signal. Polyurethane tubing may be used to cover each of wires. In addition, each wire may be further insulated with outer insulation ETFE. Each of the implementations for the two-wire bus described above are merely exemplary, and any other implementation that has two conductors separated by an insulator may be used to practice the techniques described in this disclosure.

Host controller 202 may communicate to sensor modules 204, 206 over 2-wire bus 208 via a bus communications protocol. The communications protocol includes triggering commands, which initiate measurements and arm the sensor modules. The communications protocol may also include reading and writing commands, which allow host controller 202 to read and write data to sensor modules 204, 206. The communications protocol further includes signals that transfer power from host controller 202 to sensor modules 204, 206. In addition, the communications protocol includes signals that coordinate the timing for the performance of sensor actions across sensor modules 204, 206 when system 200 is making a measurement. In some case the signals that coordinate the timing may also supply power to sensor modules 204, 206. The bus communications protocol described herein allows data, power, and timing information to be transmitted over two conductors. This is accomplished by time-multiplexing transmission of data over bus 208 with the transmission of power and timing information. In some examples, power may be supplied to sensor module 204, 206 by a dedicated third wire that is referenced to the existing ground wire of bus 208.

In general, the start of a data bit begins with host controller 202 pulling the data wire 208A of two-wire bus 208 up to a high voltage with reference to shield/ground wire 208B. A fraction of a bit time later, the master pulls data wire 208A down to a low voltage with reference to shield/ground wire 208B. The duration of the high voltage pulse determines the data value. As one example, the voltage swing between a high voltage and low voltage over two-wire bus 208 may be approximately 200 mV. In some examples, host controller 202 may be the only device coupled to two-wire bus 208 with pull-up capability. In other examples, sensor modules 204, 206 may also have the capability to pull-up bus 208 to a high voltage. Such a capability may be supplied by an internal power source within sensor modules 204, 206 or by collecting power from the signals that are transferred from host controller 202 to the sensor modules 204, 206.

The basic time unit for communication between the host controller 202 and sensor modules 204, 206 may be referred to as a bit time. A bit time may be composed of six clock cycles. In one example, the bit time may be 10 microseconds (μs) resulting in a bit rate of 100 kHz. The sending of a data bit from host controller 202 to sensor modules 204, 206 is first described. At the beginning of a bit time, host controller 202 may pull bus 208 up to a high voltage. A fraction of a bit time later, host controller 202 may pull bus 208 back down to a low voltage. The duration of the high voltage pulse indicates the data value. For example, if the voltage level on bus 208 is high for approximately one-third of the bit time, then the data value corresponds to a logic "0." On the other hand, if the voltage level on the bus is high for approximately two-thirds of the bit time, then the data value corresponds to a logic "1." At the end of a bit time, host controller 202 pulls up the bus to a high voltage level to begin a subsequent bit time.

The sending of a data bit from a sensor module 204 to host controller 202 is now described for examples where the sensor modules do not have pull-up capability. In such a case, the sensor modules only have the capability to pull the bus down. At the beginning of every bit time, host controller 202 pulls the bus to a high voltage level. Then, the sensor module 204 uses timing information to pull the bus down to a low voltage level. For example, if the sensor module pulls the bus down to a low voltage level at approximately one-third of the bit time, then the transmitted data value corresponds to a logic "0." Likewise, if the sensor module pulls the bus down to a low voltage level at approximately two-thirds of a bit time, then the transmitted data value corresponds to a logic "1." Thus, the resulting waveforms for data transmission by the sensor modules over the bus appear substantially similar to the waveforms for data transmission by the host controller over the bus. The difference is that the host controller drives the bus when transmitting data to the sensor modules, and both the host controller and sensor modules share the driving of the bus when transmitting data from the sensor modules to the host controller.

Host controller 202 may control when one or more sensor modules 204, 206 make a measurement by issuing trigger commands, which control the timing of sensor measurements. This allows the volume of the sensor modules to be reduced as they do not need to have a controlled time base, such as a crystal. In addition, issuing triggering commands can ensure that all sensor modules are sampling at the same time or at the same multiples of time. In other words, issuing triggering commands allows for data sampling alignment between different sensor modules. Moreover, the issuing of triggering commands by the host controller allows the master to control the data rates across the sensor modules.

The host controller is capable of issuing three different types triggering commands, namely a Long Trigger (LTRIG), a Quick Trigger (QTRIG), and a Power Pulse Trigger. The individual sensor modules may support one or more of these types of triggering commands. The Long Trigger and Quick Trigger commands may not cause the sensor modules to immediately begin performing sensor actions, but rather these commands may arm the sensor modules for another command or for a power pulse burst, which will control the timing for the actual measurement. The sensor modules may then begin performing sensor actions in response to receiving a certain number of power pulses. The triggering commands may also notify the sensor modules as to what type of sensor modules as to what type of measurement is going to be made.

The Long Trigger command can be used to trigger the sampling of data from one or more sensor modules. The Long Trigger command may include a start sequence, a sensor module address field, a Quick Trigger field, a master command name field, a data field, a stop sequence, and a frame checking sequence. The start sequence may be two to three bit lengths in duration. In one example, the start sequence may be a logic "0" on the bus for a first bit time followed by a logic "1" over the bus for two subsequent bit times. Prior to the start sequence, a power pulse may be sent to the sensor modules to cause the sensor modules to "wake up" and begin to listen for the start sequence. The start sequence allows the sensors to determine whether they should continue to listen for a command. In cases where the sensor modules receive a power pulse but no start sequence, the sensor modules may go back to sleep. When a sensor module is sleeping, it does not need to store data for the command. Thus, only a small amount of circuitry needs to be used to wait for another command.

When the sensor modules detect a start sequence, they continue to listen to the bus to determine which sensor modules are being addressed. The sensor module address field provides this information. In one example, the address field may be six bit lengths long, and the system may contain up to sixteen individually addressable sensor modules. The six bits allow for individual addressing of sensor modules as well as for addressing multiple sensor module (i.e. multicasting) and addressing of all of the sensor modules (i.e. broadcasting). If a sensor module receives the sensor module address field and determines that it is not being addressed, it may go back to sleep until the next start sequence. On the contrary, if a sensor module determines that the address field is being addressed to that particular sensor module, then the sensor module will continue to listen to the subsequent portion of the command.

The Quick Trigger bit identifies whether the signal is a Long Trigger (LTRIG) command or a Quick Trigger (QTRIG) command. When the Quick Trigger bit is set, the command is a Quick Trigger command. Otherwise, if the Quick Trigger bit is not set, the command is a Long Trigger command. A Quick Trigger command is similar to a Long Trigger command except that the Quick Trigger command does not contain a master command name field and the data field has a reduced number of bits. For example, the data field in a Long Trigger command may have eight bits while the data field in a Quick Trigger command may have four bits. Because the Quick Trigger command does not contain these fields, multiple measurements may be able to be performed at a faster rate because the command transmission overhead for each of the measurements is reduced.

The master command name field determines what type of command is being transmitted to the sensor modules. In one example, the master command name contains five bits and the Long Trigger command takes on the value of 03hex. Again, the Quick Trigger command does not contain a master command name field. Instead, when the Quick Trigger bit is set, the sensor modules already will determine that the command is a Quick Trigger command. The Quick Trigger bit may add an additional bit of overhead to the overall command word length, but such a feature results in shorter command word lengths for the Quick Trigger command. When the Quick Trigger command is frequently used, this can provide substantial savings in command latency and improve the rate at which multiple measurements can be taken. In addition, because the Quick Trigger command has fewer bits than the Long Trigger command, substantial power savings may be achieved within the sensing system.

The data field is definable for each individual sensor module. A single sensor module may have multiple individual sensors to perform various types of measurements. For example, an optical sensor module may perform red wavelength measurements, infrared wavelength measurements, isobestic wavelength measurements, and ambient light wavelength measurements. The data field may contain a command code, which instructs the sensor module to perform a particular type of measurement. In the case of an optical sensor module, the command code may instruct the sensor module to measure a particular wavelength of light, or to measure ambient light.

The count code field is a code that gives a sequence to the measurement triggers that are being sent to the sensor modules. In one example, the count code field may be four bits, and the host controller may produce the following sequence of count values (in hexadecimal): 0, 1, 2, 3, 4, 5, 6, 7, 8, 9, A, B, C, D, 0, 1, 2, 3, etc. In this example, the hexadecimal values of E and F (i.e. 1110 and 1111) are not used during the ordinary counting sequence, but in other examples these values may be used. In this example, the count code of hexadecimal F is a reserved count code for cleared data, and the count code of hexadecimal E is a reserved count code for retriggering of a sample that was not received at the host controller after a read results command.

The count code allows the host controller to determine if a sensor module missed one or more triggers and which triggers were missed. The count code can be retrieved by a Read or Read Results command. Since commands can be multicast or broadcast and have multiple sensors acknowledge the command, a count value embedded in the sensor's return data may be useful for the master in order to determine if the sensor module actually received the triggering command and performed a measurement.

Count codes allow both the host controller and the sensor modules to determine if a trigger was missed. For example, if a sensor module is sampling on every count, then the count code should increment by a single value for every measurement and loop back to zero at the highest count code value. Count values can be used for signal processing either within the sensor module or host controller. As such, slopes can be calculated, even with missing triggers, because the count value is given for each trigger.

Time alignment of data between sensor modules, however, is accomplished by the host controller appropriately modifying the sensor module address field. For example, a sensor module can be instructed to down sample on even count values or odd count values of the count code field via the sensor module address field. If the identity of the sensor module is indicated in the address field, the sensor module will perform a measurement. Otherwise, the sensor module will not perform a measurement. As such, the count code does not dictate if a sample occurs. When data is read from the sensor module via a Read Results command, the count code indicates whether any data is missing.

In the case of the optical sensor module, the Quick Trigger command data field may only contain the command code while the Long Trigger command may contain count codes as well as command codes. Such a configuration allows the host controller 202 to configure one or more of the sensor modules 204, 206 to perform a particular measurement by using Quick Trigger commands. After the sensor modules are configured to perform various sensor actions, the host controller 202 may coordinate the timing of for performance of measurements by using the Quick Trigger command followed by a series of power pulses. The sensor module address field in the Quick Trigger command may be used to selectively enable or disable particular sensor modules 204, 206 for a given measurement.

When host controller 202 is transmitting data, the stop sequence indicates the end of a command to the sensor module. When the sensor modules 204, 206 are transmitting data, the stop sequence is used to tell the host controller that this is the end of the data. In one example, the stop sequence may take on the form of Stop-Ack Req-(N)Ack. The "Stop" portion of the stop sequence means that the host controller will hold the bus high continuously for one bit time. During the "Ack Req" portion of the stop sequence, the transmitter will transmit a logic "0" for one bit time. "Ack Req" means Acknowledge Request. That is, the transmitting device is asking one or more of the listening devices if they successfully received the message. Then, the receiving device will respond by transmitting a logic "0" or failing to transmit anything at all. The term "Ack" means Acknowledge, and occurs when the receiving device transmits a logic zero. The term "(N)Ack" means Not Acknowledge, and occurs when the receiving device fails to transmit a logic zero. In some examples, the receiving device may transmit two different acknowledgement bits during two different bit times. The first acknowledgement bit may indicate whether the CRC check (i.e. error checking) was successful. The second acknowledgement may indicate whether the sensor module has sufficient power or whether the sensor module needs additional power. After the acknowledgements have been transmitted, the transmitting device may hold the bus high for one bit time to indicate the end of the Acknowledge sequence. In cases where the command transmitted by the host controller is a Read command or a Read Results command, the sensor module may begin transmitting data to the host controller immediately after the second acknowledgement without the additional stop bit being transmitted that indicates the end of an Acknowledge sequence.

The frame check sequence provides error checking for the system. In one example, the frame check sequence includes an eight bit cyclic redundancy check (CRC) code. The CRC code may be based upon a generating polynomial. When a receiving device receives a command or data, it may calculate a CRC code based on the received data. If the CRC code does not match the CRC code received in the message, then the receiving device may request retransmission of the message.

Power pulses may also be used to trigger measurements in cases where the sensor modules 204, 206 repeat the same measurement and do not need to be reconfigured between measurements. Power pulse triggering may also provide power to the sensor modules. When triggering with power pulses, the host controller first performs a write operation to a register within the sensor module to arm the sensor. The write operation may set a single bit within the register. Then, power pulses may be sent to the sensor modules. Any sensor modules that have been armed will make measurements based on the power pulses. Power pulse triggering uses no data bits so it burns the least amount of power and reduces protocol overhead.

A sensor module may have a long address and a short address. The long address may specify who made the sensor module, the protocol version of the sensor module, the model number of the sensor module, the unique serial number of the sensor module, where the sensor module was made, and a sensor module location number. The sensor module location number may be used to identify where sensor module is located within a sensing system. For example, the location number may specify where the sensor module is on a lead or whether the sensor module is located on the can of an implantable medical device and where on the can the sensor module is located.

The long address provides an address format for uniquely identifying a sensor module and various characteristics about the sensor module. During normal operation, however, broadcasting this data over the bus every time a sensor needs to be addressed would cause a large number of unnecessary bits to be transmitted over the bus. Accordingly, the communication protocol provides that the host controller may assign a short address to each of the sensor modules by using a Write Short Address command. The Write Short Address command basically associates a short address to a long address within the sensing system. The short address may then be used in the sensor module address field in other commands, such as the Long Trigger commands and the Quick Trigger commands.

After a measurement has been triggered by one of the triggering commands, one or more sensor modules may perform a measurement and store the results of the measurement within a buffer of the sensor module. The contents of the buffer may be retrieved by the host controller by means of a Read Results command. The Read Results command retrieves result data from the buffers within the sensor modules. The buffers may be RAM or Register Address space. The results from a measurement are usually stored within the buffer by the analog-to-digital converter within the sensor module. Data can be put into buffer in any format and the format can be specific for a particular type of sensor module. For example, the data format for one sensor module may store the oldest data at the beginning of the buffer space.

The Read Results command works in close association with the Long Trigger and the Quick Trigger commands. The Long Trigger command may forward a command code and a count code to the sensor modules when performing measurements. These command codes and count codes may be stored with the corresponding measured data within the buffer for the sensor module. The Quick Trigger command works in a similar fashion, but it does not forward a count code to the sensor modules as part of the command. Hence, the sensor module may not necessarily store the count code with the associated measured data in the buffer. However, in some examples, the sensor module may be configured to store the command code that was received in the most recent Long Trigger command with every data point stored in the buffer.

The sensor modules may contain two buffers with one buffer being used to read data while the other buffer is having data written to it by the ADC. The Read Results is setup to read from a specific buffer (either "0" or "1") within the sensor module. Depending on which buffer the ADC pointer is pointing to, the appropriate buffer is used. In one example, the sensor modules may contain two read results buffers each of 256 bits in length. The 256 bits may be partitioned into 16 data words of 16 bits each. 14 bits of the data word contain the result of the analog-to-digital conversion and the remaining two bits may indicate the measurement type. The measurement type may be encoded as binary 00=Ambient, binary 01=Red, binary 10=Isobestic, and binary 11=Infrared.

The buffers within the sensor modules may have pointers which automatically move to the next address of unread data in response to a Read Result Command. As such, the command need not have an address field besides a single bit indicating the buffer for reading. The buffers within the sensor modules may also have the capability of automatic "ping-ponging." In other words, one buffer is written, while the other buffer is read. The Read Results command offers the possibility to perform retries of the reading operation when the prior reading operation was unsuccessful. In addition, the data stored within the buffers may contain other information such as the associated command code, count code, other status data or CRCs embedded within the data.

The Read Results command allows the sensor modules to package data from several measurements into a single packet and to transmit the packet over the bus in a single bus transfer. This reduces bus traffic and in turn reduces power. By storing multiple measurements within the sensor module, it also allows individual measurements to be made closer together in time. This is important for measurement sequences, such as the 7-measurement and 10-measurement sequences described herein, because a perfusion "snapshot" of the various wavelengths is desired so that ratios (and ratios of color change: called $O_2$ index) can be calculated from these measurements.

A Write Command may be used to write configuration data to one or more registers in a sensor module. For example, the host controller may use the Write Command to configure the operating mode of each of the sensor modules. In an optical sensor module, the operating modes may correspond to (1) a light emitter; (2) a light detector; (3) both a light emitter and a light detector; and (4) off. For blood oxygen content sensing, the sensor modules may be configured to operate as both light emitters and detectors. For tissue perfusion sensing, the sensor modules may be configured to be dedicated light emitters and detectors. In other examples, however, tissue perfusion sensing may occur with combined emitter/detector sensor modules.

In addition, the Write Command may be used to configure measurement parameters for the sensor modules. In the case of an optical sensor module, the Write Command may be used to configure the integration time (Tint) parameter, the LED current (LEDi) parameter, and the photodiode gain (Cint) parameter.

The bus communications protocol described above is merely one example of a bus communications protocol. Different communication protocols may also be used to achieve the technical advantages described in this disclosure. Another example bus communications protocol for use within sensing system 200 is described in U.S. Pat. No. 7,139,613 to Reinke et al., entitled, "IMPLANTABLE MEDICAL DEVICE COMMUNICATION SYSTEM WITH PULSED POWER BIASING," which issued on Nov. 21, 2006 and is incorporated herein by reference in its entirety.

Figure 9:
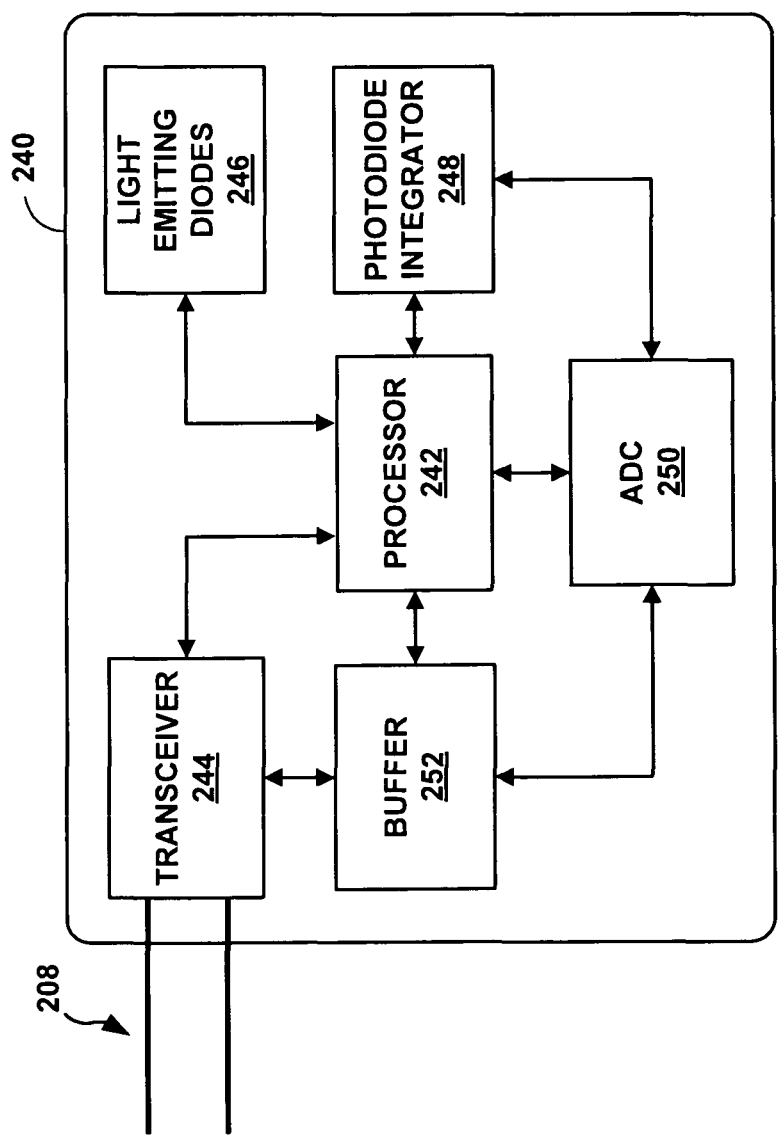
FIG. 9 is a conceptual illustration of an example sensor module that may be used within any of the sensing systems of this disclosure.

FIG. 9 is an exemplary diagram of an optical perfusion sensor 240 for use within any of the sensing and therapy systems of this disclosure. For example, optical perfusion sensor 240 may be used as sensor module 204 or 206 within system 200 of FIG. 8. Optical perfusion sensor 240 includes processor 242, transceiver 244, light emitting diodes 246, photodiode integrator 248, integrator 860, analog-to-digital converter 250, and buffer 252. Processor 242, transceiver 244, and buffer 252 may include components and function that are substantially similar to the components and functions described with respect to sensor modules 204 and 206 in FIG. 7.

Sensor module 240 may be configured to perform one or more sensor actions according to an operating mode prior to actually arming the sensors. The operating modes may include the following: (1) a light emitter operating mode; (2) a light detector operating mode; (3) both a light emitter and a light detector operating mode; and (4) an off operating mode. When performing optical perfusion measurements, sensor module 240 may receive a power pulse from a host controller over bus 208. Sensor module 240 may then coordinate the timing for performance of one or more sensor actions based on the received power pulse signal.

Light emitting diodes (LEDs) 246 are configured to generate or emit light towards blood-perfused tissue in order to perform tissue perfusion measurements. LEDs 246 may begin to emit light or cease to emit light in response to commands from processor 242. LEDs 246 may include three LEDs of differing wavelengths. The first LED may emit Red light having a wavelength in the range of about 550 nanometers (nm) to about 750 nm, and more particularly, in a range of about 650 nm to about 670 nm. The second LED may emit isobestic light having a wavelength in the range of about 750 nm to about 850 nm, and more particularly, in a range of about 790 nm to about 830 nm. The third LED may emit infrared light having a wavelength in the range of about 750 nm to about 2.5 micrometers or greater, and more particularly, in a range of about 805 nm to about 955 nm. Processor 242 is configured to control the amount of current that powers the LEDs based on a configuration parameter set by the host controller. The amount of current may be different for each LED because some wavelengths of light travel through tissue better than other wavelengths of light. In some examples, sensor module 240 may contain a dedicated current source for LEDs 246. The LEDs may be situated proximate to a transparent window that allows light to pass through the sensor module and into the blood-perfused tissue.

Photodiode integrator 248 is configured to measure an amount of light received by a photodiode or a phototransistor over a period of time. Photodiode integrator 248 includes a photodiode configured to receive an amount of light and convert the intensity of the received light to a voltage. The photodiode may be electrically coupled to an integration circuit that integrates the voltages over a period of time. In some examples, photodiode integrator 248 may include a phototransistor configured to receive an amount of light and convert the intensity of the received light to a voltage. The integration circuit may include, for example, an amplifier and a capacitor. The voltage from the photodiode may be electrically coupled to the input of the amplifier. The capacitor may be electrically coupled to the output of the amplifier such that the voltage across the photodiode is integrated or accumulated over a period of time. The time period for integration may be determined by an integration time configuration parameter that is set by the host controller. After the time period has expired, a sample and hold circuit may hold the integrated voltage level steady for a period of time in order for ADC 250 to receive a steady input. In some cases, photodiode integrator 248 may include a photodiode or phototransistor without the corresponding integration circuit.

ADC 250 converts the integrated voltage from an analog value to a digital value. The resolution of ADC 250 may be based on a configuration parameter that can be programmed by the host controller. In one example, the digital output of ADC 250 is a 16 bit number with 14 bits representing the digital value and 2 bits representing the measurement type. The measurement type may indicate if the integrated value corresponds to a Red light measurement, an isobestic light measurement, an infrared light measurement, or an ambient light measurement. After ADC 250 has converted the integrated voltage into a digital value representative of an amount of received light over a time period, ADC 250 may store the digital value in buffer 252. ADC 250 may store the results of multiple measurements in buffer 252 prior to transmitting any of the results back to the host controller.

ADC 250 may store the digital value in buffer 252 during a time period that substantially overlaps with transceiver 244 receiving a triggering command for a subsequent measurement. In other words, sensor module 240 may begin arming light emitting diodes 246 and/or photodiode integrator 248 for a next measurement, while the results for the previous measurement are being stored. This may result in substantial savings in time required for making multiple measurements.

During a normal optical perfusion measurement, sensor module 240 may perform the following sensor actions: (1) receive a trigger for a measurement from the host controller; (2) begin emitting light and integrate the received light over a time period; (3) perform analog-to-digital conversion on the integrated voltage; and (4) store the resulting digital value in a buffer. When multiple measurements are made, these four steps may need to be repeated for each measurement. In some examples, sensor module 240 may perform these steps sequentially for each measurement. However, in other examples, sensor module 240 may perform these steps according to a pipelined execution scheme. In some cases, more than one sensor module may perform one or more of these sensor actions for a particular measurement. For example, one sensor module may emit light, and another sensor module may integrate the received light, perform analog-to-digital conversion, and store the results in a buffer.

According to the pipelined execution scheme, sensor module 240, may receive a trigger for a subsequent measurement during the time period when the analog-to-digital conversion of the prior measurement is taking place. Thus, when sensor module 240 is storing the result of the first measurement in buffer 252, sensor module 240 may be simultaneously integrating the received amount of light for the next measurement. In other words, a time period for storing the results of a previous measurement may overlap, at least partially, with a time period for performance of the photodiode integration for a subsequent measurement. Alternatively, a time period for performing analog-to-digital conversion of a previous measurement may overlap, at least partially, with a time period for receiving a trigger for a subsequent measurement. In this manner, sensor module 240 is able to reduce the overall latency period for multiple measurements by overlapping or pipelining the performance of different sensor actions for each measurement.

In some examples, processor 242 may include a set of registers that store one or more configuration parameters for sensor module 240. In other examples, an EEPROM external to processor 242 may store these configuration parameters. The configuration parameters may control the operation mode of sensor module 240, as well as the timing for performance of sensor actions within sensor module 240

As one example, the configuration parameters may include a configuration parameter for the operating mode of sensor module 240. The operating modes may include (1) a light emitter operating mode; (2) a light detector operating mode; (3) both a light emitter and a light detector operating mode; and (4) an off operating mode. For blood oxygen content sensing, sensor module 240 may be configured to operate as both a light emitter and a light detector. For tissue perfusion sensing, sensor module 240 may be configured to be a dedicated light emitter or detector. In other examples, however, tissue perfusion sensing may occur with combined emitter/detector sensor modules.

As another example, the configuration parameters may include configuration parameters that control the performance of various sensor actions within the sensor module.

For example, the registers may store a parameter (Tint) that controls the integration time. This parameter controls how long the LEDs will emit light and how long the integrator will integrate the voltage across the photodiode during a particular measurement. When power pulses are used to control the timing of measurements, the integration time parameter will determine how many power pulses need to occur during a measurement. As one example, the integration time parameter may be programmable form 20 to 1023. In this example, the values from 0-19 are not used because a minimum number of power pulses are required for auto-zeroing the integration amplifier and for the sample-and-hold of the integrator result that occurs before analog-to-digital conversion.

In addition, the integration time parameter controls the synchronization of the optical modules that emit light and detect light during a measurement. When this parameter varies, the sensor control module may determine signal conditions that need to occur for performing various sensor actions. For example, processor 242 may determine a first number of power pulses that need to be received before light emitting diodes 246 begin emitting light based on the integration time parameter. Processor 242 may also determine a second number of power pulses that need to be received before photodiode integrator 248 begins to measure the amount of received light based on the integration time parameter. Processor 242 may also determine a third number of power pulses that need to be received before the photodiode integrator 248 ceases to measure the amount of received light based on the integration time parameter. Finally, Processor 242 may determine a fourth number of power pulses that need to be received before the light emitting diodes 246 cease to emit light based on the integration time parameter. In general, the fourth number may be greater than the third number, which may be greater than the second number, and which may greater than the first number of power pulses. In this manner, sensor module 240 determines from the integration time parameter, a sequence of signal conditions that synchronize one or more sensor modules such that light emission occurs before light detection and light detection ends before light emission ends. In other words, sensor module 240 determines overlap conditions such that light emission occurs before light integration begins, and light integration ends before light emission ends. Look-up tables or a hard wired function may assist the sensor module in determining the appropriate signal conditions. In some examples, one or more of the signal conditions may occur simultaneously with another of the signal conditions. In cases where the signal conditions include counting the number of power pulses, one or more of the first number of power pulses, the second number of power pulses, the third number of power pulses, and the fourth number of power pulses may be equal to each other.

The configuration parameters may also include a parameter (LEDi) that controls the LED current supplied to the light emitting diodes 246. The amount of LED current supplied to the LEDs 246 will affect the intensity of light produced by the LEDs as well as how much power is consumed by the sensor module during a measurement. In general, certain wavelengths of light travel through tissue better other wavelengths. Thus, for wavelengths that travel through tissue better, a lower amount of LED current may be used. More particularly, light in the infrared (IR) spectrum passes through tissue easier than light in the Red spectrum. Thus, it may be desirable to adjust the LED current not only to save power on wavelengths that do not require as much current, but also to better control the resulting intensity of light measured by the photo integrator so that the measured values are in an appropriate range for the analog-to-digital converters. In one example, the LED current value may be programmable to allow for LED current ranging from approximately 125 µA to 10.125 mA.

The configuration parameters may also include a parameter (Cint) that controls the photodiode gain within photodiode integrator 248. This parameter may be used to control the integration capacitor size within the integration circuit. In one example, nine settings may be used between 2 pF and 32 pF. The settings may have a logarithmic scale such that the possible settings for the integration capacitor are: 2 pF 3 pF, 4 pF, 6 pF, 8 pF, 12 pF, 16 pF, 24 pF and 32 pF. In another example, 28 settings may be used within the range of 2 pF to 32 pF to guarantee montonicity. In general, the photodiode gain parameter may be used to ensure that the measured results are within a proper range such that the analog-to-digital converter can convert the values with an acceptable resolution.

Certain constraints may be imposed on how the sensor module parameters may be varied during a measurement sequence. For example, the integration time (Tint) parameter and the photodiode gain (Cint) parameter may both be required to remain constant during a measurement sequence. Such a constraint may provide a constant frame of reference for the measurements at differing wavelengths. In contrast, the LED current may be set to a different value for each of the different measurements. This is because the each of the LEDs has a different efficiency, and light in the IR spectrum passes through tissue easier than light in the Red spectrum.

In general, the analog-to-digital converter in sensor module 240 has a limited usable range. If the measurement parameters are adjusted such that the resulting measurement values have a large variance, then signal clipping can occur because the values may not fall within the usable range of the ADC. On the other hand, if the measurement parameters are adjusted such that the resulting measurements have many values that are close together (i.e. a small variance), then it may be difficult to accurately quantify changes in the signal. Thus, it may be desirable to adjust the operating parameters of the sensor modules before commencing measurements as well as from time-to-time between measurements to ensure that the resulting values are within proper range for the ADC. These operating parameters may include the integration time (Tint) parameter, the LED current (LEDi) parameter, and the photodiode gain (Cint) parameter.

In some examples, host controller 202 may be configured to automatically adjust or program one or more these parameters such that the resulting measurement values are within the usable ADC range. The automatic adjustment of parameters may be a closed-loop adjustment algorithm that takes place prior to commencing measurements as well as during measurement sequences. The automatic adjustment algorithm may perform initial sensor measurements using default parameters or parameters used in previous measurements. Then, the algorithm may adjust the parameters based on the digital values received from the analog-to-digital converter. The algorithm may be performed by host processor 202 or by individual sensor modules 204, 206. The algorithm may attempt to adjust and/or optimize the parameters such that ambient light measurement results as well as ambient light plus LED light measurement results are both within the usable ADC range. The algorithm may also attempt to adjust and/or optimize the parameters such that all results have an adequate degree of accuracy and precision. In addition, the algorithm may attempt to periodically adjust the parameters in order to compensate for changes in patient motion, physiology, conditions or other changes. For example, the algorithm may adjust parameters to compensate for a patient who is experiencing ventricular fibrillation.

In one example, the parameter adjustment algorithm may adjust the parameters for each sensor module according to the following prioritization with the first listed parameter having the highest priority: (1) LED current (LEDi); (2) Photodiode Gain (Cint); and (3) Integration time (Tint). In addition, the parameter adjustment algorithm may start by adjusting parameters for individual LEDs and/or sensor modules in the following order: (1) Red LED; (2) Iso LED; and (3) IR LED. In cases where one or more of the parameters cannot be adjusted properly, a flag may be set to indicate that the resulting measurements may be invalid. For example, if the sensor modules are being used by an ICD to determine whether or not to deliver a electrical shock to a patient, the ICD may decide not to use (i.e. ignore) tissue perfusion measurements as part of determining whether to deliver an electrical shock if one or more of the invalid flags is set for a sensor module.

Figure 10:
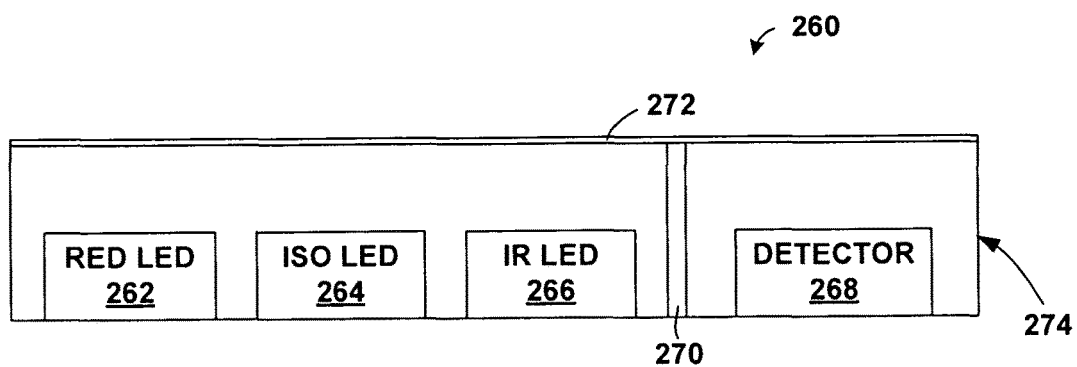
FIG. 10 is a conceptual illustration of an example sensing element that may be used within any of the sensor modules of this disclosure.

FIG. 10 is a conceptual illustration of an example sensing element 260 that may be used within any of the sensor modules of this disclosure. As shown in FIG. 10, sensing element 260 is an optical perfusion sensor that includes a red LED 262, an isobestic (Iso) LED 264, an infrared (IR) LED 266, a detector 268, and optical barrier 270. Red LED 262 may emit light in the red portion of the visible light spectrum, such as, but not limited to, light having a wavelength in a range of about 550 nanometers (nm) to about 750 nm, and more particularly, in a range of about 650 nm to about 670 nm. In one example, the light emitted by red LED 262 may have a peak value of about 660 nm with a half width of about 20 nm. Iso LED 264 may emit isobestic light in the isobestic portion of the light spectrum, such as, but not limited to, light having a wavelength in a range of about 750 nm to about 850 nm, and more particularly, in a range of about 790 nm to about 830 nm. In one example, the light emitted by Iso LED 264 may have a peak value of about 810 nm with a half width of about 35 nm. IR LED 266 may emit IR light in the IR portion of the light spectrum, such as, but not limited to, light having a wavelength in a range of about 750 nm to about 2.5 micrometers or greater, and more particularly, in a range of about 805 nm to about 955 nm. In one example, the light emitted by IR LED 266 may have a peak value of 880 nm and a half width of about 75 nm.

Detector 268 is configured to detect light emitted from red LED 262, Iso LED 264, and IR LED 266, and may include, for example, a photodetector, such as a photodiode or phototransistor. Detector 268 may also include a photodiode integrator as described above with respect to FIG. 9. Detector 268 may convert sensed light into either a current or voltage, which may be outputted as an electrical signal. An intensity of the signal received by detector 268 may be indicative of hemodynamic function, such as oxygen saturation of blood, a blood perfusion level in tissue, or the blood pressure of patient 12. In examples in which detector 268 includes a photodiode, an electrical signal outputted by detector 268 may be directly or inversely proportional to the amount of light (e.g., the intensity of light) incident on the photodiode. In some examples, detector 268 may include a photo integrator that includes a photodiode coupled to an integration circuit. The integration circuit may keep a running total of the amount of light received by the photodiode over a period of time.

Red LED 262, Iso LED 264, IR LED 266, detector 268, and optical barrier 270 may be positioned within sensor housing 274. In some examples, sensor housing 274 is defined by a recess within an outer housing of IMD 16, and red LED 262, Iso LED 264, IR LED 266, detector 268 may be disposed within the recess. In other examples, sensor housing 274 may at least partially extend from an outer housing of IMD 16, such that at least a part of optical perfusion sensor 260 protrudes from the outer housing of IMD 14.

In some examples, optical perfusion sensor 260 may include lens 272 that helps focus light emitted from red LED 262, Iso LED 264, and IR LED 266. Red LED 262, Iso LED 264, and IR LED 266 are configured to emit light through lens 272, and detector 268 is configured to detect light received through lens 272. Optical barrier 270 may be positioned within optical perfusion sensor housing 260 to block direct transmission of light from LEDs 262, 264, 266 to detector 268.

Optical perfusion sensor 260 may be subcutaneously implanted within patient 12 such that lens 272 is oriented toward blood perfused tissue of patient 12, e.g., proximate to vasculature of patient 12. In one example, red LED 262, Iso LED and IR LED 266 are positioned on the same side of the blood perfused tissue as detector 268, such that detector 268 detects light emitted from LEDs 262, 264, 266 and reflected by the patient's blood. For example, red LED 262, Iso LED 264, IR LED 266, and detector 268 may be coupled to a common surface of the IMD 16 housing. This type of optical perfusion sensor may be referred to as a reflective perfusion sensor. In other examples, LEDs 262, 264, 266 may be positioned on an opposite side of the blood perfused tissue from detector 268, such that detector 268 detects light that is transmitted through the blood perfused tissue. This latter example is commonly referred to as a transmissive perfusion sensor.

In other examples, optical perfusion sensor 260 may include any two or more light sources for producing at least two different wavelengths of light. The light sources and detector 268 may have any suitable arrangement.

Figure 11:
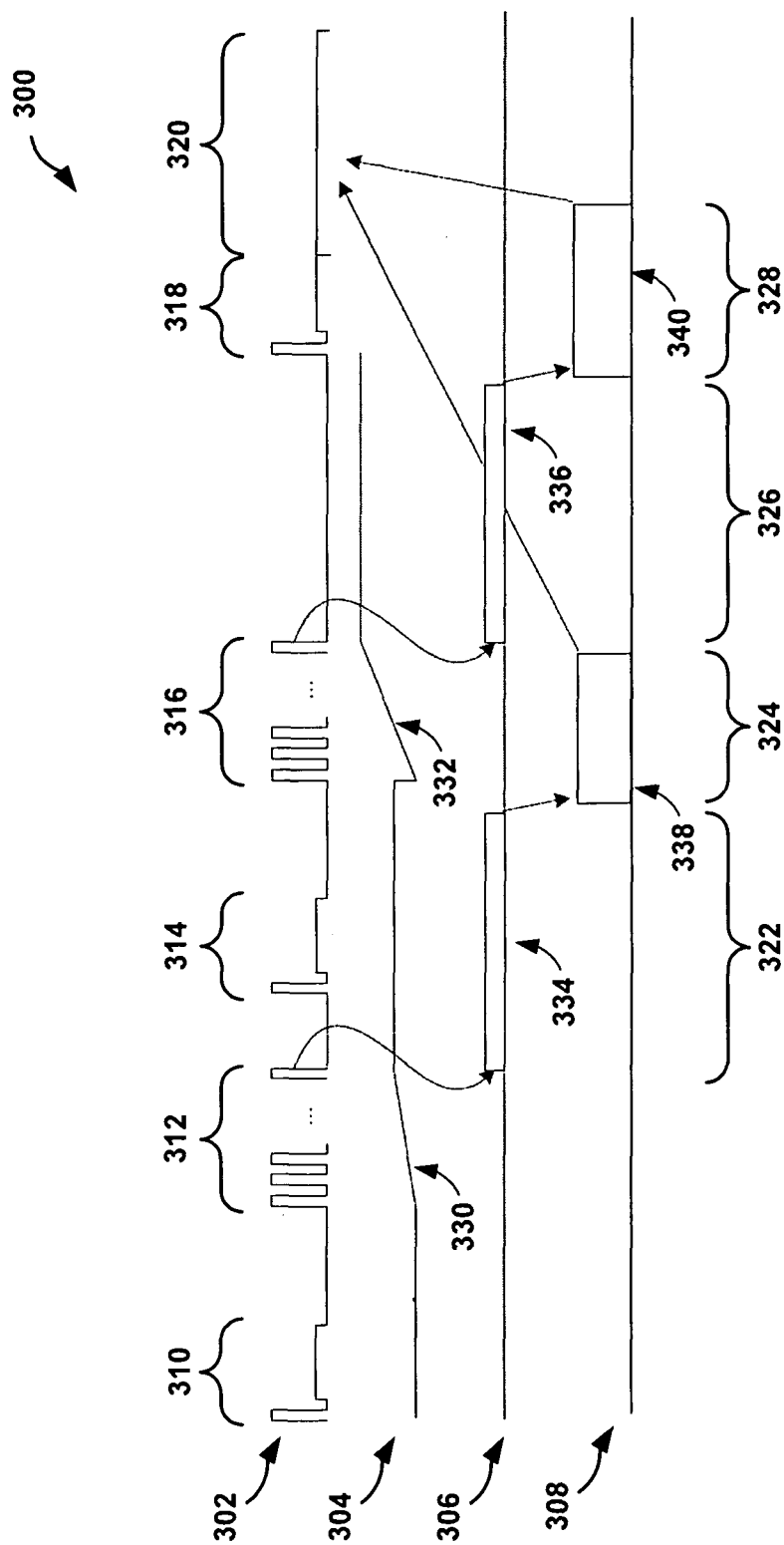
FIG. 11 is an example timing diagram illustrating a pipelined execution scheme for the sensing system of FIG. 8.

FIG. 11 is an example timing diagram 300 illustrating a pipelined execution scheme for the optical perfusion sensing system of FIG. 8. The horizontal axis of the timing diagram is given in units of time and increases from left to right. In general, timing diagram 300 displays the timing coordination between a host controller (FIG. 8—202) and a light detector module (FIG. 9—240). The timing coordination of the light emitter module is not depicted in timing diagram 300. Timing diagram 300 includes bus signal 302, photodiode integrator signal 304, analog-to-digital conversion signal 306, and buffer signals 308. Bus signal 302 represents the voltage level over two-wire bus 208 as time increases. The voltage represented by bus signal 302 may be indicative of a voltage between the voltage on data wire 208A and ground wire 208B of two-wire bus 208. Photodiode integrator signal 304 represents the voltage at the output of the photodiode integrator 248 within sensor module 240. Analog-to-digital conversion signal 306 represents the time period for which ADC 250 within sensor module 240 is performing analog-to-digital conversion. Buffer signal 308 represents the time period for which sensor module 240 is recording results within buffer 252.

In FIG. 11, the higher voltage level fluctuations in bus signal 302 represent power pulses, and the lower voltage level fluctuations represent data bit communication. For example, during time period 312, the voltage fluctuations represent monophasic power pulses, which may be in a range of about 2.4 Volts to about 3.4 Volts, and preferably at a magnitude of about 2.8 Volts. During time period 310, a single power pulse is followed by a single pulse of lower voltage, which may be on the order of 200 mV in one example, indicating the communication of several data bits. Although the data bit communication is shown as a single voltage pulse during time period 310, the single voltage pulse may actually represent a plurality of bit times with multiple transitions between high and low bus voltages. In other words, multiple bits may be transmitted during the time period indicated by the single low-voltage pulse in time period 310. The communication of data bits may include the transmission and reception of digital ones and digital zeros (i.e. logic "1's" and logic "0's") as described herein.

Timing diagram 300 illustrates the initiation and performance of two measurements. During time periods 310 and 314, host controller 202 issues two triggering commands to the sensor modules. The first triggering command is issued during time period 310 and arms one or more sensor modules for making a first measurement. The second triggering command is issued during time period 314 and arms one or more sensor modules for making a second measurement. The triggering commands may be Quick Trigger commands. As one example, the first measurement may be an ambient light measurement, and the second measurement may be a red light plus ambient light measurement. Post-processing on the measurement results may allow for the ambient component (i.e. noise component) to be subtracted out from the red light measurement. In timing diagram 300, the sensor modules that perform the first and second measurement are the same sensor module. However, in other examples, different sensor modules could be used.

After the triggering commands are issued, there is an optional delay that may take place on bus signal 302. After the delay, host controller 202 issues power pulses for each of the measurements during time periods 312 and 316. As shown in FIG. 11, the power pulses are monophasic power pulses. In other examples, however, biphasic power pulses may be used. During time periods 312 and 316, the light emitter sensor module may begin to emit light upon receiving a first number of power pulses. After light emitter sensor module begins to emit light, sensor module 240 may begin to detect light upon receiving a second number of power pulses. The second number of power pulses may be greater than the first number of power pulses in order to cause the LEDs to emit light prior to turning on the photodiode integrator. During the time periods 312 and 316, photodiode integrator signal 304 indicates a steady increase in voltage (330, 332). This represents the accumulation of the voltage across the photodiode over a period of time, which in turn represents the intensity of the received light over a period of time.

After sensor module 240 has finished integrating the voltage across the photodiode, sample and hold circuits stabilize the voltage at the output of the photodiode integrator so that the voltages can be processed by the analog-to-digital converter. Analog-to-digital converter 250 performs analog-to-digital conversion (334, 336) during time periods 322 and 326. The photodiode integrator signal 304 indicates a steady voltage during this time period.

After sensor module 240 has performed analog-to-digital conversion for the measurements, sensor module 240 may store the results in the buffer 252 of sensor module 240 (338, 340). This occurs during time period 324 and 328. After both results have been stored, host controller 202 may transmit a Read Results command over bus 202 to sensor module 240 during time period 318. Sensor module 240 may then transmit the results stored in the buffer over bus 208 to host controller 202 as a single packet during time period 320.

As illustrated in timing diagram 300, the second power pulse signal for the second measurement is transmitted over the bus during time period 316 and host controller 202 does not receive the results for the first measurement until time period 320. As such, host controller 202 issues a second power pulse for making a second measurement prior to receiving results from the first measurement. Timing diagram 300 also illustrates that a time period 314 for issuing a second triggering command for a second measurement overlaps, at least partially, with a time period 322 for performing analog-to-digital conversion of the first measurement. Timing diagram 300 also illustrates that a time period 324 for performance of the first sensor action 332 of a subsequent measurement overlaps, at least partially, with a time period 324 for performance of the second sensor action 338 of a previous measurement. Timing diagram 300 also illustrates that the results of the multiple measurements from the sensor module to the host controller as a single packet over the bus. Although the multiple measurements in timing diagram 300 are described as being performed by the same sensor module, in other examples, the different measurements may be performed by different sensor modules.

The timing diagram in FIG. 11 generally illustrates an example pipelined execution scheme where a time period for integration of a subsequent measurement overlaps, at least partially, with the storage of results in a buffer for a previous measurement. In other examples, however, the timing of multiple measurements may be more tightly integrated. For example, in some cases, a time period for integration of a subsequent measurement may overlap, at least partially, with the analog-to-digital conversion of a previous measurement.

In general, the accuracy, resolution, and noise performance of the ADC conversion can be increased by increasing the time spent for performing the ADC conversion. This is particularly true for analog-to-digital converters that use oversampling techniques to improve performance proportionally with the number of clock cycles available for the measurement. Similarly, the noise performance of the photodiode integrator can be improved by increasing the time for performance of the photodiode integration. In some examples, the noise performance for the photodiode integrator may be reduced as the inverse of the square root of the integration time. By maximizing the time available for the ADC conversion and the integration operation, the overall accuracy of the measurements may be improved. The pipelined execution schemes described in this disclosure can increase the available time for performing ADC conversion and photo-integration without sacrificing overall throughput. This is because the datapath for a single measurement is split into at least two separate pipelining stages—a first stage for photo-integration and a second stage for analog-to-digital conversion. Thus, the photo-integration for a subsequent measurement may happen concurrently with, or at least during a time period that partially overlaps with, the ADC conversion for a previous measurement. In this manner, the accuracy, resolution, and noise performance for measurements may be improved without sacrificing overall throughput of measurements within the sensing system.

Although FIG. 11 illustrates a pipelined execution scheme for only two measurements, it should be noted that the pipelined execution scheme may be extended to more measurements such as a seven measurement sequence, a ten measurement sequence, or other type of measurement sequence. For example, a seven measurement sequence may comprise seven measurements that take place in the following order: (1) a first ambient light measurement; (2) a red light measurement; (3) a second ambient light measurement;

(4) an isobestic light measurement; (5) a third ambient light measurement; (6) an infrared light measurement; and (7) a fourth ambient light measurement. The integration times for each of the measurements in the seven measurement sequence may be equal to each other. The ambient light measurements constitute measurements that occur without emitting any additional light via light emitting diodes. The colored light measurements, which include the red light measurement (2), the isobestic light measurement (4), and the infrared measurement (6), constitute measurements that occur by emitting light via the corresponding colored light emitting diode. Thus, the colored light measurements measure both ambient light and light from the corresponding colored light emitting diode. The "noise" due to the ambient light may be subtracted out of the raw colored light measurements to produce a compensated colored light measurement. The seven measurement sequence allows an average ambient light level to be calculated for each colored light measurement based on the ambient light measurements that occur immediately prior to and after each colored measurement. For example, an average ambient light measurement that corresponds to the red light measurement (2) can be calculated by averaging the first ambient light measurement (1) and the second ambient light measurement (3). Calculating average ambient light levels for each of the colored measurements allows for the correction of measurements due to increasing or decreasing ambient light levels that may occur during the seven measurement sequence.

As another example, a ten measurement sequence may comprise ten measurements that take place in the following order: (1) Amb0; (2) Red; (3) Amb0;(4) Amb1;(5) Iso; (6) Amb1;(7) Amb2;(8) IR; (9) Amb2; and (10) Amb0. Unlike the 7-measurement sequence, the integration times for each of the colored light measurements in this example may be different. The Amb0 ambient measurement may have an integration time equal to the integration time for the Red light measurement. Similarly, the Amb1 ambient measurement may have an integration time equal to the integration time for the Iso light measurement, and the Amb2 ambient measurement may have an integration time equal to the integration time for the IR light measurement. Because the integration times may be different for each of the different colored light measurements, additional ambient light measurements are added to the ten measurement sequence. This allows an average ambient light level to be calculated for each colored light measurement based on the ambient light measurements that occur immediately prior to and after each colored measurement. The final Amb0 measurement can be compared to the first Amb0 measurement to detect an aggregate change in the ambient light from the beginning of the measurement sequence to the end of the measurement sequence.

In additional examples, the measurement sequence may perform ambient measurements only at the beginning and end of the measurement sequence. For example, a five measurement sequence may be used that performs the following measurements: (1) Amb; (2) Red; (3) Iso; (4) IR; (5) Amb. In further examples, the measurement sequence may perform only a single ambient measurement for each type of light measurement. For example, a six measurement sequence may be used that performs the following measurements: (1) Amb0;(2) Red; (3) Amb1; (4) Iso; (5) Amb2; (6) IR. Other types of measurement sequences are also possible without departing from the scope of the invention.

When making perfusion measurements, it may be desirable to gather all the reflected wavelengths instantaneously, and then to gather the ambient or dark measurement. However, this is difficult to do in a low-current small circuit area implementation. Thus, each wavelength of interest may be gathered sequentially as described in the 7-measurement and 10-measurement sequences. By gathering each wavelength as close together in time as possible, a snapshot of the perfusion level of the measured tissue may be obtained that approaches the quality of an instantaneous measurement. This is analogous to a shutter of a camera being open a long time vs. a short time. If the shutter is open a long time, the picture may be blurry. On the other hand, if the shutter is open for a short time, the picture may be more clear as long as enough light is allowed into the camera. The pipelined execution schemes described in this disclosure allow post-processing operations, such as analog-to-digital conversion, to occur simultaneously with a subsequent measurement thereby reducing the latency between the measurement of each wavelength. This in turn, allows a perfusion snapshot that better approximates an instantaneous perfusion snapshot.

Figure 12:
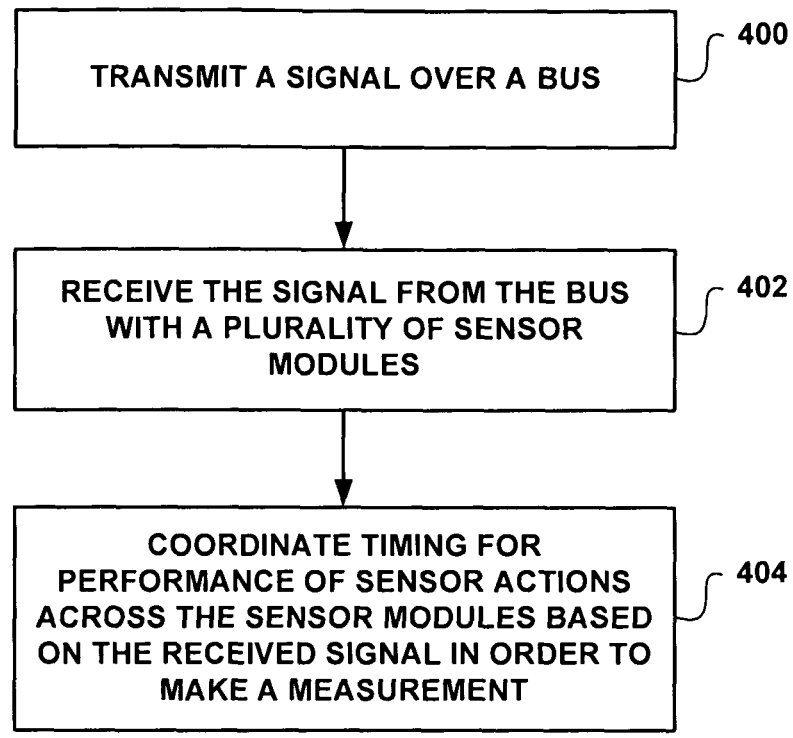
FIG. 12 is a flowchart illustrating an example method for making a measurement with one of the systems described in this disclosure.

FIG. 12 is a flowchart illustrating an example method for making a measurement with one of the systems described in this disclosure. Host controller 202 transmits a signal over a bus (400). A plurality of sensor modules receive the signal from the bus (402). The plurality of sensor modules coordinate timing for performance of sensor actions across the sensor modules based on the received signal in order to make a measurement (404). When making a measurement, multiple sensor actions may need to occur in a particular order in order to obtain valid results for the measurement. In many cases, individual sensor actions may be performed by distinct sensor modules that share a common bus. By coordinating the timing for performance of sensor actions across the sensor modules, the sensor modules are able to control the timing for performance of the sensor actions such that all of the sensor actions occur in the desired order even if the individual sensor actions are performed by separate sensor modules.

The measurement may be a tissue perfusion measurement, a blood oxygen level measurement, a sonomicrometry measurement, or a pressure measurement. The measurement may be a tissue perfusion measurement, a blood oxygen level measurement, a sonomicrometry measurement, or a pressure measurement. In some cases, the timing for multiple sensor actions may be coordinated across the sensor modules such that a first sensor action performed for a measurement prior to a second sensor action. For example, with regard to optical perfusion measurements, the sensor modules may use the received signal to control the sensor modules such that one sensor modules begins to emit light prior to a second module beginning to detect light. The bus may be either a 2-wire bus or a 3-wire bus. The signal may be a signal that is substantially periodic, such as a pulsed signal for example. When a pulsed signal is transmitted over the bus, the signal may be either a monophasic pulsed signal or a biphasic pulsed signal. The signal may supply power, data, and timing information to the plurality of sensor modules. In other words, a single wire within the 2-wire bus may function as a power wire, a clock wire, and a data wire with reference to the other wire, which functions as a ground wire. In some examples, a third wire may be added to the bus to supply a direct current (DC) voltage with reference to the ground wire. The DC voltage may be used for powering sensor actions that require higher current, such as emitting light with the LED's.

Figure 13A:
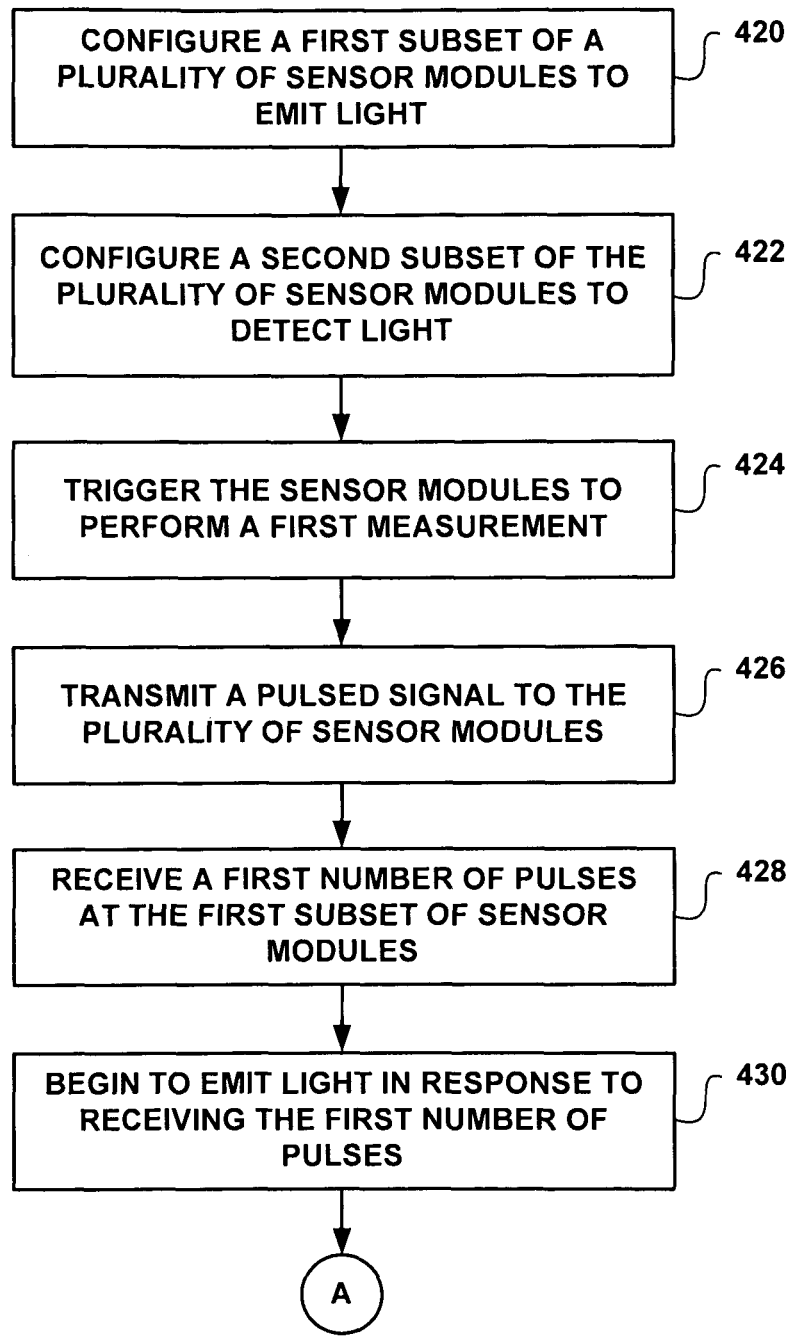
FIGS. 13A and 13B are flowcharts illustrating an example method for taking an optical perfusion measurement by using a plurality of modules interconnected via a bus.
Figure 13B:
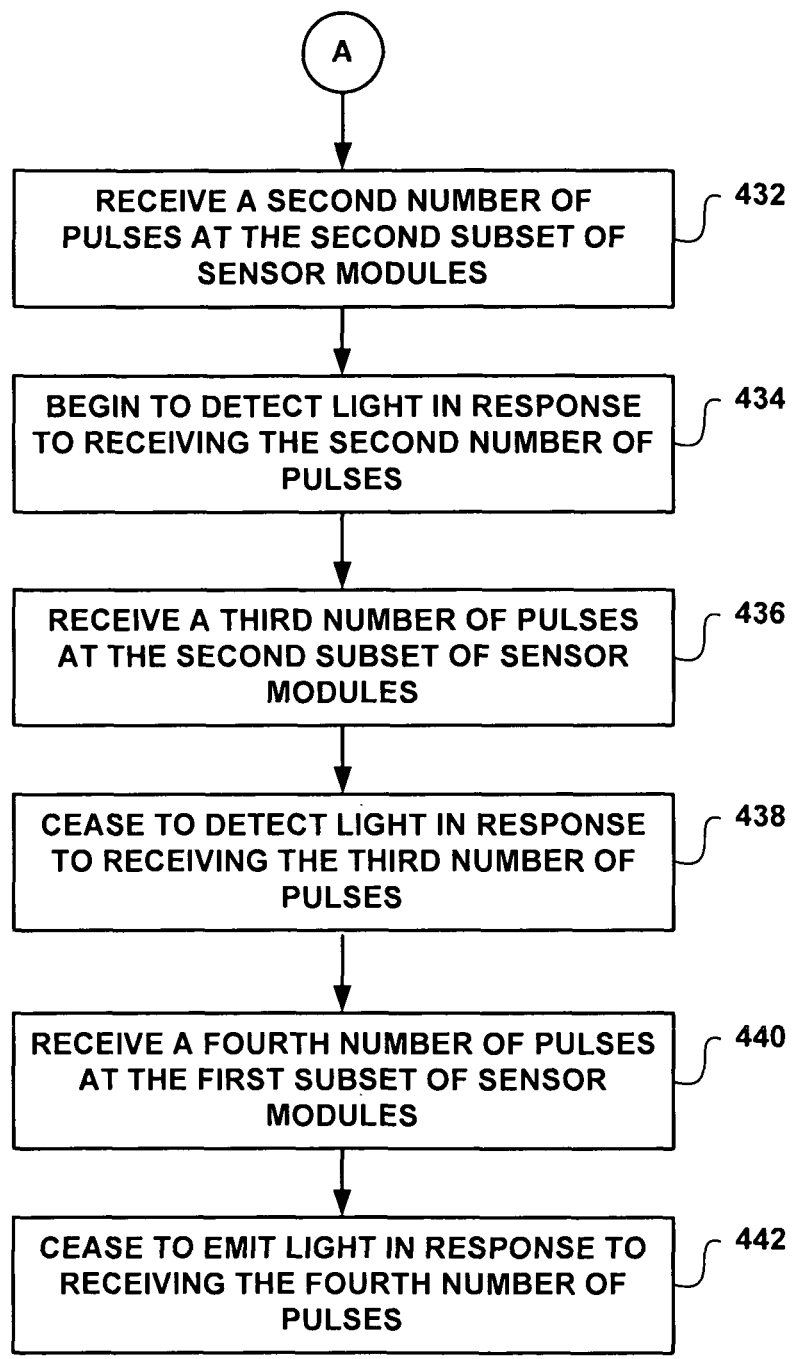

FIGS. 13A and 13B are flowcharts illustrating an example method for taking an optical perfusion measurement by using a plurality of modules interconnected via a bus. Host controller 202 configures a first subset of the plurality of sensor modules to emit light (420), and configures a second subset of the plurality of sensor modules to detect light (422). Host controller 202 may configure the sensor modules by issuing a Write command, which may write data values to one or more registers within the sensor modules. For example, each of the sensor modules may include an operating mode register that controls the operating mode of the sensor module. The current data value stored in the register may determine the operating mode of the sensor module. Example operating modes may include a light emitter mode, a light detector mode, both a light emitter and light detector mode, or a turned off mode.

In some examples, the Write command may take the form of two commands. A first command may be a Register Address command, which adjusts or sets the register pointer for one or more sensor modules. The second command may be a Register Write command, which designates the data to be written to the register indicated by the register pointer. The Register Address command may contain an address field, which indicates the sensor modules that the Register Address command will affect, and a data field, which indicates the new register address for the register pointer. The Register Write command may also contain an address field, which indicates the sensor modules that the Register Write command will affect, and a data field, which indicates the actual data to write to the register pointed to by the register pointer. In cases where the register pointer points to the operating mode register, the actual data will indicate the operating mode of the sensor. Each of these commands may be addressed to a single sensor module, multiple sensor modules, or all of the sensor modules. These commands may also contain start sequences, CRC codes, and stop sequences similar to the triggering commands described in this disclosure. These commands may also contain a unique command code indicating whether the command is a Register Address command or a Write Register command.

Host controller 202 triggers the sensor modules to perform a first measurement (424). Host controller 202 may use a Long Trigger command or a Quick Trigger command to trigger the sensor modules. These commands arm the sensor modules in preparation for a measurement. In one example, arming the sensor modules causes the sensor modules to monitor the bus for power pulses that follow the triggering command, and to perform sensor actions in response to the power pulses. In such an example, sensor modules that are not armed will not perform sensor actions in response to the power pulses that follow the triggering command.

Host controller 202 transmits a pulsed signal to the plurality of sensor modules (426). The pulsed signal provides timing information for the performance of sensor actions, such as beginning to emit light and/or detect light and ceasing to emit light and/or detect light. In some examples, the pulsed signal may also supply power and/or LED current to the sensor modules in order to emit light. The first subset of sensor modules may receive a first number of pulses (428), and begin to emit light in response to receiving the first number of pulses (430). The second subset of sensor modules may receive a second number of pulses (432), and begin to detect light in response to receiving the second number of pulses (434). The second subset of sensor modules may receive a third number of pulses (436), and cease to detect light in response to receiving the third number of pulses (438). The first subset of sensor modules receive a fourth number of pulses (440), and cease to emit light in response to receiving the fourth number of pulses (442). In some examples, the reception of a particular number of pulses may be the reception of a particular number of power pulses during a time period. In addition, the time period for receiving the first number, second number, third number, and fourth number of power pulses may be the same time period.

In some examples, the first number, second number, third number, and fourth number may be hard-wired into the sensor modules. In other examples, the first number, second number, third number, and fourth number may be programmed by host controller 202. In one example, host controller 202 may separately configure each of the sensor modules with the appropriate numbers and/or signal conditions. In another example, host controller 202 may configure the integration time parameter (Tint) that is associated with each of the sensor modules. The first subset of sensor modules may then calculate the first and fourth numbers based on the integration time parameter. Similarly, the second subset of sensor modules may calculate the second and third numbers based on the integration time parameter. In yet another example, the first and second numbers may be hard-wired into the sensor modules, and the third and fourth numbers may be calculated by the sensor modules based on the integration time parameter (Tint) programmable by host controller 202.

Figure 14:
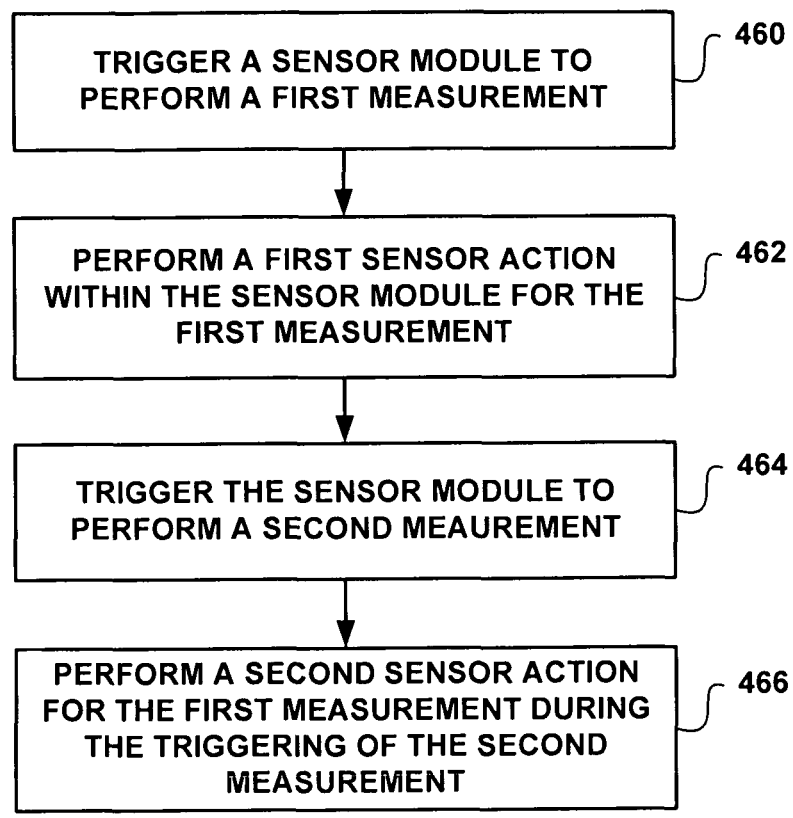
FIG. 14 is a flowchart illustrating an example pipelining method for use within any of the systems of this disclosure.

FIG. 14 is a flowchart illustrating an example pipelining method for use within any of the measurement systems of FIGS. 1-3. Host controller 202 triggers a sensor module to perform a first measurement (460). The sensor module performs a first sensor for the first measurement (462). Host controller 202 triggers the sensor module to perform a second measurement (464). The sensor module performs a second sensor action for the first measurement during the triggering of the second measurement (466).

Figure 15:
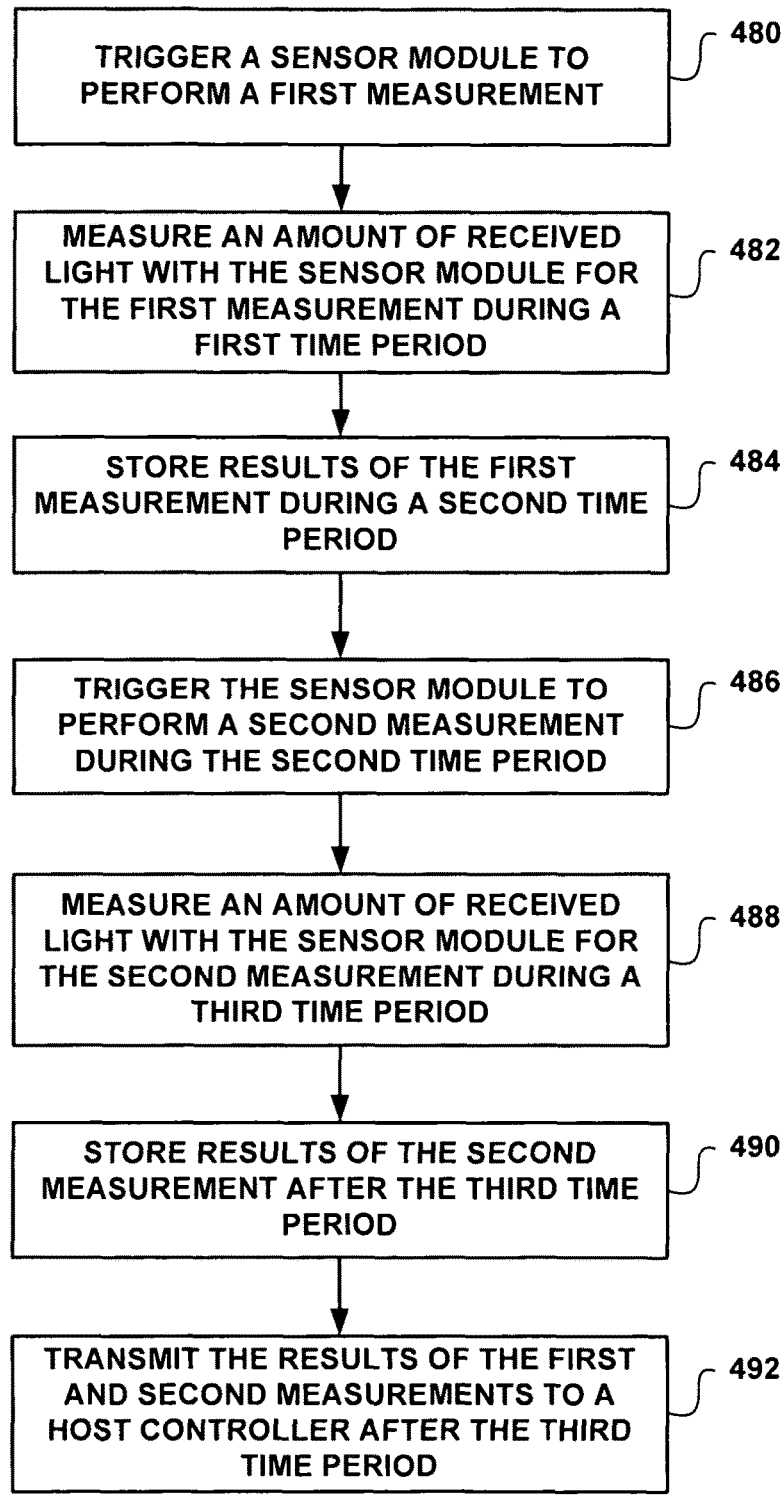
FIG. 15 is a flowchart illustrating another example pipelining method for use within any of the systems in this disclosure.

FIG. 15 is a flowchart illustrating another example pipelining method for use within any of the measurement systems of this disclosure. Host controller 202 triggers a sensor module to perform a first measurement (480). The sensor module measures an amount of received light for the first measurement during a first time period (482). The sensor module stores the results of the first measurement during a second time period (484). Host controller 202 triggers the sensor module to perform a second measurement during the second time period (486). The sensor module measures an amount of received light for the second measurement during a third time period (488). The sensor module stores results of the second measurement after the third time period (490). Host controller 202 transmits the results of the first measurement and the second measurement to a host controller after the third time period (492).

Figure 16:
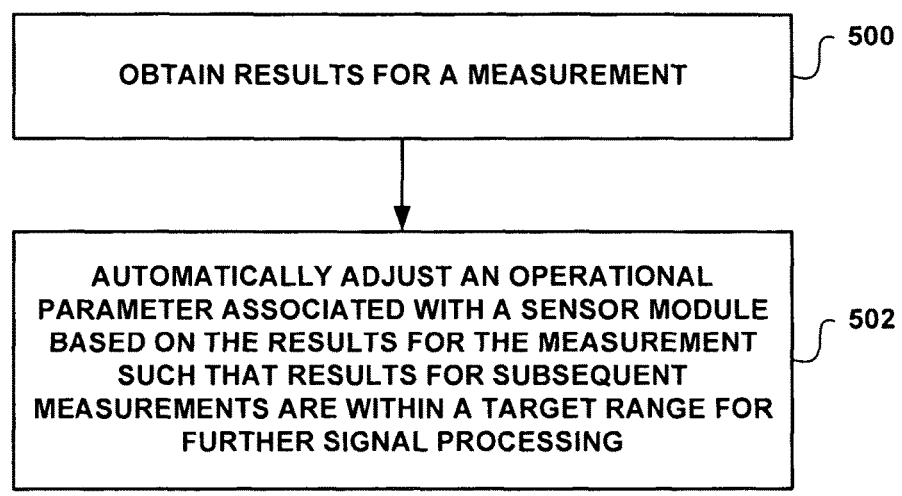
FIG. 16 is a flowchart illustrating an example method for providing closed loop adjustment of one or more operational parameters used by any of the implantable medical devices of this disclosure.

FIG. 16 is a flowchart illustrating an example method for providing closed loop adjustment of one or more operational parameters used by any of the implantable medical devices of this disclosure. Host controller 202 obtains results for a measurement (500). The measurement may be a tissue perfusion measurement, an oxygen sensing measurement, a sonomicrometry measurement, a pressure measurement, or any other type of measurement that includes an actuating sensor module and a detection sensor module. In some examples, the measurement may be a calibration measurement or a test measurement rather than an actual data measurement. Each of the measurements may be based upon the performance of a first sensor action by a first sensor module and upon the performance of a second sensor action performed by a second sensor module. The host controller, the first sensor module, and the second sensor module may be coupled together via a common bus. In some embodiments, the first and second sensor modules may be coupled to the bus via a common port. In other embodiments the first and second sensor modules may be coupled to the bus via separate ports.

Host controller 202 automatically adjusts an operational parameter associated with the sensor module based on the results for the measurement such that results for subsequent measurements are within a target range for further signal processing (502). In some cases, the operational parameter may be stored in memory and/or registers associated with the sensor module. In some examples, host controller 202 may adjust the parameters such that results for subsequent measurements have a magnitude within a target range for analog-to-digital conversion. In other examples, host controller 202 may adjust the parameters such that results for subsequent measurements have an amplitude variation within a target range for analog-to-digital conversion. In additional examples, host controller 202 may adjust the parameters such that both the magnitude and the amplitude variation of the results are within target ranges for analog-to-digital conversion.

Host controller 202 may adjust any number of parameters within one or more sensor modules to achieve measurement results that are within an appropriate range for further signal processing. For example, when performing tissue perfusion measurements, host controller 202 may adjust one or more of the following parameters: a light emitting diode supply current parameter (LEDi) associated with a sensor module that is configured to emit light, an integration time parameter (Tint) associated with a sensor module configured to detect light, and an integration capacitor parameter (Cint) associated with a sensor module configured to detect light.

In some examples, there may be a plurality of LED supply current parameters for each type of light measurement. For example, a sensor module configured to emit light may contain one of more of the following parameters: a red light emitting diode supply current parameter (Red LEDi) that controls the intensity of red light produced for red light measurements, an isobestic light emitting diode supply current parameter (Iso LEDi) that controls the intensity of isobestic light produced for isobestic light measurements, and an infrared light emitting diode supply current parameter (IR LEDi) that controls the intensity of infrared light produced for infrared light measurements.

In additional examples, there may be a plurality of integration time parameters for different types of measurements. For example, a sensor module configured to detect light may contain one or more of the following parameters: a red light integration time parameter (Red Tint) that controls the integration time for red light measurements, an isobestic light integration time parameter (Iso Tint) that controls the integration time for red light measurements, and an infrared light integration time parameter (IR Tint) that controls the integration time for infrared light measurements. In some examples where there are multiple integration time parameters, there may also be multiple ambient integration time parameters. For example, there may be a first ambient integration time parameter (Amb0 Tint) that corresponds to the Red Tint parameter, a second ambient integration time parameter (Amb1 Tint) that corresponds to the Iso Tint parameter, and a third ambient integration time parameter (Amb2 Tint) that corresponds to IR Tint parameter.

Figure 17:
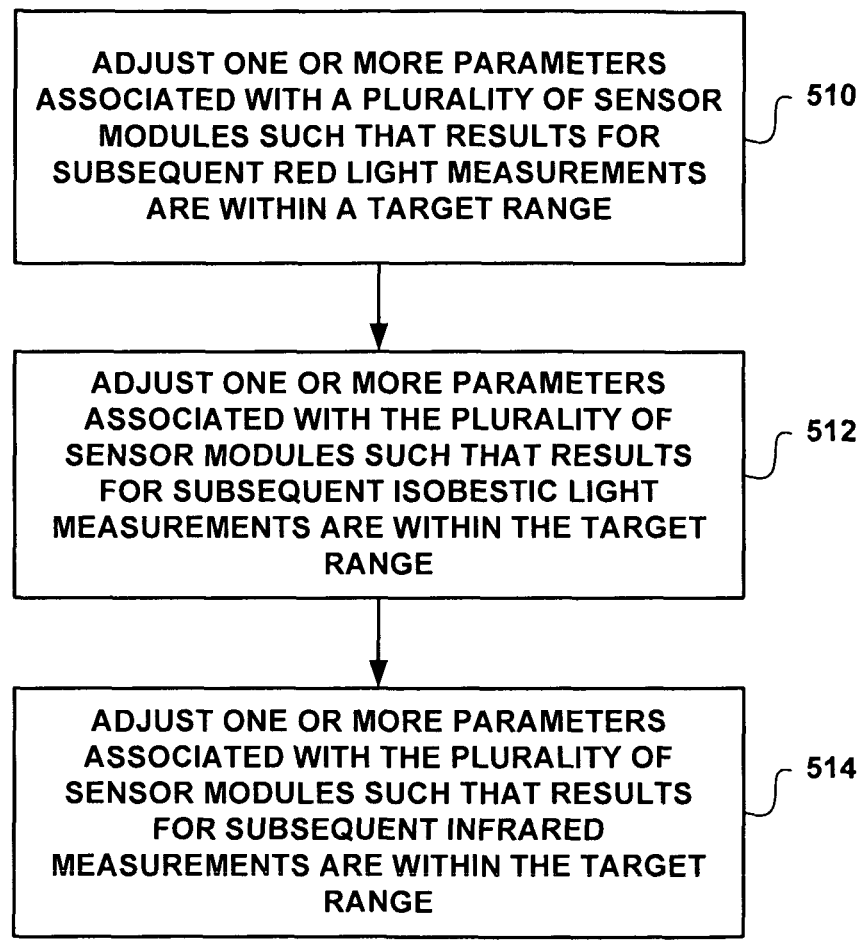
FIG. 17 is a flowchart illustrating an example method for providing closed loop adjustment of one or more operational parameters for different types of measurements according to a measurement type priority scheme.

FIG. 17 is a flowchart illustrating an example method for providing closed loop adjustment of one or more operational parameters for different types of measurements according to a measurement type priority scheme. When performing tissue perfusion measurements or blood oxygen content measurements, several different types of measurements may be performed that measure the amount of light received through the tissue for different colors of light. For example, the measurements may include red light measurements using LEDs that emit red light, isobestic light measurements using LEDs that emit isobestic light, and infrared measurements using LEDs that emit infrared light. Because it may be desirable to perform the measurements for differently colored light as close together in time as possible, the adjustment algorithm may provide closed loop adjustment for one or more parameters associated with the sensor modules such that all three types of light measurements are within the same target range.

According to the algorithm, host controller 202 may adjust one or more parameters within a plurality of sensor modules such that results for subsequent red light measurements are within a target range (510). After adjusting parameters for the red light measurements, host controller 202 may adjust one or more parameters within the plurality of sensor modules such that results for subsequent isobestic light measurements are within the target range (512). After adjusting parameters for the isobestic light measurements, host controller 202 may adjust one or more parameters within the plurality of sensor modules such that results for subsequent infrared light measurements are within the target range (514). In some examples, all three target ranges may correspond to the same target range. In other examples, one or more of the three target ranges may be different from each other.

As shown in FIG. 17, the parameters are calibrated with respect to red light measurements prior to being calibrated with respect to other types of light measurements because red light has the property of being the least transmissive through tissue relative to the other types of light. In some examples, the light detector sensor module may only have a single integration time (Tint) parameter and a single integration capacitor (Cint) parameter for all of the different types of light measurements. In such cases, the Cint and Tint parameters may be adjusted with respect to the red light measurement and not for the isobestic and/or infrared light measurements. Although described with respect to three different types of light measurements, the measurement type priority calibration scheme disclosed in FIG. 17 may be performed with any number of different types of measurements including a subset of the three types of light measurements described herein.

Figure 18:
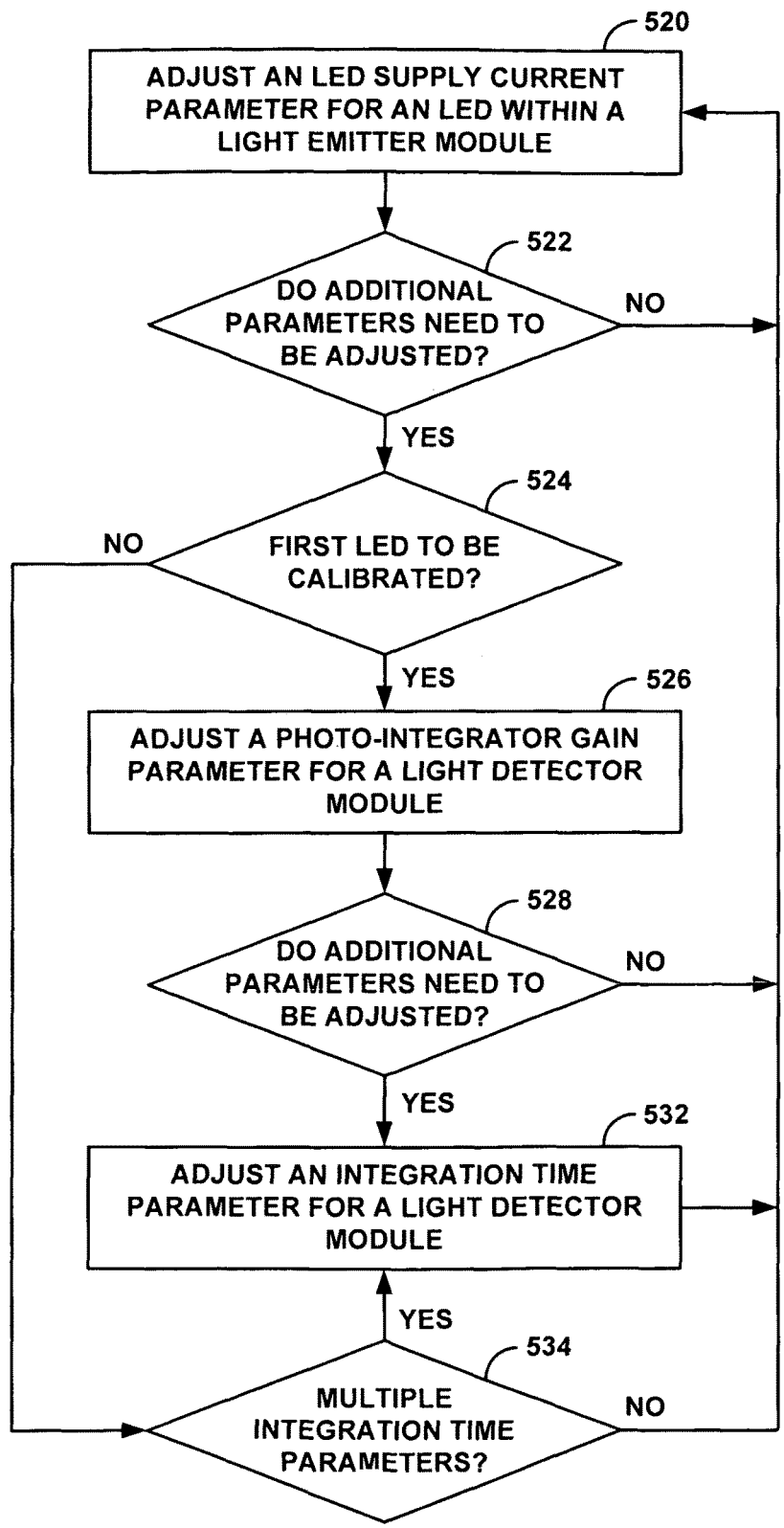
FIG. 18 is a flowchart illustrating an example method for providing closed loop adjustment of multiple operational parameters according to a parameter priority scheme.

FIG. 18 is a flowchart illustrating an example method for providing closed loop adjustment of multiple operational parameters according to a parameter priority scheme. Host controller 202 adjusts an LED supply current parameter (LEDi) for a first LED within a light emitter module (520). This step may involve host controller 202 performing one or more measurements and adjusting the LED supply current parameter until the results for the measurement are within a target range for further signal processing. In some cases, the LED supply current parameter may not be able to be adjusted in such a way as to cause the measurement results to be within the target range. In such a case, host controller 202 may adjust the LED supply current parameter until the parameter has reached a maximum or minimum value within the range of possible parameter values. The LED supply current parameter may reach a maximum value within the range of possible parameter values when the calibration measurements consistently produce results that are below the target range. Likewise, the LED supply current parameter may reach a minimum value within the range of possible parameter values when the calibration measurements consistently produce results that are above the target range.

In any case, host controller 202 may determine if additional parameters need to be adjusted for the particular light measurement (522). If the measurement results for the particular type of light measurement are already within the target range, then host controller 202 determines that no additional parameters need to be adjusted for that particular type of light measurement, and may proceed to adjust parameters for a different LED and/or light measurement (NO branch of 522). If the LED supply current is not able to be adjusted such that measurement results for the particular type of light measurement are within the target range, then host controller 202 determines that additional parameters need to be adjusted for the particular measurement, and may proceed to adjust one or more additional parameters in the light detector modules (YES branch of 522).

In order to determine which additional parameters to adjust, host controller 202 may determine if the LED currently being calibrated is the first LED to be calibrated for the implantable medical device (524). If the LED is the first LED to be calibrated, then host controller 202 may adjust a photo-integrator gain parameter (Cint) for a light detector module (526). Similar to the adjustment of the LED supply current parameter, this step may involve host controller 202 performing one or more measurements and adjusting the gain parameter until the results for the measurement are within the target range or until the gain parameter has reached a maximum or minimum value within the range of possible parameter values. The gain parameter may reach a maximum value within the range of possible parameter values when the calibration measurements consistently produce results that are below the target range. Likewise, the gain parameter may reach a minimum value within the range of possible parameter values when the calibration measurements consistently produce results that are above the target range.

Then, host controller 202 may determine if additional parameters need to be adjusted for the particular light measurement (528). If the measurement results for the particular type of light measurement are already within the target range, then host controller 202 may proceed to adjust parameters for a different LED and/or light measurement (NO branch of 528). If the gain of the photo-integrator is not able to be adjusted such that measurement results for the particular type of measurement are within the target range, then host controller 202 proceeds to adjust the integration time parameter in the light detector module (532).

Returning to decision box 524, if the LED that is currently being tested is not the first LED to be tested for the implantable medical device, then host controller 202 may proceed to determine how many integration parameters are available within the sensor modules (534). If only one integration parameter is available, then host controller 202 will not adjust the integration parameter, because the integration parameter has already been optimized for the first LED. Host controller 202 may set a status flag for the LED indicating that the LED was not able to be properly calibrated for light measurements, and proceed to adjust parameters for a different LED and/or light measurement (NO branch of 534). On the other hand, if the sensor modules within the implantable medical have multiple integration parameters (e.g., an integration parameter that corresponds to each different kind of light measurement), then host controller 202 may proceed to adjust the integration parameter corresponding to the particular LED (532). In general, implantable medical devices that are capable of performing the seven measurement sequence may only have a single integration time parameter, and implantable medical devices that are capable of performing the ten measurement sequence may have multiple integration time parameters.

Similar to the adjustment of the other parameters, when host controller 202 adjusts the integration time parameter, host controller 202 may perform one or more measurements and adjust the integration time parameter until the results for the measurement are within the target range or until the integration parameter has reached a maximum or minimum value within the range of possible parameter values. The integration time parameter may reach a maximum value within the range of possible parameter values when the calibration measurements consistently produce results that are below the target range. Likewise, the integration time parameter may reach a minimum value within the range of possible parameter values when the calibration measurements consistently produce results that are above the target range. If the integration time is not able to be adjusted such that measurement results for the particular type of measurement are within the target range, host controller 202 may set a status flag for the LED indicating that the LED was not able to be properly calibrated for light measurements, and proceed to adjust parameters for a different LED and/or light measurement.

FIGS. 19A-D are flowcharts illustrating an example closed loop parameter adjustment algorithm for use within an implantable medical device capable of performing a seven measurement sequence. Host controller 202 may initialize the parameters to nominal values (600). In one example, host controller may initialize the red LED supply current parameter (Red LEDi), the isobestic LED supply current parameter (Iso LEDi), and the infrared LED supply current parameter (IR LEDi) to initial values of 1 mA. As part of the example, host controller 202 may also initialize the photo-integrator gain parameter (Cint) to 12 pF and the integration time parameter to 800 μS. Of course, these initial values are merely examples of initial values that may be used for the calibration schemes described in this disclosure, and other initial values may be readily used in other examples.

Host controller 202 may perform a red light measurement (602) and determine whether the results for the measurement are within a target range for red light measurements (604). In one example, the target range for red light measurements may be a range centered around a value that is at approximately one-half of the usable input range (e.g. a value that is approximately at the midpoint of the usable input range or approximately midway through the usable input range) for an analog-to-digital converter within the detector sensor module. In such an example, the magnitude of the measured amount of light may be compared to the target range of magnitudes for red light measurements. In another example, the target range may be a minimum and/or maximum variance for the measured amount of light. In such an example, the variance of the measured amount of light may be compared to the target range of variances for red light measurements.

In some examples, the usable input range for the ADC may correspond to the entire range of possible input values for the ADC. In other examples, the usable input range may correspond to a subset of the range of possible input values for the ADC. For example, certain regions of the range of possible input values for the ADC may be excluded from the usable input range because those regions are reserved for other functions or because those regions are not able to be successfully processed by the ADC. In one example, a lower portion of the range of possible input values for the ADC (e.g. the lower ⅛th of the range) may be reserved for the offset voltage caused by the photo-integrator, and an upper portion of possible input values for the ADC (e.g. the upper 1/12th of the range) may be reserved because these values may not be able to be processed by the ADC. In such an example, the reserved upper and lower portions of the range of possible ADC input values are excluded from the usable input range.

Figure 19A:
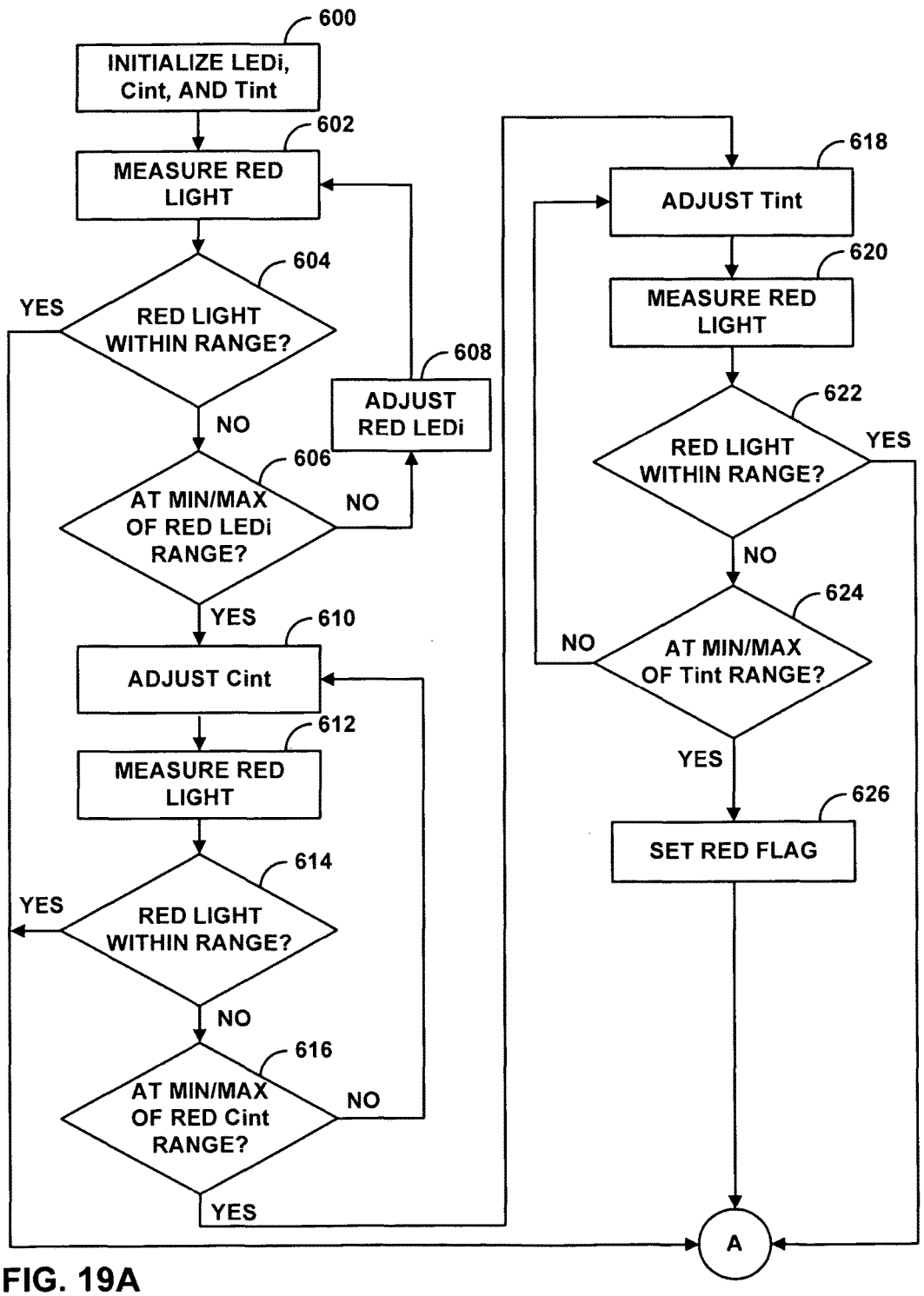
FIGS. 19A-D are flowcharts illustrating an example closed loop parameter adjustment algorithm for use within an implantable medical device capable of performing a seven measurement sequence.
Figure 19B:
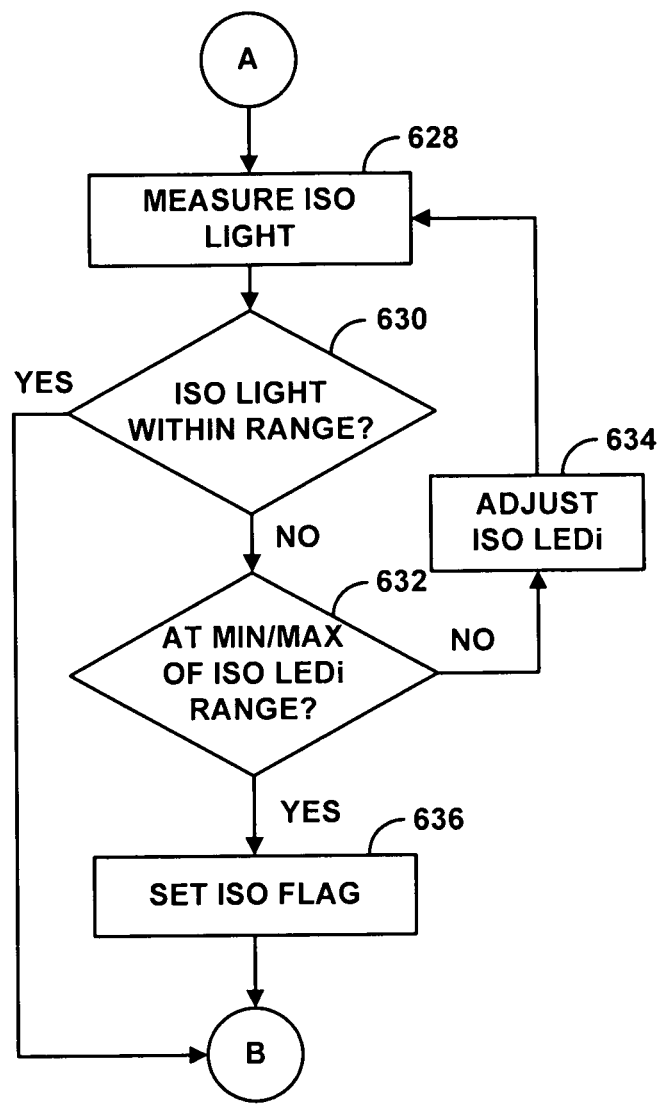

If the results are within the target range for red light measurements, host controller 202 may proceed to operation 628 in FIG. 19B in order to calibrate the next type of light measurement. On the other hand, if the results are not within the target range for red light measurements, host controller 202 may determine whether the Red LEDi parameter is at a minimum value or maximum value in a range of possible values for the Red LEDi parameter (606). If the Red LEDi parameter is not at a minimum value or a maximum value, host controller 202 may adjust the Red LEDi parameter in order to cause results for subsequent measurements to be within the target range for red light measurements (608). For example, if the results for the red light measurement were below the target range, host controller 202 may increase the Red LEDi parameter in order to cause more current to be supplied to the LED, which may in turn increase the intensity of the light emitted by the red LED as well as the amount of light detected by the photo-diode or photo-transistor in the detection module. On the other hand, if the results of the red light measurement were above the target range, host controller 202 may decrease the Red LEDi parameter in order to cause less current to be supplied to the LED, thereby decreasing the resulting amount of measured light by the detection module. Host controller 202 may then perform another red light measurement (602) and repeat this process until the results are within a target range for further signal processing or until the Red LEDi parameter is at a minimum or maximum value in the range of possible values for the Red LEDi parameter.

In cases where the Red LEDi parameter is at a minimum value or a maximum value, host controller 202 may proceed to adjust the Cint parameter (610). After adjusting the Cint parameter, host controller 202 may perform a red light measurement (612) and determine whether the results for the measurement are within a target range for the red light measurement (614). If the results are within the target range for red light measurements, host controller 202 may proceed to operation 628 in FIG. 19B in order to calibrate the next type of light measurement. On the other hand, if the results are not within the target range for red light measurements, host controller 202 may determine whether the Cint parameter is at a minimum value or maximum value in range of possible values for the Cint parameter (616).

If the Cint parameter is not at a minimum value or a maximum value, host controller 202 may adjust the Cint parameter in order to cause results for subsequent measurements to be within the target range for red light measurements (610). For example, if the results for the red light measurement were below the target range, host controller 202 may decrease the Cint parameter in order to increase the gain of the photodiode integrator, which may in turn increase the amplified value for the measured amount of received light. On the other hand, if the results of the red light measurement were above the target range, host controller 202 may increase the Cint parameter in order to decrease the gain of the photodiode integrator and cause the amplified value for the measured amount of received light to decrease. Host controller 202 may then perform another red light measurement (612) and repeat this process until the results are within a target range for further signal processing or until the Cint parameter is at a minimum or maximum value in the range of possible values for the Cint parameter.

In cases where the Cint parameter is at a minimum value or a maximum value, host controller 202 may proceed to adjust the Tint parameter (618). After adjusting the Tint parameter, host controller 202 may perform a red light measurement (620) and determine whether the results for the measurement are within a target range for the red light measurement (622). If the results are within the target range for red light measurements, host controller 202 may proceed to calibrate the next type of light measurement as illustrated in FIG. 19B. On the other hand, if the results are not within the target range for red light measurements, host controller 202 may determine whether the Tint parameter is at a minimum value or maximum value in range of possible values for the Tint parameter (624).

If the Tint parameter is not at a minimum value or a maximum value, host controller 202 may proceed to adjust the Tint parameter in order to cause results for subsequent measurements to be within the target range for red light measurements (618). For example, if the results for the red light measurement were below the target range, host controller 202 may increase the Tint parameter in order to increase the integration time for the photo-integrator, which may in turn increase the integrated value for the measured amount of received light. On the other hand, if the results of the red light measurement were above the target range, host controller 202 may decrease the Tint parameter in order to cause the integrated value for the measured amount of received light to decrease. Host controller 202 may then perform another red light measurement (620) and repeat this process until the results are within a target range for further signal processing or until the Tint parameter is at a minimum or maximum value in the range of possible values for the Tint parameter. In cases where the Tint parameter is at a minimum value or a maximum value, host controller 202 may set a red status flag to indicate that the operational parameters were not able to be adjusted to obtain valid and/or optimized red light measurements (626).

After adjusting the parameters for the red light measurement, host controller 202 may proceed to adjust parameters for the isobestic light measurement as illustrated in FIG. 19B. During the isobestic measurement calibration routine, host controller 202 may use the same Cint and Tint parameters as used for the red light measurements in FIG. 19A. Host controller 202 may perform an isobestic light measurement (628), and determine whether the results for the measurement are within a target range for isobestic light measurements (630). In one example, the target range for isobestic light measurements may be a range centered around a value that is at approximately one-half of the usable input range (e.g. a value that is approximately at the midpoint of the usable input range or approximately midway through the usable input range) for an analog-to-digital converter within the detector sensor module. In such an example, the magnitude of the measured amount of light may be compared to the target range of magnitudes for isobestic light measurements. In another example, the target range may be a minimum and/or maximum variance for the measured amount of light. In such an example, the variance of the measured amount of light may be compared to the target range of variances for isobestic light measurements. In some examples, the target range for isobestic light measurements may be the same range as the target range for red light measurements.

Figure 19C:
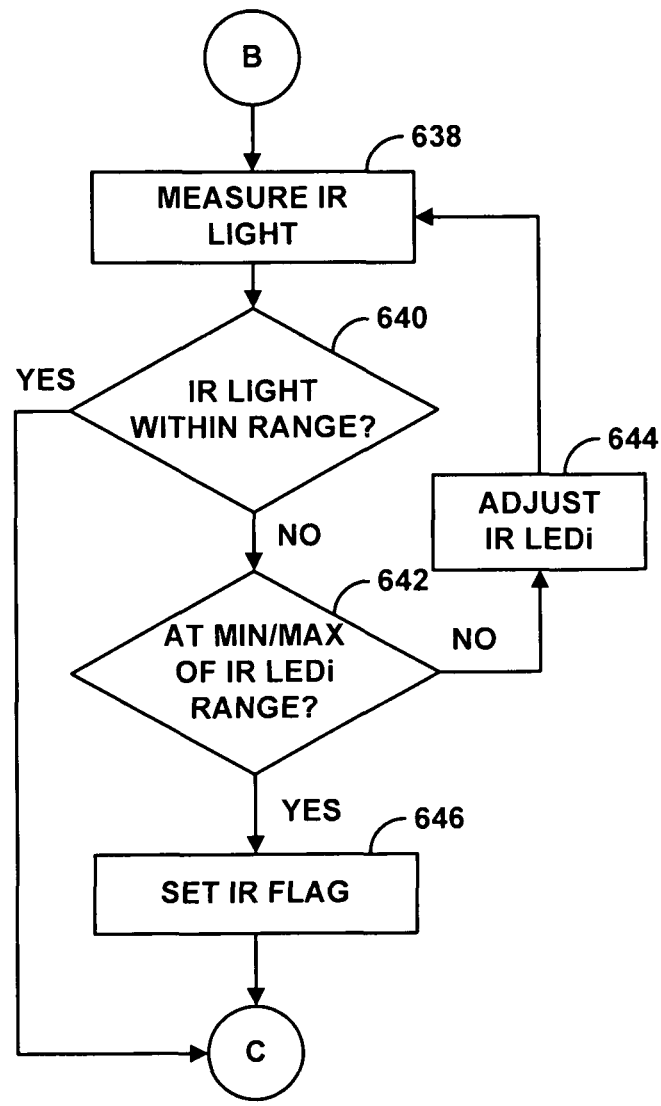

If the results are within the target range for isobestic light measurements, host controller 202 may proceed to operation 638 in FIG. 19C in order to calibrate the next type of light measurement. On the other hand, if the results are not within the target range for isobestic light measurements, host controller 202 may determine whether the Iso LEDi parameter is at a minimum value or maximum value in range of possible values for the Iso LEDi parameter (632). If the Iso LEDi parameter is not at a minimum value or a maximum value, host controller 202 may adjust the Iso LEDi parameter in order to cause results for subsequent measurements to be within the target range for isobestic light measurements (634). Similar to the Red LEDi parameter, increasing the Iso LEDi parameter increases the amount of current supplied to the isobestic LED. Likewise, decreasing the Iso LEDi parameter decreases the amount of current supplied to the isobestic LED. Host controller 202 may then perform another isobestic light measurement (628) and repeat this process until the results are within a target range for further signal processing or until the Iso LEDi parameter is at a minimum or maximum value in the range of possible values for the Iso LEDi parameter. In cases where the Iso LEDi parameter is at a minimum value or a maximum value, host controller 202 may set an Iso status flag to indicate that the operational parameters were not able to be adjusted to obtain valid and/or optimized isobestic measurements (636).

After adjusting the parameters for the red light measurements and the isobestic light measurements, host controller 202 may proceed to adjust parameters for the infrared light measurement as illustrated in FIG. 19C. During the infrared measurement calibration routine, host controller 202 may use the same Cint and Tint parameters as used for the red light measurements. Host controller 202 may perform an infrared light measurement (638), and determine whether the results for the measurement are within a target range for the infrared light measurement (640). In one example, the target range for infrared light measurements may be a range centered around a value that is at approximately one-half of the usable input range (e.g. a value that is approximately at the midpoint of the usable input range or approximately midway through the usable input range) for an analog-to-digital converter within the detector sensor module. In such an example, the magnitude of the measured amount of light may be compared to the target range of magnitudes for infrared light measurements. In another example, the target range may be a minimum and/or maximum variance for the measured amount of light. In such an example, the variance of the measured amount of light may be compared to the target range of variances for infrared light measurements. In some examples, the target range for infrared light measurements may be the same range as the target range for red light measurements, isobestic light measurements, or both.

Figure 19D:
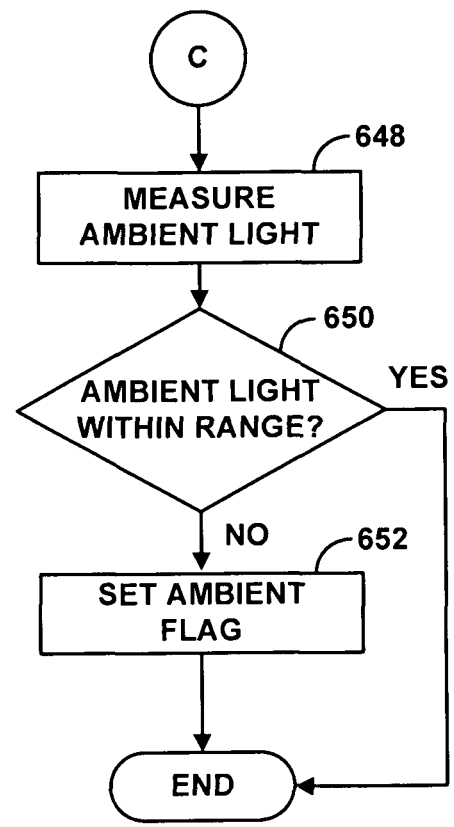

If the results are within the target range for infrared light measurements, host controller 202 may proceed to operation 648 in FIG. 19D in order to calibrate the ambient light measurement. On the other hand, if the results are not within the target range for infrared light measurements, host controller 202 may determine whether the IR LEDi parameter is at a minimum value or maximum value in a range of possible values for the IR LEDi parameter (642). If the IR LEDi parameter is not at a minimum value or a maximum value, host controller 202 may adjust the IR LEDi parameter in order to cause results for subsequent measurements to be within the target range for infrared light measurements (644). Similar to the Red LEDi parameter, increasing and decreasing the IR LEDi parameter causes the amount of current supplied to the infrared LED to increase and decrease respectively. Host controller 202 may then perform another infrared light measurement (638) and repeat this process until the results are within a target range for further signal processing or until the Iso LEDi parameter is at a minimum or maximum value in the range of possible values for the Iso LEDi parameter. In cases where the IR LEDi parameter is at a minimum value or a maximum value, host controller 202 may proceed to set an IR status flag to indicate that the operational parameters were not able to be adjusted to obtain valid and/or optimized infrared measurements (646).

After adjusting the parameters for the red light measurements, the isobestic light measurements, and the infrared light measurements, host controller 202 may perform a measurement of the amount of ambient light (648). Host controller 202 may determine if the ambient light is within a target range for further signal processing (650). As one example, the target range for ambient light measurements may be a range centered around a value that is at approximately one-quarter of the usable input range for an analog-to-digital converter within the detector sensor module. In such an example, the magnitude of the measured amount of light may be compared to the target range of magnitudes for ambient light measurements. In another example, the target range may be a minimum and/or maximum variance for the measured amount of light. In such an example, the variance of the measured amount of light may be compared to the target range of variances for ambient light measurements.

If the ambient light is within the target range, host controller 202 may finish the parameter adjustment algorithm. On the other hand, if the ambient light measurement is not within the target range, host controller 202 may set an ambient status flag indicating that the ambient light measurements were unable to be properly calibrated. Host controller 202 may then finish the parameter adjustment algorithm.

Host controller 202 may communicate the status flag information to one or more processors within the IMD that may make therapy decisions. When one or more of the status flags are set, the IMD may disregard tissue perfusion measurements when making therapy decisions. Example therapy decisions include whether a patient is experiencing ventricular fibrillation and/or whether to deliver a defibrillation shock to the patient. In cases where less than all of the status flags are set, the IMD may still rely on those measurements within the overall tissue perfusion measurement sequence that have been successfully calibrated.

FIGS. 20A-D are flowcharts illustrating an example closed loop parameter adjustment algorithm for use within an implantable medical device capable of performing a ten measurement sequence. Host controller 202 may initialize the parameters to nominal values (700). In one example, host controller may initialize the red LED supply current parameter (Red LEDi), the isobestic LED supply current parameter (Iso LEDi), and the infrared LED supply current parameter (IR LEDi) to initial values of 1 mA. As part of the example, host controller 202 may also initialize the red integration time parameter (Red Tint), the isobestic integration time parameter (Iso Tint), the infrared integration time parameter (IR Tint), and the ambient integration time parameters (Amb0 Tint, Amb1 Tint, Amb2 Tint) to 800 µS. In addition, as part of the example, host controller 202 may also initialize the photo-integrator gain parameter (Cint) to 12 pF. Again, these initial values are merely examples of initial values that may be used for the calibration schemes described in this disclosure, and other initial values may be readily used in other examples.

Host controller 202 may then perform a red light measurement (702) and determine whether the results for the measurement are within a target range for the red light measurement (704). Similar to the target ranges for the seven measurement sequence, the target ranges for the ten measurement sequence may include magnitude ranges and amplitude variation ranges. If the results are within the target range for red light measurements, host controller 202 may proceed to operation 728 in FIG. 20B in order to calibrate the next type of light measurement. On the other hand, if the results are not within the target range for red light measurements, host controller 202 may determine whether the Red LEDi parameter is at a minimum value or maximum value in range of possible values for the Red LEDi parameter (706). If the Red LEDi parameter is not at a minimum value or a maximum value, host controller 202 may proceed to adjust the Red LEDi parameter in order to cause results for subsequent measurements to be within the target range for red light measurements (708). Host controller 202 may then perform another red light measurement (702) and repeat this process until the results are within a target range for further signal processing or until the Red LEDi parameter is at a minimum or maximum value in the range of possible values for the Red LEDi parameter.

In cases where the Red LEDi parameter is at a minimum value or a maximum value, host controller 202 may proceed to adjust the Cint parameter (710). After adjusting the Cint parameter, host controller 202 may perform a red light measurement (712) and determine whether the results for the measurement are within a target range for the red light measurement (714). If the results are within the target range for red light measurements, host controller 202 may proceed to operation 728 in FIG. 20B in order to calibrate the next type of light measurement. On the other hand, if the results are not within the target range for red light measurements, host controller 202 may determine whether the Cint parameter is at a minimum value or maximum value in range of possible values for the Cint parameter (716). If the Cint parameter is not at a minimum value or a maximum value, host controller 202 may proceed to adjust the Cint parameter in order to cause results for subsequent measurements to be within the target range for red light measurements (710). Host controller 202 may then perform another red light measurement (712) and repeat this process until the results are within a target range for further signal processing or until the Cint parameter is at a minimum or maximum value in the range of possible values for the Cint parameter.

In cases where the Cint parameter is at a minimum value or a maximum value, host controller 202 may proceed to adjust the Red Tint and Amb0 Tint parameters (718). In some examples, the Amb0 Tint parameter may be adjusted to the same value as the Red Tint parameter. After adjusting the Tint parameters, host controller 202 may perform a red light measurement (720) and determine whether the results for the measurement are within a target range for the red light measurement (722). If the results are within the target range for red light measurements, host controller 202 may proceed to operation 728 in FIG. 20B in order to calibrate the next type of light measurement. On the other hand, if the results are not within the target range for red light measurements, host controller 202 may determine whether the Red Tint parameter and the Amb0 Tint parameter are at a minimum value or maximum value in range of possible values for the Red Tint parameter and the Amb0 Tint parameter (724). If the Tint parameters are not at a minimum value or a maximum value, host controller 202 may proceed to adjust the Red Tint parameter and the Red Amb0 parameter in order to cause results for subsequent measurements to be within the target range for red light measurements (718).

Host controller 202 may then perform another red light measurement (720) and repeat this process until the results are within a target range for further signal processing or until the Tint parameters are at a minimum or maximum value in the range of possible values for the Tint parameters. In cases where the Tint parameter is at a minimum value or a maximum value, host controller 202 may proceed to set a red status flag to indicate that the operational parameters were not able to be adjusted to obtain valid and/or optimized red light measurements (726).

Figure 20A:
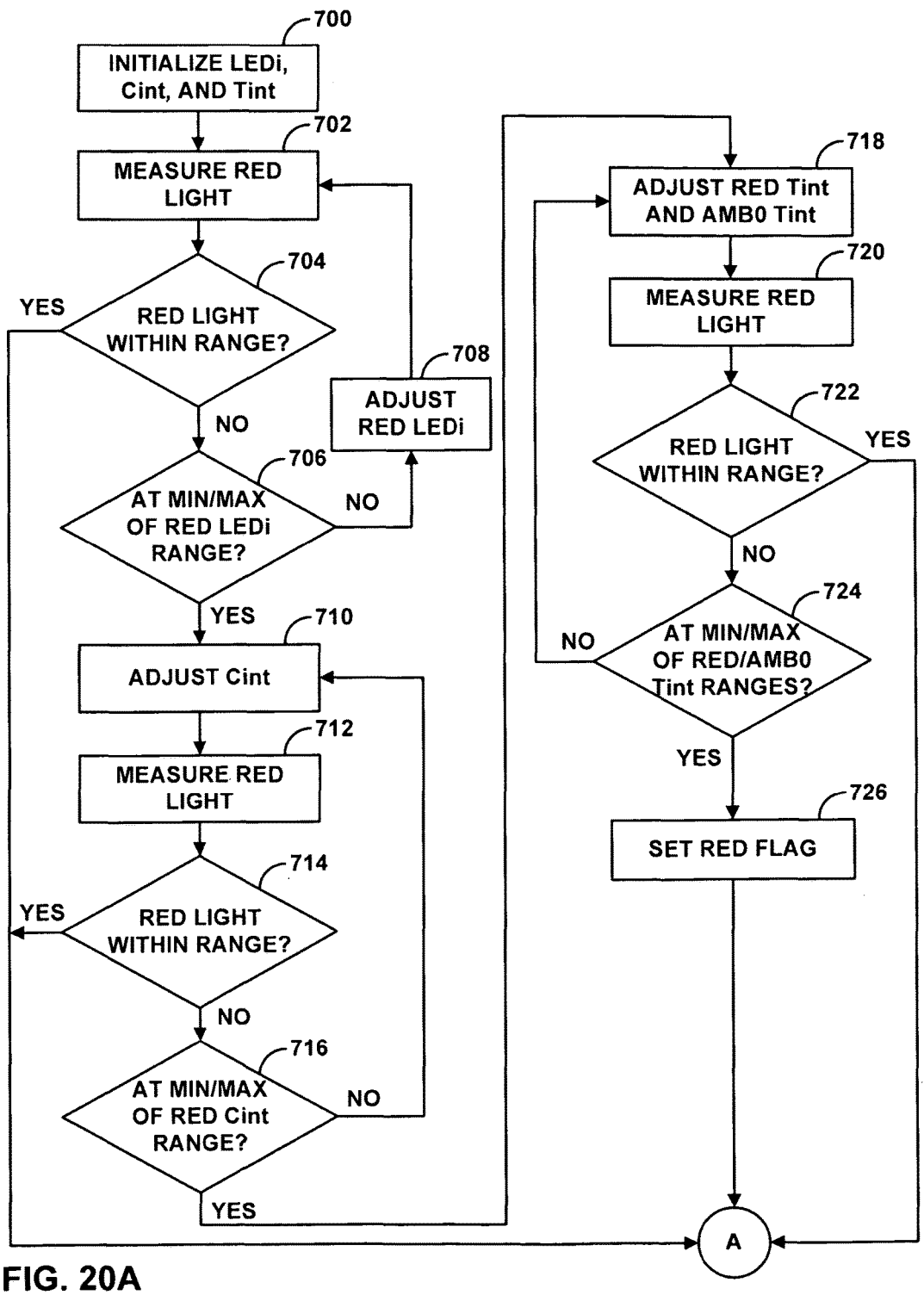
FIGS. 20A-D are flowcharts illustrating an example closed loop parameter adjustment algorithm for use within an implantable medical device capable of performing a ten measurement sequence.
Figure 20B:
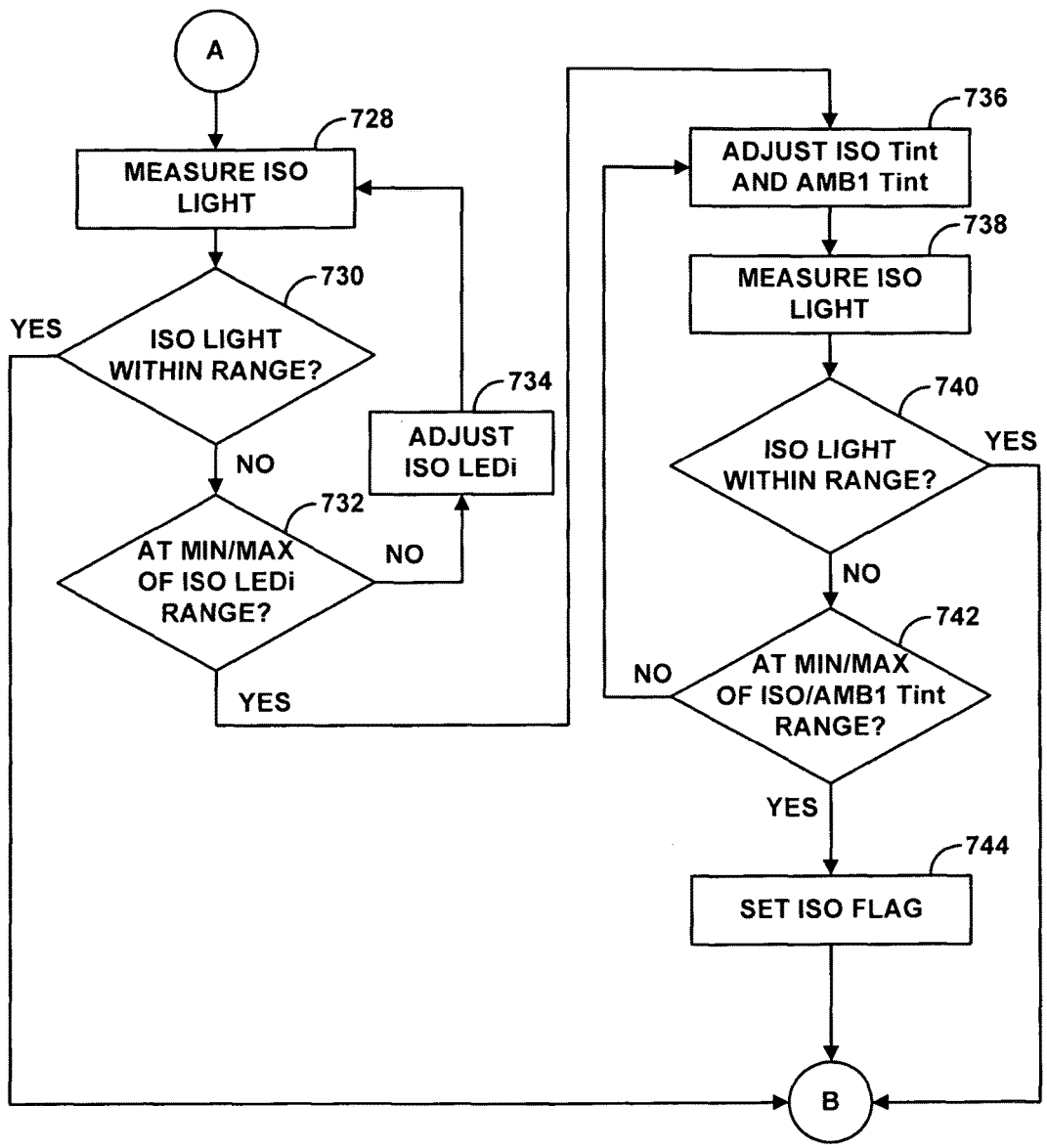

After adjusting the parameters for the red light measurement, host controller 202 may proceed to adjust parameters for the isobestic light measurement as shown in FIG. 20B. During the isobestic measurement calibration routine, host controller 202 may use the same Cint parameter as used for the red light measurements. Host controller 202 may perform an isobestic light measurement (728), and determine whether the results for the measurement are within a target range for the isobestic light measurement (730). If the results are within the target range for isobestic light measurements, host controller 202 may proceed to operation 746 in FIG. 20C in order to calibrate the next type of light measurement. On the other hand, if the results are not within the target range for isobestic light measurements, host controller 202 may determine whether the Iso LEDi parameter is at a minimum value or maximum value in range of possible values for the Iso LEDi parameter (732). If the Iso LEDi parameter is not at a minimum value or a maximum value, host controller 202 may proceed to adjust the Iso LEDi parameter in order to cause results for subsequent measurements to be within the target range for isobestic light measurements (734). Host controller 202 may then perform another isobestic light measurement (728) and repeat this process until the results are within a target range for further signal processing or until the Iso LEDi parameter is at a minimum or maximum value in the range of possible values for the Iso LEDi parameter.

In cases where the Iso LEDi parameter is at a minimum value or a maximum value, host controller 202 may proceed to adjust the Iso Tint and the Amb1 Tint parameters (736). In some examples, the Amb1 Tint parameter may be adjusted to the same value as the Iso Tint parameter. After adjusting the Tint parameters, host controller 202 may perform an isobestic light measurement (738) and determine whether the results for the measurement are within a target range for the isobestic light measurements (740). If the results are within the target range for isobestic light measurements, host controller 202 may proceed to operation 746 in FIG. 20C in order to calibrate the next type of light measurement. On the other hand, if the results are not within the target range for isobestic light measurements, host controller 202 may determine whether the Iso Tint parameter and the Amb1 Tint parameter are at a minimum value or maximum value in range of possible values for the Red Tint parameter and the Amb0 Tint parameter (742).

If the Tint parameters are not at a minimum value or a maximum value, host controller 202 may proceed to adjust the Iso Tint parameter and the Amb1 Tint parameter in order to cause results for subsequent measurements to be within the target range for red light measurements (736). Host controller 202 may then perform another isobestic light measurement (738) and repeat this process until the results for the isobestic light measurement are within a target range for further signal processing or until the Tint parameters are at a minimum or maximum value in the range of possible values for the Tint parameters. In cases where the Tint parameters are at a minimum value or a maximum value, host controller 202 may proceed set an isobestic status flag to indicate that the parameters were not able to be adjusted to obtain and/or optimized valid isobestic light measurements (744).

Figure 20C:
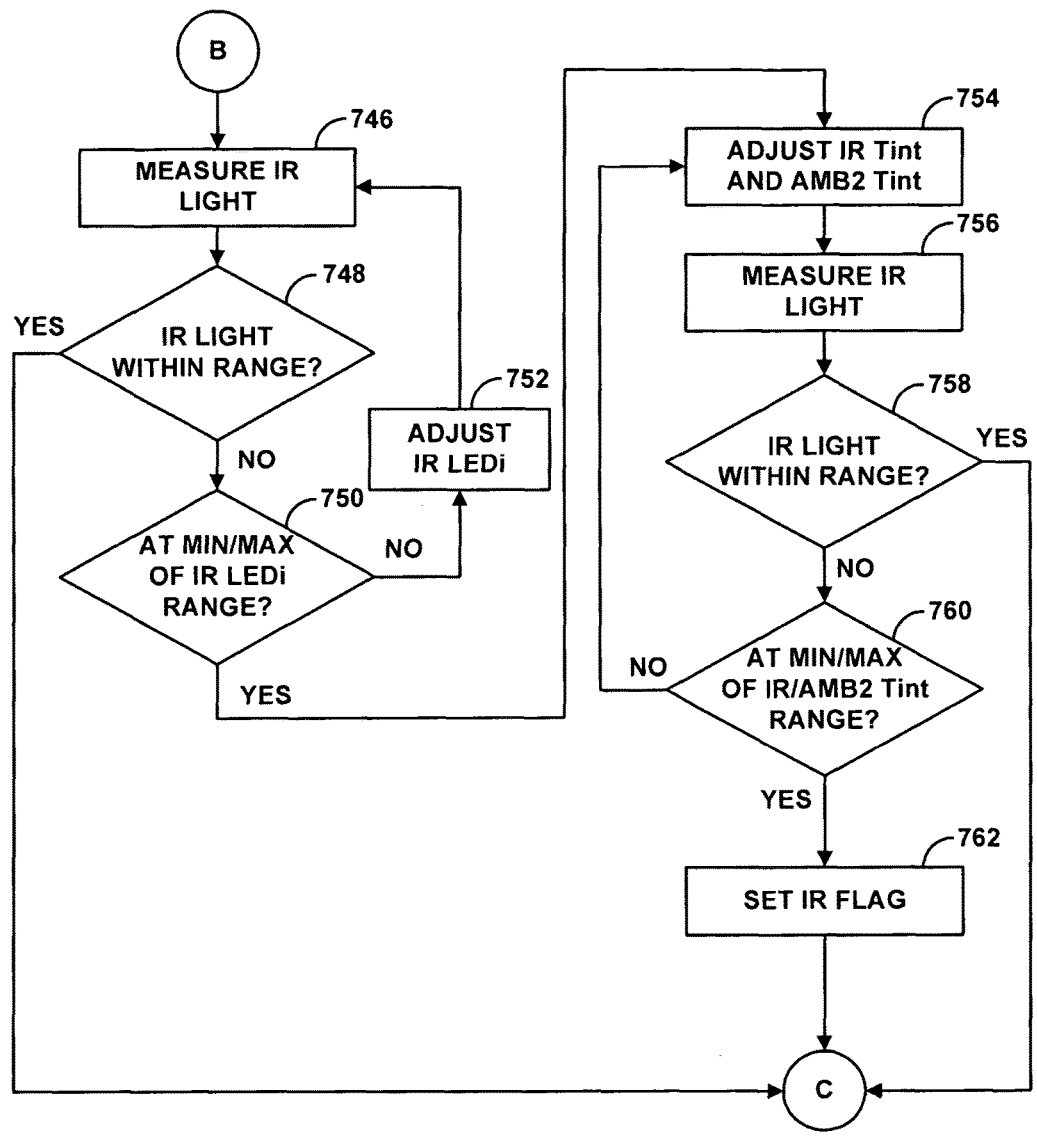
Figure 20D:
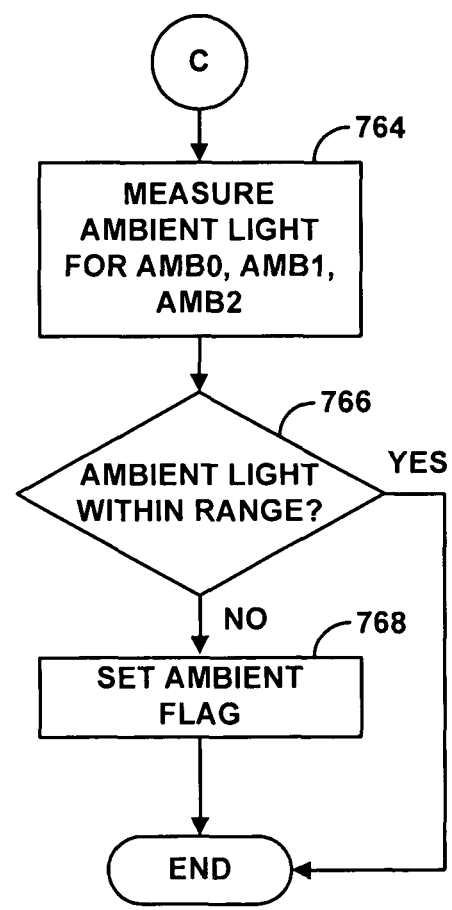

After adjusting the parameters for the red light measurements and the isobestic light measurements, host controller 202 may proceed to adjust parameters for the infrared light measurement as shown in FIG. 20C. During the infrared measurement calibration routine, host controller 202 may use the same Cint parameter as used for the red light measurements. Host controller 202 may perform an infrared light measurement (746), and determine whether the results for the measurement are within a target range for the infrared light measurement (748). If the results are within the target range for infrared light measurements, host controller 202 may proceed to operation 764 in FIG. 20D in order to calibrate the ambient light measurement. On the other hand, if the results are not within the target range for infrared light measurements, host controller 202 may determine whether the IR LEDi parameter is at a minimum value or maximum value in range of possible values for the IR LEDi parameter (750). If the IR LEDi parameter is not at a minimum value or a maximum value, host controller 202 may proceed to adjust the IR LEDi parameter in order to cause results for subsequent measurements to be within the target range for infrared light measurements (752). Host controller 202 may then perform another infrared light measurement (746) and repeat this process until the results are within a target range for infrared light measurements or until the IR LEDi parameter is at a minimum or maximum value in the range of possible values for the IR LEDi parameter.

In cases where the IR LEDi parameter is at a minimum value or a maximum value, host controller 202 may proceed to adjust the IR Tint and the Amb2 Tint parameters (754). In some examples, the Amb2 Tint parameter may be adjusted to the same value as the IR Tint parameter. After adjusting the Tint parameters, host controller 202 may perform an infrared light measurement (756) and determine whether the results for the measurement are within a target range for the infrared light measurements (758). If the results are within the target range for infrared light measurements, host controller 202 may proceed to operation 764 in FIG. 20D in order to calibrate the ambient light measurement. On the other hand, if the results are not within the target range for infrared light measurements, host controller 202 may determine whether the IR Tint parameter and the Amb2 Tint parameter are at a minimum value or maximum value in range of possible values for the IR Tint parameter and the Amb2 Tint parameter (758).

If the Tint parameters are not at a minimum value or a maximum value, host controller 202 may proceed to adjust the IR Tint parameter and the Amb2 Tint parameter in order to cause results for subsequent measurements to be within the target range for infrared light measurements (754). Host controller 202 may then perform another infrared light measurement (756) and repeat this process until the results for the infrared light measurement are within a target range for infrared light measurements or until the Tint parameters are at a minimum or maximum value in the range of possible values for the Tint parameters. In cases where the Tint parameters are at a minimum value or a maximum value, host controller 202 may set an infrared status flag to indicate that the parameters were not able to be adjusted to obtain valid infrared measurements (762).

After adjusting the parameters for the red light measurements, the isobestic light measurements, and the infrared light measurements, host controller 202 may perform a measurement of the amount of ambient light (764). Host controller 202 may then determine if the ambient light is within a target range for further signal processing (766) for each of the ambient integration time parameters (Amb0, Amb1, Amb2). If the ambient light is within the target range for each of the ambient integration time parameters, host controller 202 may finish the parameter adjustment algorithm. On the other hand, if the ambient light measurement is not within the target range, host controller 202 may set an ambient status flag indicating that the ambient light measurements were unable to be properly calibrated (768). Host controller 202 may then finish the parameter adjustment algorithm.

Host controller 202 may communicate the status flag information to one or more processors within the IMD that may make therapy decisions. When one or more of the status flags are set, the IMD may disregard tissue perfusion measurements when making therapy decisions. Example therapy decisions include whether a patient is experiencing ventricular fibrillation and/or whether to deliver a defibrillation shock to the patient. In cases where less than all of the status flags are set, the IMD may still rely on those measurements within the overall tissue perfusion measurement sequence that have been successfully calibrated.

Figure 21:
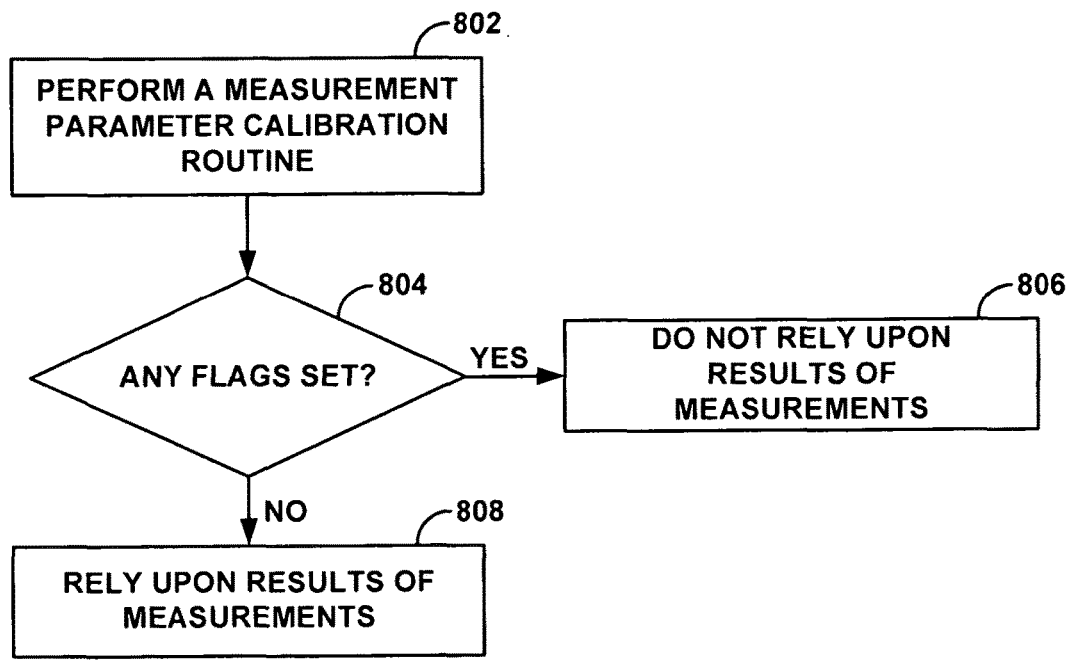
FIG. 21 is a flowchart illustrating an example method for determining whether to use tissue perfusion measurements in subsequent analysis of a patient's condition.

FIG. 21 is a flowchart illustrating an example method for determining whether to use optical perfusion measurements in subsequent analysis of a patient's condition. Host controller 202 may perform a measurement parameter calibration routine (802). The measurement calibration routine may be the 7-measurement sequence calibration routine illustrated in FIGS. 19A-C or the 10-measurement sequence calibration routine illustrated in FIGS. 20A-D. Host controller 202 may then determine if any flags are set (804). For example, one or more of a red status flag, an isobestic status flag, an infrared status flag, or an ambient light status flag may be set. If any of the status flags are set, host controller 202 may not rely upon the results of the optical perfusion measurements because the sensor modules were unable to be calibrated in order to generate valid results (806). On the other hand, if none of the flags are set, host controller 202 may rely upon the results of the tissue perfusion measurements to detect and/or confirm the presence of a physical condition, such as ventricular fibrillation (808).

In one example, the disclosure is directed to a method that includes transmitting a signal over a bus. The method further includes receiving the signal from the bus with a plurality of sensor modules. The method further includes coordinating timing for performance of sensor actions across the sensor modules based on the received signal in order to make the measurement. In some examples, the signal may be a pulsed signal that is substantially periodic. In additional examples, the signal may be a power pulse signal that supplies operational power and timing information to the plurality of sensor modules. In further examples, the measurement may be one of a tissue perfusion measurement, an oxygen sensing measurement, a sonomicrometry measurement, or a pressure measurement. In additional examples, the bus is a two-wire bus.

In some cases, the method may further include detecting a first signal condition within the received signal; performing a first sensor action, with a first sensor module, in response to the detected first signal condition; detecting a second signal condition within the received signal, wherein the first signal condition is defined to occur prior to or simultaneously with the second signal condition within the signal; and performing a second sensor action, with a second sensor module, in response to the detected second signal condition. In some cases, the method may further include detecting a third signal condition within the received signal; ceasing to measure the amount of received light in response to the detected third signal condition; detecting a fourth signal condition within the received signal, wherein the third signal condition is defined to occur prior to or simultaneously with the fourth signal condition within the signal; and ceasing to emit light in response to the detected fourth signal condition.

In some examples, performing the first sensor action may include emitting light in response to the detected first signal condition, and performing the second sensor action may include measuring an amount of received light in response to the detected second signal condition. In additional examples, the first sensor module may include a light emitting diode, and the second sensor module may include at least one of a photodiode, a phototransistor, or a photo integrator. In some examples, emitting light in response to the detected first signal condition may include emitting light having a wavelength selected from the group consisting of a red light wavelength, an isobestic light wavelength, and an infrared light wavelength.

In some cases, the signal may be a power pulse signal, the first signal condition may be a first number of received pulses from the power pulse signal, the second signal condition may be a second number of received pulses from the power pulse signal, and the second number of received pulses may be greater than the first number of received pulses.

In some cases, the first sensor module and the second sensor module are electrically coupled to the bus via the same port. In other cases, the first sensor module and the second sensor module are electrically coupled to the bus via different ports.

In some examples, the measurement may be a first measurement and the signal may be first signal. In such examples, the method may further include transmitting a second signal for making a second measurement from a implantable medical device to the plurality of sensor modules over the bus prior to receiving results from the first measurement at the implantable medical device; and coordinating timing for the performance of the sensor actions across the sensor modules based on the received signal in order to make the second measurement. In additional examples, the method may further include issuing a first triggering command for the first measurement over the bus in order to arm a first subset of the plurality of sensor modules prior to transmitting the first signal over the bus; issuing a second triggering command for a second measurement over the bus in order to arm a second subset of the plurality of sensor modules prior to transmitting the second signal over the bus; and performing analog-to-digital conversion for results of the first measurement, wherein a time period for issuing the second triggering command for the second measurement overlaps, at least partially, with a time period for performing analog-to-digital conversion of the first measurement.

In some examples, the method may further include performing, with a sensor module, a first sensor action prior to a second sensor action for each measurement, wherein a time period for performance of the first sensor action of a subsequent measurement overlaps, at least partially, with a time period for performance of the second sensor action of a previous measurement. In some cases, performing the first sensor action may include measuring an amount of received light during a first time period, and performing the second sensor action may include storing results of the measurement during a second time period. In additional cases performing the first sensor action may include measuring an amount of received light during a first time period, and performing the second sensor action may include converting the measured amount of received light to a digital value representing the measured amount of received light during a second time period.

In some examples, the method may further include storing results of multiple measurements within a buffer of a sensor module; and transmitting the results of the multiple measurements from the sensor module to an implantable medical device as a single packet over the bus.

The techniques described in this disclosure, including those attributed to ICD 16 or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The term "processor" or "processing circuitry" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

Various examples of the disclosure have been described. These and other examples are within the scope of the following claims.

The invention claimed is:

1. An implantable medical device comprising:
a host controller configured to transmit a signal over a two-wire bus; and
a plurality of sensor modules that are each coupled directly to each wire of the two wire bus to receive the signal from the bus, wherein a timing coordination for performance of sensor actions by each of the plurality of sensor modules is based on the received signal in order to make a measurement, wherein each of the plurality of sensor modules includes one or more light emitters and one or more light detectors, and wherein the plurality of sensor modules are each configured to simultaneously receive power from the two-wire bus.

2. The implantable medical device of claim 1, wherein the signal is a pulsed signal that is substantially periodic.

3. The implantable medical device of claim 1, wherein the signal is a power pulse signal that supplies operational power and timing information to the plurality of sensor modules.

4. The implantable medical device of claim 1, wherein the plurality of sensor modules comprises:
a first sensor module configured to receive the signal from the bus, detect a first signal condition within the received signal, and perform a first sensor action in response to the detected first signal condition; and
a second sensor module configured to receive the signal from the bus, detect a second signal condition within the received signal, and perform a second sensor action in response to the detected second signal condition, wherein the first signal condition is defined to occur prior to or simultaneously with the second signal condition within the signal.

5. The implantable medical device of claim 4,
wherein at least one light emitter of the one or more light emitters of the first sensor module is configured to emit light in response to the detected first signal condition, and
wherein at least one light detector of the one or more light detectors of the second sensor module is configured to measure an amount of received light in response to the detected second signal condition.

6. The implantable medical device of claim 5, wherein the second sensor module is further configured to detect a third signal condition within the received signal, wherein the first sensor module is further configured to detect a fourth signal condition within the received signal, wherein the at least one light detector of the second sensor module is further configured to cease to measure the amount of received light in response to the detected third signal condition, wherein the at least one light emitter of the first sensor module is further configured to cease to emit light in response to the detected fourth signal condition, and wherein the third signal condition is defined to occur prior to or simultaneously with the fourth signal condition within the signal.

7. The implantable medical device of claim 5, wherein the at least one light emitter of one or more light emitters of the first sensor module comprises a light emitting diode, and wherein the at least one light detector of the one or more light detectors of the second sensor module comprises at least one of a photodiode, a phototransistor, or a photo integrator.

8. The implantable medical device of claim 5, wherein the at least one light emitter of the one or more light emitters of the first sensor module is configurable to emit light having a wavelength selected from the group consisting of a red light wavelength, an isobestic light wavelength, and an infrared light wavelength.

9. The implantable medical device of claim 4, wherein the signal is a power pulse signal, wherein the first signal condition is a first number of received pulses from the power pulse signal, wherein the second signal condition is a second number of received pulses from the power pulse signal, and wherein the second number of received pulses is greater than the first number of received pulses.

10. The implantable medical device of claim 4, wherein the first sensor module and the second sensor module are electrically coupled to the bus via the same port.

11. The implantable medical device of claim 4, wherein the first sensor module and the second sensor module are electrically coupled to the bus via different ports.

12. The implantable medical device of claim 1, wherein the measurement is a first measurement and the signal is a first signal, wherein the host controller is further configured to transmit a second signal over the bus for making a second measurement prior to receiving results from the first measurement at the host controller, wherein the plurality of sensor modules are further configured to receive the second signal from the bus, and to coordinate timing for the performance of the sensor actions across the plurality of sensor modules based on the received signal in order to make the second measurement.

13. The implantable medical device of claim 12, wherein the host controller is further configured to issue a first triggering command for the first measurement over the bus in order to arm a first subset of the plurality of sensor modules prior to transmitting the first signal over the bus, and issue a second triggering command for a second measurement over the bus in order to arm a second subset of the plurality of sensor modules prior to transmitting the second signal over the bus, wherein at least one sensor module within the plurality of sensor modules is configured to perform analog-to-digital conversion for results of the first measurement, and wherein a time period for issuing the second triggering command for the second measurement overlaps, at least partially, with a time period for performing analog-to-digital conversion of the first measurement.

14. The implantable medical device of claim 1, wherein:
at least one light detector of the one or more light detectors of the first sensor module further comprises a photo integrator configured to measure an amount of received light during a first time period, and
the first sensor module further comprises an analog-to-digital converter configured to convert the measured amount of received light to a digital value representing the measured amount of received light during a second time period, wherein the first sensor action is measuring the amount of received light and the second sensor action is converting the measured amount of received light to a digital value representing the measured amount of received light.

15. The implantable medical device of claim 1, wherein a first sensor module within the plurality of sensor modules is further configured to store results of multiple measurements within a buffer of the first sensor module, and transmit the results of the multiple measurements from the first sensor module to the host controller as a single packet over the bus.

16. The implantable medical device of claim 1, wherein the measurement is one of a tissue perfusion measurement, an oxygen sensing measurement, a sonomicrometry measurement, or a pressure measurement.

17. The implantable medical device of claim 1, wherein the timing coordination of the plurality of sensor modules comprises controlling a sequence of activation and deactivation of at least one of the one or more light emitters and at least one of the one or more light detectors based on the received signal.

18. An implantable medical device comprising:
a common bus having a first wire and a second wire;
a host controller communicatively coupled to the common bus, wherein the host controller is configured to transmit a signal over the common bus; and
a plurality of sensor modules that are each directly coupled to the first wire and the second wire of the common bus and configured to receive the signal from the common bus, wherein the plurality of sensor modules coordinate timing for performance of sensor actions across the plurality of sensor modules in response to the received signal in order to make a measurement of a physiological parameter, wherein each of the plurality of sensor modules includes one or more light emitters and one or more light detectors, and wherein the plurality of sensor modules are each configured to simultaneously receive power from the common bus.

* * * * *